United States Patent
Hammond Cunningham et al.

(10) Patent No.: US 11,230,708 B2
(45) Date of Patent: Jan. 25, 2022

(54) CONCATEMERIC RNA MOLECULES, COMPOSITIONS, AND METHODS AND USES THEREOF

(71) Applicant: Massachusetts Institute of Technology, Cambridge, MA (US)

(72) Inventors: Paula T. Hammond Cunningham, Newton, MA (US); Connie Wu, Cambridge, MA (US); Kevin E. Shopsowitz, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 18 days.

(21) Appl. No.: 16/063,478

(22) PCT Filed: Dec. 16, 2016

(86) PCT No.: PCT/US2016/067233
§ 371 (c)(1),
(2) Date: Jun. 18, 2018

(87) PCT Pub. No.: WO2017/106683
PCT Pub. Date: Jun. 22, 2017

(65) Prior Publication Data
US 2020/0377880 A1    Dec. 3, 2020

Related U.S. Application Data

(60) Provisional application No. 62/269,249, filed on Dec. 18, 2015.

(51) Int. Cl.
*C12N 15/113* (2010.01)

(52) U.S. Cl.
CPC ........ *C12N 15/113* (2013.01); *C12N 2310/14* (2013.01); *C12N 2310/531* (2013.01); *C12N 2330/50* (2013.01)

(58) Field of Classification Search
None
See application file for complete search history.

(56) References Cited

U.S. PATENT DOCUMENTS

| | | | |
|---|---|---|---|
| 6,815,167 B2 | 11/2004 | Crothers et al. | |
| 6,977,153 B2 | 12/2005 | Kumar et al. | |
| 8,575,330 B2 | 11/2013 | Tan | |
| 2007/0141594 A1 | 6/2007 | Luo et al. | |
| 2011/0009281 A1 | 1/2011 | Micklem et al. | |

FOREIGN PATENT DOCUMENTS

| | | |
|---|---|---|
| WO | WO-2005/059157 A2 | 6/2005 |
| WO | WO-2006/007569 A2 | 1/2006 |
| WO | WO-2012/051152 A2 | 4/2012 |

OTHER PUBLICATIONS

Defintion of "concatemer" [retrieved on Jan. 12, 2021], Retrieved from the internet: <URL:https://medical-dictionary.thefreedictionary.com/concatemer>.*
International Search Report and Written Opinion for International Application No. PCT/US2016/067233 dated May 31, 2017.
Roh et al., "A Multi-RNAi Microsponge Platform of Simultaneous Controlled Delivery of Multiple Small Interfering RNAS," Angew Chern Int Ed Engl, 55(10): 3347-3351 (2015).
Seyhan et al., "RNA interference from multimeric shRNAs generated by rolling circle transcription," Oligonucleotides, 16(4): 353-363 (2006).
Shopsowitz et al., "Composite RNAi-microsponges form through self-assembly of the organic and inorganic products oftranscription," Small, 10(8): 1623-1633 (2014).
Shopsowitz et al., "Periodic-shRNA molecules are capable of gene silencing, cytotoxicity and innate immune activation in cancer cells," Nucleic Acids Research, 44(2): 545-557 (2015).
Siolas et al.,"Synthetic shRNAs as potent RNAi triggers," Nat Biotechnol, 23(2): 227-231 (2005).
Wu et al., "Engineering Periodic shRNA for Enhanced Silencing Efficacy," Molecular Therapy, 24(6): 1070-1077 (2016).

* cited by examiner

*Primary Examiner* — Tracy Vivlemore
(74) *Attorney, Agent, or Firm* — Foley Hoag LLP

(57) ABSTRACT

The present invention relates to concatemeric RNA molecules, compositions, particles, and methods of uses thereof.

44 Claims, 49 Drawing Sheets
(7 of 49 Drawing Sheet(s) Filed in Color)
Specification includes a Sequence Listing.

A

B

C

D

E

F

A

B

C

D

E

A

B 15 nm

A

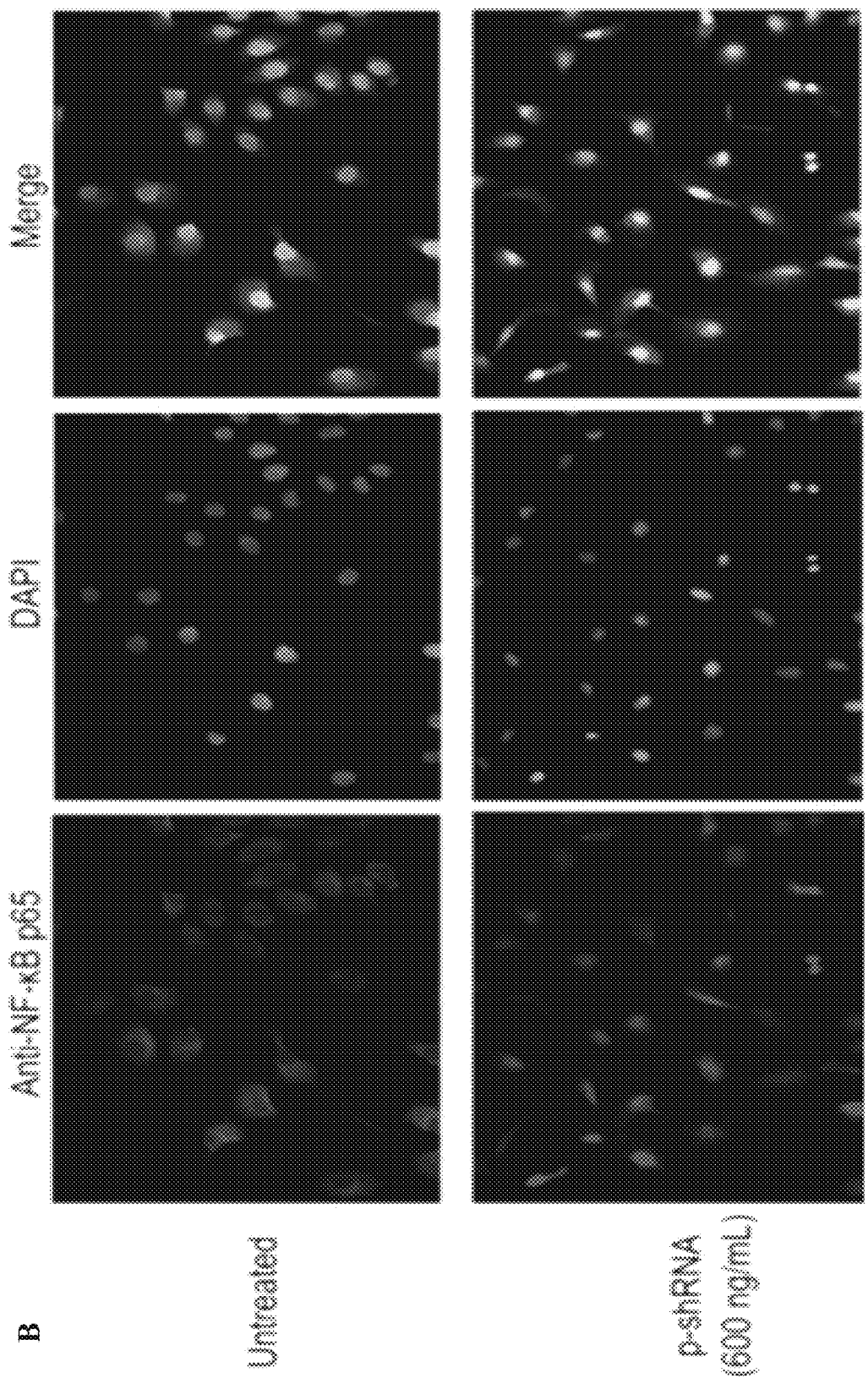

A

SEQUENCE LISTING

```
<160> NUMBER OF SEQ ID NOS: 92

<210> SEQ ID NO 1
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1 ggucag                                                                  6

<210> SEQ ID NO 2
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
aacuuccuau ca                                                          12

<210> SEQ ID NO 3
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3 aagaaa                                                                  6

<210> SEQ ID NO 4
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
gggggggggg gg                                                          12

<210> SEQ ID NO 5
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5 auauca                                                                  6
```

```
<210> SEQ ID NO 6
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ggcuuccuau gg                                                             12

<210> SEQ ID NO 7
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7 gggggg                                                                     6

<210> SEQ ID NO 8
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8 aaaaaa                                                                     6

<210> SEQ ID NO 9
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9 ccaccc                                                                     6

<210> SEQ ID NO 10
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
acuuccuggc ca                                                             12

<210> SEQ ID NO 11
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11 aaaaaa                                                                     6
```

```
<210> SEQ ID NO 12
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12 aaaggg                                                                     6

<210> SEQ ID NO 13
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13 ccaccc                                                                     6

<210> SEQ ID NO 14
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
acuuccuggc ca                                                             12

<210> SEQ ID NO 15
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15 cccccc                                                                     6

<210> SEQ ID NO 16
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16 uuuuuu                                                                     6

<210> SEQ ID NO 17
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17 cuucuu                                                                     6

<210> SEQ ID NO 18
```

```
<211> LENGTH: 7
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18 cguuacu                                                                    7

<210> SEQ ID NO 19
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cgcggcauua augcagcuuu auugcc                                              26

<210> SEQ ID NO 20
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20 ctgacc                                                                     6

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgataggaag tt                                                             12

<210> SEQ ID NO 22
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 tttctt                                                                     6

<210> SEQ ID NO 23
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ccataggaag cc                                                             12

<210> SEQ ID NO 24
<211> LENGTH: 12
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cccccccccc cc                                                           12

<210> SEQ ID NO 25
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25 tgatat                                                                   6

<210> SEQ ID NO 26
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26 cccccc                                                                   6

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27 tttttt                                                                   6

<210> SEQ ID NO 28
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28 gggtgg                                                                   6

<210> SEQ ID NO 29
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
tggccaggaa gt                                                           12

<210> SEQ ID NO 30
<211> LENGTH: 6
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 30 tttttt                                                                      6

<210> SEQ ID NO 31
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31 gggttt                                                                      6

<210> SEQ ID NO 32
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32 gggtgg                                                                      6

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
tggccaggaa gt                                                              12

<210> SEQ ID NO 34
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34 gggggg                                                                      6

<210> SEQ ID NO 35
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 aaaaaa                                                                      6

<210> SEQ ID NO 36
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 aagaag                                                                   6

<210> SEQ ID NO 37
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37 agtaacg                                                                  7

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
ggcaataaag ctgcattaat gccgcg                                            26

<210> SEQ ID NO 39
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cctgaagttc atgacatgaa cttcagggtc agcttgctga cagcaagctg ac               52

<210> SEQ ID NO 40
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cctgaagttc attgtttgaa cttcagggtc agcttgcttg ttgcaagctg ac               52

<210> SEQ ID NO 41
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cctgaagttc atgacaggat gaacttcagg gtcagcttgc tgacaggagc aagctgac         58

<210> SEQ ID NO 42
<211> LENGTH: 58
<212> TYPE: DNA
<213> ORGANISM: Artificial Sequence
<220> FEATURE:

<223> OTHER INFORMATION: Description of Artificial Sequence: Synthetic
       oligonucleotide

<400> SEQUENCE: 42
cctgaagttc aacaggaagt gaacttcagg gtcagcttgc acaggaaggc aagctgac         58

<210> SEQ ID NO 43
<211> LENGTH: 57
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 43
cctgaagttc atgacaggaa gtgaacttca gggtcagctt gcttgttgca agctgac          57

<210> SEQ ID NO 44
<211> LENGTH: 62
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 44
cctgaagttc atgacaggaa gtgaacttca gggtcagctt gctgacagga aggcaagctg       60
ac                                                                      62

<210> SEQ ID NO 45
<211> LENGTH: 62
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 45
cctgaagttc atgacaggaa gtgaacttca gggtcagctt gctgagagga aggcaagctg       60
ac                                                                      62

<210> SEQ ID NO 46
<211> LENGTH: 62
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 46
cctgaagttc atgagaggaa gtgaacttca gggtcagctt gctgagagga aggcaagctg       60
ac                                                                      62

<210> SEQ ID NO 47
<211> LENGTH: 62
<212> TYPE: DNA
<213> ORGANISM: Artificial Sequence
<220> FEATURE:
<223> OTHER INFORMATION: Description of Artificial Sequence: Synthetic
       oligonucleotide

<400> SEQUENCE: 47
cctgaagttc atccgaccag ctgaacttca gggtcagctt gctccgacca gcgcaagctg       60
ac                                                                      62

<210> SEQ ID NO 48
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
cctgaagttc acccccccc ctgaacttca gggtcagctt gcccccccc ccgcaagctg    60 ac                                                                62

<210> SEQ ID NO 49
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctgaagttc atgacaggaa gattgaactt cagggtcagc ttgctgacag gaagatgcaa    60
gctgac                                                              66

<210> SEQ ID NO 50
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
cctgaagttc atctgtgaca ggaagcagat gaacttcagg gtcagcttgc tgacaggaag    60
gcaagctgac                                                          70

<210> SEQ ID NO 51
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cctgaagttc atctgtgaca ggaagtagat gaactttagg gtcagcttgt tgacaggaag    60
gcaagctgac                                                          70

<210> SEQ ID NO 52
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cctgaagttc atctgcatga caggaagtgc agatgaactt cagggtcagc ttgctgacag    60
gaaggcaagc tgac                                                     74

<210> SEQ ID NO 53
<211> LENGTH: 74

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cctgaagttc atctgcatga caggaagtgt agatgaattt tagggttagc ttgttgacag      60
gaaggcaagc tgac                                                       74

<210> SEQ ID NO 54
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
cctgaagttc atctgcacct gacaggaagg gtgtagatga attttagggt tagtttgttg      60
acaggaaggc aagctgac                                                   78

<210> SEQ ID NO 55
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ctctagagga tgtgacagga agcatcctct agaggataga atgtgacagg aagcattcta      60
tc                                                                    62

<210> SEQ ID NO 56
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
ctcagcgtaa gtgattgaca ggaagatcac ttacgctgag tacttcgatt tgacaggaag      60
aatcgaagta                                                            70

<210> SEQ ID NO 57
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gagcacttct tcatctgata ggaagttgat gaagaagtgc tcgtcctcgt cccccccgg       60 acgaggac                                                              68

<210> SEQ ID NO 58
<211> LENGTH: 68
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 58
cctgaagttc atctgtgata ggaagttcag atgaacttca gggtcagctt gccccccgc        60 aagctgac                                                                68

<210> SEQ ID NO 59
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cctgaagttc atctgtgata ggaagttcag atgaacttca gggtcagctt gccccccgc        60 aagctgac                                                                68

<210> SEQ ID NO 60
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gagcacttct tcatctgata ggaagttgat gaagaagtgc tcgtcctcgt ccccccccgg        60
acgaggac                                                                68

<210> SEQ ID NO 61
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cctgaagttc atctgtgata ggaagttcag atgaacttca gggtcagctt gcctgaccgc        60
aagctgac                                                                68

<210> SEQ ID NO 62
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
cctgaagttc atctgtgata ggaagttcag atgaacttca gggtcagctt gctttcttgc        60
aagctgac                                                                68

<210> SEQ ID NO 63
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
cctgaagttc atctgtgata ggaagttcag atgaacttca gggtcagctt gcccatagga    60
agccgcaagc tgac                                                      74

<210> SEQ ID NO 64
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cctgaagttc atctgtgata ggaagttcag atgaacttca gggtcagctt gccccccccc    60
ccccgcaagc tgac                                                      74

<210> SEQ ID NO 65
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cctgaagttc atctgcccccc ccccccccag atgaacttca gggtcagctt gctgatatgc    60
aagctgac                                                             68

<210> SEQ ID NO 66
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
cctgaagttc atctgccata ggaagcccag atgaacttca gggtcagctt gctgatatgc    60
aagctgac                                                             68

<210> SEQ ID NO 67
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cctgaagttc atctgtgata ggaagttcag atgaacttca gggtcagctt gcccccctgc    60
aagctgac                                                             68

<210> SEQ ID NO 68
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
cctgaagttc atgataggaa gtttgaactt cagggtcagc ttgccccccc gcaagctgac    60

<210> SEQ ID NO 69
```

```
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
cctgaagttc atctgcatga taggaagttt gcagatgaac ttcagggtca gcttgccccc      60
ccgcaagctg ac                                                         72

<210> SEQ ID NO 70
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
cctgaagttc atctgcacct gataggaagt tggtgcagat gaacttcagg gtcagcttgc      60 cccccgcaa gctgac                                                      76

<210> SEQ ID NO 71
<211> LENGTH: 63
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
gcaagcugac ccugaaguuc aucugaacuu ccaucacag augaacuuca gggucagcuu       60
gcg                                                                   63

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
gcaagcugac ccugaaguuc autt                                            24

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ggacgaggac gagcacuuct t                                               21

<210> SEQ ID NO 74
<211> LENGTH: 52
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(52)
<223> OTHER INFORMATION: Cyclic

<400> SEQUENCE: 74
gtttgaactt caggcagtcg aacgttgttc gttcgactgc ctgaagttca tt    52

<210> SEQ ID NO 75
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(58)
<223> OTHER INFORMATION: Cyclic

<400> SEQUENCE: 75
gaagtgaact tcaggcagtc gaacggaagg acacgttcga ctgcctgaag ttcaacag    58

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(57)
<223> OTHER INFORMATION: Cyclic

<400> SEQUENCE: 76
ggaagtgaac ttcaggcagt cgaacgttgt tcgttcgact gcctgaagtt catgaca    57

<210> SEQ ID NO 77
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(62)
<223> OTHER INFORMATION: Cyclic

<400> SEQUENCE: 77
ggaagtgaac ttcaggcagt cgaacggaag gacagtcgtt cgactgcctg aagttcatga    60
ca    62

<210> SEQ ID NO 78
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(66)
<223> OTHER INFORMATION: Cyclic

```
<400> SEQUENCE: 78
gaagattgaa cttcaggcag tcgaacgtag aaggacagtc gttcgactgc ctgaagttca    60
tgacag                                                               66

<210> SEQ ID NO 79
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 79
ugaacuucag ggucagcuug ccuuccucuc agcaagcuga cccugaaguu cacuuccugu    60
caugaacuuc agggucagcu ugccuuccuc ucagcaagcu gacccugaag uucacuuccu   120
guca                                                                124

<210> SEQ ID NO 80
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 80
ugaacuucag ggucagcuug ccuuccucuc agcaagcuga cccugaaguu cacuuccugu    60
caugaacuuc agggucagcu ugccuuccuc ucagcaagcu gacccugaag uucacuuccu   120
guca                                                                124

<210> SEQ ID NO 81
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 81
gcaagcugac ccugaaguuc acuuccuguc augaacuuca gggucagcuu gccuuccucu    60
cagcaagcug acccugaagu ucacuuccug ucaugaacuu cagggucagc uugccuuccu   120
cuca                                                                124

<210> SEQ ID NO 82
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 82
gcaagcugac ccugaaguuc acuuccuguc augaacuuca gggucagcuu gccuuccucu    60
cagcaagcug acccugaagu ucacuuccug ucaugaacuu cagggucagc uugccuuccu   120
cuca                                                                124

<210> SEQ ID NO 83
<211> LENGTH: 124
<212> TYPE: RNA
<213> ORGANISM: Artificial Sequence
```

```
<220> FEATURE:
<223> OTHER INFORMATION: Description of Artificial Sequence: Synthetic
      polynucleotide

<400> SEQUENCE: 83
ugaacuucag ggucagcuug ccuuccucuc agcaagcuga cccugaaguu cacuuccugu      60
caugaacuuc agggucagcu ugccuuccuc ucagcaagcu gacccugaag uucacuucgu     120
guca                                                                  124

<210> SEQ ID NO 84
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 84
gcaagcugac ccugaaguuc acuuccuguc augaacuuca gggucagcuu gccuuccucu      60
cagcaagcug acccugaagu ucacuuccug ucaugaacuu cagggucagc uugccuuccu    120
cuca                                                                  124

<210> SEQ ID NO 85
<211> LENGTH: 124
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 85
gcaagcugac ccugaaguuc acuuccuguc augaacuuca gggucagcuu gccuuccucu      60
cagcaagcug acccugaagu ucacuuccug ucaugaacuu cagggucagc uugccuuccu    120
cuca                                                                  124

<210> SEQ ID NO 86
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(68)
<223> OTHER INFORMATION: Cyclic
<220> FEATURE:
<221> NAME/KEY: modified_base
<222> LOCATION: (7)..(31)
<223> OTHER INFORMATION: a, c, t, g, unknown or other
<220> FEATURE:
<221> NAME/KEY: modified_base
<222> LOCATION: (44)..(68)
<223> OTHER INFORMATION: a, c, t, g, unknown or other

<400> SEQUENCE: 86
ccccccnnnn nnnnnnnnn nnnnnnnnnn ntgataggaa guunnnnnnn nnnnnnnnn       60 nnnnnnnn                                                              68

<210> SEQ ID NO 87
<211> LENGTH: 68
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(68)
<223> OTHER INFORMATION: Cyclic
<220> FEATURE:
<221> NAME/KEY: modified_base
<222> LOCATION: (7)..(31)
<223> OTHER INFORMATION: a, c, t, g, unknown or other
<220> FEATURE:
<221> NAME/KEY: modified_base
<222> LOCATION: (44)..(68)
<223> OTHER INFORMATION: a, c, t, g, unknown or other

<400> SEQUENCE: 87
ctgaccnnnn nnnnnnnnnn nnnnnnnnnn ntgataggaa gttnnnnnnn nnnnnnnnnn       60 nnnnnnnn                                                                68

<210> SEQ ID NO 88
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(68)
<223> OTHER INFORMATION: Cyclic
<220> FEATURE:
<221> NAME/KEY: modified_base
<222> LOCATION: (7)..(31)
<223> OTHER INFORMATION: a, c, t, g, unknown or other
<220> FEATURE:
<221> NAME/KEY: modified_base
<222> LOCATION: (44)..(68)
<223> OTHER INFORMATION: a, c, t, g, unknown or other

<400> SEQUENCE: 88
tttcttnnnn nnnnnnnnnn nnnnnnnnnn ntgataggaa gttnnnnnnn nnnnnnnnnn       60 nnnnnnnn                                                                68

<210> SEQ ID NO 89
<211> LENGTH: 74
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(74)
<223> OTHER INFORMATION: Cyclic
<220> FEATURE:
<221> NAME/KEY: modified_base
<222> LOCATION: (13)..(37)
<223> OTHER INFORMATION: a, c, t, g, unknown or other
<220> FEATURE:
<221> NAME/KEY: modified_base
<222> LOCATION: (50)..(74)
<223> OTHER INFORMATION: a, c, t, g, unknown or other

<400> SEQUENCE: 89
ccataggaag ccnnnnnnnn nnnnnnnnnn nnnnnnntga taggaagttn nnnnnnnnnn       60
nnnnnnnnnn nnnn                                                         74

<210> SEQ ID NO 90
<211> LENGTH: 74
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(74)
<223> OTHER INFORMATION: Cyclic
<220> FEATURE:
<221> NAME/KEY: modified_base
<222> LOCATION: (13)..(37)
<223> OTHER INFORMATION: a, c, t, g, unknown or other
<220> FEATURE:
<221> NAME/KEY: modified_base
<222> LOCATION: (50)..(74)
<223> OTHER INFORMATION: a, c, t, g, unknown or other

<400> SEQUENCE: 90 ccccccccc ccnnnnnnnn nnnnnnnnnn nnnnnnntga taggaagttn nnnnnnnnnn      60
nnnnnnnnnn nnnn                                                       74

<210> SEQ ID NO 91
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(68)
<223> OTHER INFORMATION: Cyclic
<220> FEATURE:
<221> NAME/KEY: modified_base
<222> LOCATION: (7)..(31)
<223> OTHER INFORMATION: a, c, t, g, unknown or other
<220> FEATURE:
<221> NAME/KEY: modified_base
<222> LOCATION: (44)..(68)
<223> OTHER INFORMATION: a, c, t, g, unknown or other

<400> SEQUENCE: 91
tgatatnnnn nnnnnnnnnn nnnnnnnnnn nccccccccc ccnnnnnnnn nnnnnnnnnn      60 nnnnnnnn                                                              68

<210> SEQ ID NO 92
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(68)
<223> OTHER INFORMATION: Cyclic
<220> FEATURE:
<221> NAME/KEY: modified_base
<222> LOCATION: (7)..(31)
<223> OTHER INFORMATION: a, c, t, g, unknown or other
<220> FEATURE:
<221> NAME/KEY: modified_base
<222> LOCATION: (44)..(68)
<223> OTHER INFORMATION: a, c, t, g, unknown or other

<400> SEQUENCE: 92
tgatatnnnn nnnnnnnnnn nnnnnnnnnn nccataggaa gcnnnnnnnn nnnnnnnnnn      60 nnnnnnnn                                                              68
```

CONCATEMERIC RNA MOLECULES, COMPOSITIONS, AND METHODS AND USES THEREOF

CROSS-REFERENCE TO RELATED APPLICATIONS

This application is a national stage filing under 35 U.S.C. § 371 of PCT/US16/067233, filed Dec. 16, 2016, which claims priority to U.S. Provisional Application No. 62/269,249, filed Dec. 18, 2015. The entire contents of these applications are incorporated herein by reference in their entirety.

GOVERNMENT SUPPORT

This invention was made with Government support under Grant No. W81XWH-13-1-0151 awarded by U.S. Army Medical Research and Material Command, and under grant no. NIBIB 1F32EB017614-02 awarded by the National Institute of Health. The Government has certain rights in the invention.

MATERIAL SUBMITTED ELECTRONICALLY

The instant application contains a Sequence Listing which has been submitted in ASCII format via EFS-Web and is hereby incorporated by reference in its entirety. Said ASCII copy, created on Mar. 9, 2017, is named MTU27625_SL and is 27.2 KB in size.

BACKGROUND OF THE INVENTION

Since its discovery several decades ago, RNA interference (RNAi) has emerged as a potent tool for silencing therapeutic targets in many diseases. In particular, siRNAs have been extensively explored as gene silencing drugs, but their instability, low valence, and high stiffness have made efficient delivery difficult. To make siRNA more amenable to stable complexation, several groups have synthesized concatemeric siRNA, csiRNA, using strategies such as sticky overhangs and chemical crosslinking. With its higher molecular weight, valence, and flexibility compared to siRNA, csiRNA can potentially form more stable complexes than siRNA with smaller amounts of cationic polymer or lipid materials. Despite these advantageous properties, csiRNA must be delivered at doses that trigger innate immune responses and cytotoxicity in cancer cells in order to induce observable levels of specific gene silencing. To fully exploit both csiRNA's immunostimulatory and gene silencing capabilities in cancer cells for higher therapeutic potency, novel RNA molecules are needed to improve silencing efficiency.

SUMMARY OF THE INVENTION

Provided herein are concatemeric RNA molecules with greatly enhanced Dicer processing efficiency and silencing potency. The silencing activity of these novel RNA molecules far exceeds that of current RNAi molecules, and surpasses or equals that of siRNA, with greater levels of knockdown and prolonged, sustained silencing activity in vitro. The large molecular weight and improved efficacy of the concatemeric RNA molecules provided herein can remedy current siRNA delivery challenges of in vivo instability and dose-limiting toxicity.

One aspect of the invention relates to a concatemeric RNA molecule, comprising at least a first and a second repeat units, each of the first and the second repeat units including a first segment having a first nucleotide sequence, a second segment having a second nucleotide sequence, complementary to the first nucleotide sequence, and a connecting segment covalently attached to the second segment, wherein the connecting segment of the first repeat unit is covalently attached to the first segment of the second repeat unit.

Another aspect of the invention relates to a method for generating a concatemeric RNA molecule. The method comprises (a) providing a DNA template, and (b) transcribing said DNA template by rolling circle transcription (RCT) or rolling circle amplification (RCA) under appropriate conditions to yield a plurality of concatemeric RNA molecules. The RNA molecule comprises at least a first and a second repeat units, each of the first and the second repeat units includes a first segment having a first nucleotide sequence, a second segment having a second nucleotide sequence, complementary to the first nucleotide sequence, a connecting segment covalently attached to the second segment, wherein the connecting segment of the first repeat unit is covalently attached to the first segment of the second repeat unit; and a loop segment having a loop nucleotide sequence, the loop segment being covalently attached to the first and the second segments, wherein the loop nucleotide sequence includes at least one enzyme-specific nucleotide sequence. The method further includes (c) isolating the plurality of concatemeric RNA molecules.

Further scope of the applicability of the present invention will become apparent from the detailed description given hereinafter. However, it should be understood that the detailed description and specific examples, while indicating preferable embodiments of the invention, are given by way of illustration only, since various will become apparent to those skilled in the art from this detailed description.

BRIEF DESCRIPTION OF FIGURES

The present invention will become more fully understood from the detailed description given herein below and the accompanying drawings which are given by way of illustration only, and thus are not limitative of the present invention, and wherein:

FIG. 2, Panel (B) is a graph showing a response surface model of RNA yield from RCT as a function of template, NTP, and T7 RNA polymerase concentrations. RNA yield increased linearly as a function of template and polymerase concentrations, but showed a second order response to NTP concentration, with a maximum yield at ≈7 mM total NTPs. FIG. 2, Panel (C) is a schematic representation showing that rolling circle transcription was carried out from a series of DNA templates with variable loop sizes. The red x indicates that no RCT occurred from the template with two 5-base loops; green circles indicate RCT yield increased as a function of loop size for loops>5 bases. FIG. 2, Panel (D) is a photograph that depicts denaturing agarose gel electrophoresis (1.5%, MOPS, 7% formaldehyde) of RCT reaction products obtained from the templates with 8-base, 10-base, and 12-base loops (templates 4, 6, and 11). FIG. 2, Panel (E) is a graph showing the size distributions with corresponding number avg. molecular weight ($M_n$), weight avg. molecular weight ($M_w$), and PDI, calculated from the gel in FIG. 2, Panel (D). FIG. 2, Panel (F) is a graph showing Quant-iT Ribogreen quantification of the RNA yield from the different dumbbell templates. Yields are reported as the mean with s.d. for two independent reactions.

FIG. 3, Panel (C) is a photograph of a gel depicting the results of p-shRNAs with 21 or 25 bp stems (from templates 6 and 12, respectively) treated with RNase I for 15 min then run on a native 15% TBE-PAGE gel. The observed banding pattern confirms the predicted alternating single-/double-stranded structure of p-shRNA. FIG. 3, Panels (D) and (E) is a photograph of a gel depicting the results of p-shRNA (21 bp stem/10 base loops; from template 6) and siRNA (21 bp) treated with 50% human serum for 0.1-24 h and run on a native 15% TBE-PAGE gel (SB indicates background serum band). Ladders=dsRNA ladder (NEB) and siRNA marker (NEB).

FIG. 4, Panel (C) is a graphic depicting a side view of a 3D model based on the predicted MFE structure of p-shRNA (5 repeats). Co-transcriptional and MFE secondary structures were predicted using CoFold and RNAFold, respectively. 3D models were generated using RNAComposer and rendered with PyMol.

FIG. 5, Panel (B) are schematic diagram and native PAGE gel (15% TBE) depicting T1 digest of p-shRNA derived from template 6 (one C in both loops). The gel shows a single prominent band at ~30 bp following the T1 digest, corresponding to a knicked single hairpin unit of p-shRNA. Ladders=dsRNA ladder (NEB).

FIG. 6, Panel (B) is a bar graph depicting $IC_{50}$ values±95% C.I. (based on 3 parameter log-logistic model) calculated from viability curves for cell lines treated with p-shRNA (I=p-shRNA-21, II=p-shRNA-25; derived from templates 17 and 18) or HMW poly-I:C complexed with Lipofectamine. FIG. 6, Panel (C) is a graph depicting a cell viability dose-response curves for p-shRNA-25 and poly-I:C delivered with either Lipofectamine or TransIT-X2 to SKOV3 cells. FIG. 6, Panel (D) is a bar graph depicting caspase activation measured using CaspaseGlo luminescence assays 14 h after treating SKOV3 cells with p-shRNA-25- or poly-I:C-Lipofectamine complexes at 300 ng/mL. Values correspond to the means of three biological replicates (±s.e.m.). FIG. 6, Panel (E) is a bar graph depicting mean GFP expression determined by flow cytometry was measured in HeLa cells 72 h following transfection with 10 nM p-shRNA (p-shGFP-21 or p-shLUC-21) complexed with TransIT-X2. Values were derived from mean fluorescence and correspond to the mean of three biological replicates (±s.e.m.) relative to untreated cells. FIG. 6, Panel (F) is a bar graph depicting luciferase expression was measured as bioluminescence normalized to total protein in SKOV3 and UCI101 cells following treatment with 15 nM p-shRNA complexed with TransIT-X2 (p-shLUC and p-shGFP used in this experiment were synthesized from templates 19 and 20). Values are presented as means for three biological replicates (±s.e.m.) relative to untreated cells. For all graphs: $p<0.05$ (*), $p<0.01$(), $p<0.001$(*).

FIG. 7, Panel (B) are photographs of fluorescence imaging of SKOV3 cells stained with anti-NF-κB (red) and DAPI (green). Poly-I:C and p-shRNA were complexed with Lipofectamine and incubated with cells at the indicated concentrations for 1 h prior to fixation and staining. The yellow color in the merged images indicates nuclear localization of NF-κB. FIG. 7, Panels (C) and (D) are graphs depicting nuclear localization of NF-κB quantified using Cell Profiler by taking the ratio of median NF-κB fluorescence in the nucleus divided by median NF-κB fluorescence in the cytoplasm for untreated cells or cells treated with 150 or 600 ng/mL RNA/Lipofectamine complexes (for histograms of samples treated with 150 ng/mL see Figure S11). Values in FIG. 7, Panel (D) correspond to the geometric means of the histograms±95% confidence intervals.

FIG. 11, Panel (B) is a bar graph depicting RCT reaction yields measured by Quant-IT Ribogreen® (mean+s.e.m. for 3 reactions).

FIG. 11, Panel (C) is a photograph of a gel showing a serum only control lane with dsRNA ladder and untreated p-shRNA for reference.

FIG. 15, Panel (A) shows a photograph of the native PAGE (15% TBE) gel. FIG. 15, Panel (B) shows a photograph of the denaturing PAGE (15% TBE-Urea) gel.

FIG. 17, Panel (A) is a bar graph depicting the results of GFP silencing by p-shRNA delivered with Lipofectamine 2000. FIG. 17, Panels (B) and (C) are bar graphs depicting the results of a comparison of silencing by 21 bp (from template 6) and 25 bp p-shRNA (from template 12), delivered with TransIT-X2 (Panel (B)) or Lipofectamine 2000 (Panel (C)). Samples were all normalized to the mean fluorescence of untreated cells and represent the mean of three biological replicates s.e.m. $P<0.05$ (*), $P<0.01$ (), $P<0.001$ (*)

FIG. 21, Panel (b) is a photograph that depicts the results of an analysis of RNase T1 digestion (one hour at 37° C.) of p-shRNA synthesized from the template in a (p-sh25) by 15% native polyacrylamide gel electrophoresis (PAGE). FIG. 21, Panel (c) is a photograph that depicts the results of analysis of RNase T1 digestion (one hour at 37° C.) of p-sh25, compared to a standard 63 nt RNA of the same sequence as the predicted product, by 15% denaturing PAGE.

FIG. 22, Panel (b) is a schematic representation of the DNA templates with varying loop sizes and sequences. Green circles indicate loops at which T7 RNA polymerase initiates transcription. FIG. 22, Panel (c) is a photograph that depicts the results of an analysis of p-shRNA structures generated from templates in Panel (a), before and after RNase T1 treatment for one hour at 37° C., by 15% native polyacrylamide gel electrophoresis, with the main RNase T1 digestion products depicted.

FIG. 24, Panel (c) is a bar graph showing the results of GFP knockdown in HeLa-GFP cells by op-shRNAs with 21, 25, 27, and 29 bp stems, using TransIT-X2®. FIG. 24, Panel (d) is a graph showing knockdown duration of op-sh25 and siRNA (5 nM) with TransIT-X2® in HeLa-GFP cells. FIG. 24, Panels (e) and (f) are bar graphs showing the results of luciferase knockdown in luciferase-expressing SKOV3 (Panel (e)) and UCI101 (Panel (f)) cells by luciferase-targeting and scr p-sh25, op-sh25, and siRNA (5 nM) with TransIT-X2®. Results are presented as mean±SEM, n=3. *p<0.05, ***p<0.0001.

FIG. 25, Panels (b) and (c) are photographs that depict the results of agarose gel shift assays of op-shRNA (Panel (b)) and siRNA (Panel (c)) complexed with 2 kDa branched polyethyleneimine (PEI) at increasing N/P ratios. FIG. 25, Panels (d) and (e) are bar graphs showing the results of dynamic light scattering measurements of the hydrodynamic diameters (Panel (d)) and zeta potentials (Panel (e)) of op-shRNA and siRNA complexes formed with 2 kDa branched PEI. Results are presented as mean±SEM, n=3. FIG. 25, Panels (f) and (g) are photographs that depict the results of heparin displacement assays of op-shRNA (Panel (f)) and siRNA (Panel (g)) complexes with 2 kDa branched PEI formed at N/P 15, analyzed by agarose gel electrophoresis.

FIG. 26, Panel (b) is a photograph that depicts the results of analysis of RNase T1 digestion (one hour at 37° C.) of luciferase-targeting p-sh25, compared to a standard 63 nt shRNA (sequence listed in Table S2), by 15% denaturing PAGE. FIG. 26, Panel (c) is a bar graph depicting the results of quantification by Quant-IT Ribogreen® assay of RNA yields obtained from RCT of templates encoding GFP- and luciferase-targeting p-sh25. Results are presented as the mean±SEM of two independent RCT reactions.

DETAILED DESCRIPTION OF THE INVENTION

A. Abbreviations and Definitions

Figure 1:
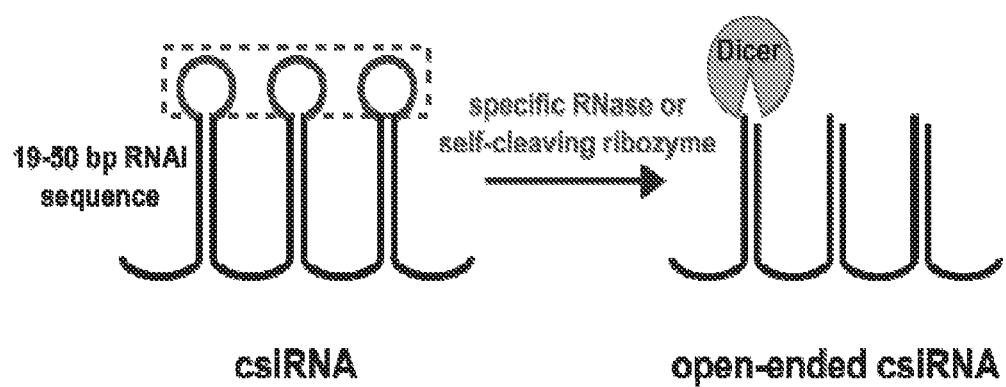
FIG. 1 is a schematic diagram showing an interconversion of a first example embodiment of the concatemeric RNA of the present invention and a second example embodiment of the concatemeric RNA the present invention by cleaving an enzyme-specific cleavage site in the loop segment.

As used herein the abbreviations:
"csiRNA" is equivalent to "p-shRNA"
"csi25" is equivalent to "p-sh25"
"open-ended csiRNA" is equivalent to "op-shRNA"
"T1-csi25" is equivalent to "op-sh25"

The term "concatemer," is used interchangeably with "periodic" and used herein in the context of nucleic acid molecules, refers to a nucleic acid molecule, such as a RNA molecule, that contains multiple copies of the same RNA sequences linked in a series. "Concatemeric" is the adjective describing such RNA molecules. For example, a concatemer comprising ten copies of a specific sequence of nucleotides (e.g., [XYZ].sub.10), would comprise ten copies of the same specific sequence linked to each other in series, e.g., 5'-XYZXYZXYZXYZXYZXYZXYZXYZXYZXYZ-3'. A concatemer may comprise any number of copies of the repeat unit or sequence, e.g., at least 2 copies, at least 3 copies, at least 4 copies, at least 5 copies, at least 10 copies, at least 100 copies, at least 1000 copies, etc. A concatemer may be a linear nucleic acid molecule, or may be circular.

The term "enzyme," as used herein, refers to an protein, for example a RNase or a ribozyme, capable of cleaving a phosphodiester bond connecting nucleotide residues in a nucleic acid molecule. In some embodiments, an enzyme is a RNase or ribozyme, e.g., an enzyme that can bind a nucleic acid molecule and cleave a phosphodiester bond connecting nucleotide residues within the nucleic acid molecule. In some embodiments, an enzyme is a site-specific enzyme, binding and/or cleaving a specific phosphodiester bond within a specific nucleotide sequence, which is also referred to herein as the "recognition sequence," the "enzyme target site," or the "enzyme-specific nucleotide sequence." In some embodiments, the enzyme is RNase T1, which cleaves the 3' end of unpaired Guanines. In some embodiments, the enzyme is RNase T2, which cleaves all four unpaired residue but preferentially cleaves the 3' end of Adenines. In some embodiments, the enzyme is RNase U2, which cleaves the 3' end of unpaired Adenines. In some embodiments, the enzyme is RNase A, which cleaves the 3' end of unpaired Cytosines and Uracils. In some embodiments, the enzyme-specific nucleotide sequence is a self-cleaving ribozyme sequence. In some embodiments, an enzyme recognizes a single stranded target site, while in other embodiments, an enzyme recognizes a double-stranded target site, for example a double-stranded DNA-RNA target site. For example, RNase H cleaves the 3'-O—P bond of RNA in a DNA/RNA duplex substrate to produce 3'-hydroxyl and 5'-phosphate terminated products.

Unpaired nucleotides at the end of a double-stranded DNA or RNA molecule are referred to as "overhangs," e.g., as "5'-overhang" or as "3'-overhang," depending on whether the unpaired nucleotide(s) form(s) the 5' or the 3' end of the respective DNA or RNA strand. Double-stranded DNA or RNA molecule ends ending with unpaired nucleotide(s) are also referred to as sticky ends, as they can "stick to" other double-stranded DNA molecule ends comprising complementary unpaired nucleotide(s).

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA molecules, single and/or double-stranded RNA. Nucleic acids may be a non-naturally occurring molecule, e.g., a recombinant or synthetic DNA, RNA, or DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone.

Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages). In some embodiments, nucleic acids include phosphodiester backbone linkages; alternatively or additionally, in some embodiments, nucleic acids include one or more non-phosphodiester backbone linkages such as, for example, phosphorothioates and 5'-N-phosphoramidite linkages.

The term "silencing sequence," refers to a sequence within a nucleic acid molecule that is targeted by RNAi. In some embodiments, the silencing sequence comprises a RNAi target sequence that silences a human gene. In some embodiments, the silencing sequence comprises a RNAi target sequence that silences a non-human gene.

The term "treat" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition in a subject in need thereof. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease, disorder, or condition of interest (e.g., cancer, infection, etc).

The phrase "rolling circle amplification" (RCA) and/or "rolling circle transcription" (RCT) refers to a methodology for production of concatemeric RNA molecules for use herein. Exemplary RCA strategies include, for example, single-primer initiated RCA and by various two-primer amplification methods such as ramification amplification (RAM), hyperbranched RCA, cascade RCA, and exponential RCA. In certain embodiments, RNA-containing molecules can be produced via rolling circle transcription (RCT). RCA/RCT may be particularly useful for production of long nucleic acid molecules, and/or furthermore may generate nucleic acid molecules. Those skilled in the art will appreciate that a nucleic acid molecule produced by RCA/RCT will typically have a nucleotide sequence comprising or consisting of multiple copies of the complement of the circular template being amplified.

More details of RCA can be found in US Patent Application No. 2010/0189794, the contents of which are incorporated herein by reference. Features of the compositions and methods described in the application may be applied in various combinations in the embodiments described herein. In some embodiments, a first single-stranded nucleic acid molecule is formed by RCA. In some embodiments, the first single-stranded nucleic acid molecule is formed with the aid of a first primer and a nucleic acid polymerase. In some embodiments, a second single-stranded nucleic acid molecule is formed by amplifying the first single-stranded nucleic acid with the aid of a second primer and a polymerase. In some embodiments, a third single-stranded nucleic acid molecule is formed by amplifying the second single-stranded nucleic acid molecule with the aid of a third primer and a polymerase.

A RCA can be repeated with as many primers as desired, e.g., 4, 5, 6, 7, 8, 9, 10 or more primers can be used. In some embodiments, a plurality of primers can be added to templates to form nucleic acid molecules, wherein the plurality can comprise at least about 2, 3, 4, 5, 6, 7, 8, 9, 10, 15, 20, 25, 30, 35, 40, 45, 50, 55, 60, 65, 70, 75, 80, 85, 90, 95, or 100 primers. In some embodiments, more than 100 primers are used. In some embodiments, random fragments of short nucleic acid fragments, e.g., comprising digested or otherwise degraded DNAs, are used as non-specific primers to prime the formation of nucleic acid molecules using rolling circle amplification. As described herein and will be appreciated by those of skill in the art, polymerization reaction conditions can be adjusted as desired to form nucleic acid molecules and self-assembled particles. For example, reaction conditions that favor stringent nucleic acid hybridization, e.g., high temperature, can be used to favor more specific primer binding during amplification.

The phrase "dumbbell template" or "dumbbell-shaped template" refers to a nucleotide template used for RCA/RCT as described herein is or comprises deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA). The template may comprise nucleotide sequence that includes one or more coding sequences, one or more non-coding sequences, and/or combinations thereof. The template may comprise nucleotide sequence that includes one or more silencing sequences, directed to one or more human or non-human gene of interest. In some embodiments, the dumbbell template comprises a stem region, a first loop region, and a second loop region. In some embodiments, the stem region of the dumbbell comprises a double stranded nucleotide molecule containing 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, the first and second loop region contains 4, 5, 6, 7, 8, 9, 10, 11, 12, 13, 14, 15, 16, 17, 18, 19, or 20 nucleotides. In some embodiments, the first loop or second loop contains an enzyme cleavage site when transcribed. In some embodiments, the first loop of the DNA template contains an enzyme cleavage site and the second loop lacks the enzyme cleavage site contained in the first loop. When RCT/RCA is carried out with the aforementioned DNA template, the concatemeric RNA molecules contain an enzyme cleavage site in the loop segments, but the connecting segments lacks the enzyme cleavage site contained in the loop segments. Upon addition of an enzyme, cleavage occurs only at the enzyme cleavage site contained in the loop segment, whereas the connecting segments are left intact.

As used herein, an "effective amount" refers to an amount of a therapeutic agent or a combination of therapeutic agents that is therapeutically or prophylactically sufficient to treat the target disorder. An effective amount will depend on the age, gender, and weight of the patient, the current medical condition of the patient, and the nature of the esophageal cancer being treated. Those of skill in the art will be able to determine appropriate dosages depending on these and other factors.

As used herein, the term "subject" refers to a mammal, preferably a human, but can also mean an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The present invention, among other things, describes concatemeric RNA molecules, pharmaceutical compositions, particles, and methods and uses thereof.

B. Concatemeric RNA Molecule

Concatemeric RNA molecules are provided herein comprising at least a first and a second repeat units, each of the first and the second repeat units including: a first segment having a first nucleotide sequence; a second segment having a second nucleotide sequence, complementary to the first nucleotide sequence; and a connecting segment covalently attached to the second segment, wherein the connecting segment of the first repeat unit is covalently attached to the first segment of the second repeat unit. In some embodiments, the concatemeric RNA molecules may comprise one, two, three, four, five, six, seven, eight, nine, ten, fifteen, twenty, twenty-five, thirty, thirty-five, forty, forty-five, fifty, fifty-five, sixty, sixty-five, seventy, seventy-five, eighty, eighty-five, ninety, ninety-five, and one hundred repeat units. In some embodiments, the first segment and the second segment of at least one of the first or the second repeat units form a stem structure by non-covalent complementary nucleotide pairing of the first nucleotide sequence and the second nucleotide sequence.

In some embodiments, the first segment and the second segment of at least one of the first or the second repeat units are not covalently attached. In some embodiments, at least one of the first or the second repeat units further includes a loop segment having a loop nucleotide sequence, the loop segment being covalently attached to the first and the second segments, wherein the loop nucleotide sequence includes at least one enzyme-specific nucleotide sequence. In some embodiments, the first segment, the second segment, and the loop segment of at least one of the first or the second repeat units form a hairpin loop structure by non-covalent complementary nucleotide pairing of the first nucleotide sequence and the second nucleotide sequence.

In some embodiments, the enzyme is selected from the group consisting of RNAse T1, RNAse T2, RNase U2, RNase A, RNase H, and ribozyme. In some embodiments, the enzyme-specific nucleotide sequence is a self-cleaving ribozyme sequence. In some embodiments, the connecting segment contains 4 nucleotides to 20 nucleotides. In some embodiments, the connecting segment contains 4, 5, 6, 7, 8, 9, 10, 11, 12, 13, 14, 15, 16, 17, 18, 19, or 20 nucleotides. In some embodiments, the connecting segment contains 6 nucleotides or 12 nucleotides. In some embodiments, the loop segment contains 4 nucleotides to 20 nucleotides. Upon cleavage, each open end may contain overhangs, up to the number of nucleotides in the original loop segment. In some embodiments, the loop segment contains 4, 5, 6, 7, 8, 9, 10, 11, 12, 13, 14, 15, 16, 17, 18, 19, or 20 nucleotides. In some embodiments, the loop segment contains 6 nucleotides or 12 nucleotides. Certain concatemeric RNA molecules are designed such that the loop segment to be cleaved contain one or more of the nucleotides that the RNase specifically cuts, and the connecting segments do not contain that nucleotide. In some embodiments, the connecting or loop segment comprises the nucleic acid sequences set forth in SEQ ID NOs: 1-7. Such sequences may be digested by RNase T1.

5'-GGUCAG-3'; (SEQ ID NO: 1)

5'-AACUUCCUAUCA-3'; (SEQ ID NO: 2)

5'-AAGAAA-3'; (SEQ ID NO: 3)

5'-GGGGGGGGGGGG-3'; (SEQ ID NO: 4)

5'-AUAUCA-3'; (SEQ ID NO: 5)

5'-GGCUUCCUAUGG-3'; and (SEQ ID NO: 6)

5'-GGGGGG-3'. (SEQ ID NO: 7)

In some embodiments, the connecting or loop segment comprises the nucleic acid sequences set forth in SEQ ID NOs: 8-10. Such sequences may be digested by RNase T2.

5'-AAAAAA-3'; (SEQ ID NO: 8)

5'-CCACCC-3'; and (SEQ ID NO: 9)

5'-ACUUCCUGGCCA-3'. (SEQ ID NO: 10)

In some embodiments, the connecting or loop segment comprises the nucleic acid sequences set forth in SEQ ID NOs: 11-14. Such sequences may be digested by RNase U2.

5'-AAAAAA-3'; (SEQ ID NO: 11)

5'-AAAGGG-3'; (SEQ ID NO: 12)

5'-CCACCC-3'; and (SEQ ID NO: 13)

5'-ACUUCCUGGCCA-3'. (SEQ ID NO: 14)

In some embodiments, the connecting or loop segment comprises the nucleic acid sequences set forth in SEQ ID NOs: 15-18. Such sequences may be digested by RNase A.

5'-CCCCCC-3'; (SEQ ID NO: 15)

5'-UUUUUU-3'; (SEQ ID NO: 16)

5'-CUUCUU-3'; and (SEQ ID NO: 17)

5'-CGUUACU-3'. (SEQ ID NO: 18)

In some embodiments, the connecting or loop segment comprises the nucleic acid sequence set forth in SEQ ID NO: 19. Such sequences may be digested by Ribozyme. 5'-CGCGGCAUUAAUGCAGCUUUAUUGCC-3' (SEQ ID NO: 19).

In some embodiments, the nucleic acid sequences set forth in SEQ ID NOs: 1-7 may comprise substitutions and additions such that the sequences can be cleaved by RNAse T2, RNase U2, RNase A, RNase H, and ribozyme. A substitution may comprise the replacement of one or more nucleotides by different nucleotides, respectively, as compared to a nucleotide sequence of a parental fragment thereof. In some embodiments, the first and second segment form a double stranded stem segment comprising anti-sense and sense strands containing 19 nucleotides to 50 nucleotides. In some embodiments, the stem segment may comprise 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, the first and second segment comprises a Drosha recognized cleavage site and a Dicer recognized cleavage site. In some embodiments, the Drosha recognized cleavage site and the Dicer recognized cleavage site may be spaced and connected by the silencing sequence.

In some embodiments, the first and second segment comprise a silencing sequence. In some embodiments, the silencing sequence comprises an RNAi target sequence. In some embodiments, the RNAi target sequence comprises antisense and sense strands ranging from 19 to 50 base pairs, with or without base pair mismatches for improved RCT yield. In some embodiments, the RNAi target sequence silences any human or non-human gene associated with a particular disease, disorder, or condition of interest (e.g., cancer, infection, neurological disorder, metabolic disease, inflammation, etc). Other diseases include, but not limited to, persistent infectious disease, proliferative diseases, neurodegenerative diseases, cancers, psychological diseases, metabolic diseases, autoimmune diseases, sexually transmitted diseases, gastro-intestinal diseases, pulmonary diseases, cardiovascular diseases, stress- and fatigue-related disorders, fungal diseases, pathogenic diseases, obesity-related disorders, viral infections, bacterial infections, or biomarkers regarding same. Viral infectious diseases including human papilloma virus (HPV), hepatitis A Virus (HAV), hepatitis B Virus (HBV), hepatitis C Virus (HCV), retroviruses such as human immunodeficiency virus (HIV-1 and HIV-2), herpes viruses such as Epstein Barr Virus (EBV), cytomegalovirus (CMV), HSV-1 and HSV-2, influenza virus, Hepatitis A and B, FIV, lentiviruses, pestiviruses, West Nile Virus, measles, smallpox, cowpox, ebola, coronavirus, retrovirus, herpesvirus, potato S virus, simian Virus 40 (SV40), Mouse Mammary Tumor Virus (MMTV) promoter, Moloney virus, ALV, Cytomegalovirus (CMV), Epstein Barr Virus (EBV), or Rous Sarcoma Virus (RSV). The aptamers of the present invention may detect antigens, antibodies, or other analytes associated with pathogens such as various parasites, like malaria. In addition, bacterial, fungal and other pathogenic diseases are included, such as *Aspergillus, Brugia, Candida, Chikungunya, Chlamydia, Coccidia, Cryptococcus, Dengue, Dirofilaria, Gonococcus, Histoplasma, Leishmania, Mycobacterium, Mycoplasma, Paramecium, Pertussis, Plasmodium, Pneumococcus, Pneumocystis, P. vivax* in Anopheles mosquito vectors, *Rickettsia, Salmonella, Shigella, Staphylococcus, Streptococcus, Toxoplasma* and *Vibriocholerae*. Exemplary species include *Neisseria gonorrhea, Mycobacterium tuberculosis, Candida albicans, Candida tropicalis, Trichomonas vaginalis, Haemophilus vaginalis,* Group B *Streptococcus* sp., *Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis, Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Clostridium tetani, Clostridium botulinum;* or, a fungus, such as, e.g., *Paracoccidioides brasiliensis;* or other pathogen, e.g., *Plasmodium falciparum.* Also included are National Institute of Allergy and Infectious Diseases (NIAID) priority pathogens. These include Category A agents, such as variola major (smallpox), *Bacillus anthraces* (anthrax), *Yersinia pestis* (plague), *Clostridium botulinum* toxin (botulism), *Francisella tularensis* (tularaemia), filoviruses (Ebola hemorrhagic fever, Marburg hemorrhagic fever), arenaviruses (Lassa (Lassa fever), Junin (Argentine hemorrhagic fever) and related viruses); Category B agents, such as *Coxiella burnetti* (Q fever), *Brucella* species (brucellosis), *Burkholderia mallei* (glanders), alphaviruses (Venezuelan encephalomyelitis, eastern & western equine encephalomyelitis), ricin toxin from *Ricinus communis* (castor beans), epsilon toxin of *Clostridium perfringens; Staphylococcus* enterotoxin B, *Salmonella* species, *Shigella dysenteriae, Escherichia coli* strain O157:H7, *Vibrio cholerae, Cryptosporidium parvum;* Category C agents, such as nipah virus, hantaviruses, yellow fever in Aedes mosquitoes, and multidrug-resistant tuberculosis; helminths, such as *Schistosoma* and *Taenia;* and protozoa, such as *Leishmania* (e.g., *L. mexicana*) in sand flies, *Plasmodium,* Chagas disease in assassin bugs.

Bacterial pathogens include, but are not limited to, such as bacterial pathogenic gram-positive cocci, which include but are not limited to: pneumococci; staphylococci; and streptococci. Pathogenic gram-negative cocci include: meningococci; and gonococci. Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirilum; listeria monocytogenes; erysipelothrix rhusiopathiae; diphtheria; cholera; anthrax; and donovanosis (granuloma inguinale). Pathogenic anaerobic bacteria include; tetanus; botulism; other clostridia; tuberculosis; leprosy; and other mycobacteria. Pathogenic spirochetal diseases include: syphilis; treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis. Rickettsial infections include rickettsial and rickettsioses. Examples of mycoplasma and chlamydial infections include: mycoplasma pneumoniae; lymphogranuloma venereum; psittacosis; and perinatal chlamydial infections. Pathogenic protozoans and helminths and infections eukaryotes thereby include: amebiasis; malaria; leishmaniasis; trypanosomiasis; toxoplasmosis; pneumocystis carinii; giardiasis; trichinosis; filariasis; schistosomiasis; nematodes; trematodes or flukes; and cestode (tapeworm) infections.

The term "cancer" as used herein refers to an abnormal growth of cells which tend to proliferate in an uncontrolled way and, in some cases, to metastasize (spread). The types of cancer include, but is not limited to, solid tumors (such as those of the bladder, bowel, brain, breast, endometrium, heart, kidney, lung, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Additional non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, lung cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, Wilms tumor.

In some embodiments, the gene can be, but not limited to, to brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone morphogenetic protein 2 (BMP2), BRAK, C-10, Cardiotrophin 1 (CT1), other chemokines, interleukins and combinations thereof.

Upon cleavage of the enzyme-specific nucleotide sequence by an RNase selected from the group consisting of RNAse T1, RNAse T2, RNase U2, RNase A, RNase H, and ribozyme, the concatemeric RNA molecule has enhanced properties. Such enhanced properties include, but not limited to, enhanced Dicer processing efficiency, enhanced target knockdown capabilities, enhanced silencing activity, improved stability, and decreased toxicity when introduced into a cell or subject in need thereof. The enzyme Dicer cuts double-stranded RNA molecule into approximately 21-nt RNA duplexes in the cytoplasm, where it can be converted to siRNA by the RNA-induced silencing complex (RISC) for gene silencing. The enhanced Dicer processing efficiency can be measured as an increased percent conversion of the concatemeric RNA molecules into siRNA fragments. The increased percent conversion may comprise about 70%, 75%, 80%, 85%, 80%, 85%, 90%, 95%, 96%, 97%, 98%, or 99% conversion of the concatemeric RNA molecules into siRNA fragments. The enhanced target knockdown can be measured as an increased percent knockdown of a RNAi target sequence of about 70%, 75%, 80%, 85%, 80%, 85%, 90%, 95%, 96%, 97%, 98%, or 99% knockdown of the human or non-human gene. The enhanced silencing activity can be measured as an sustained or prolonged silencing duration or time period of the concatemeric RNA molecules of up to 2, 3, 4, 5, 6, 7, 8, 9, 10, 11, 12, 13, 14, or 15 days.

The present invention encompasses the recognition that the concatemeric RNA molecules can be designed and/or prepared to simultaneously deliver to a target site (e.g., to a cancer cell) a plurality of different nucleic acid agents (e.g., siRNAs), each of which is directed to a different specific molecular target of interest.

C. Pharmaceutical Compositions

In certain aspects, provided herein are pharmaceutical compositions comprising a concatemeric RNA molecule, as described above. In some embodiments, the composition comprises a pharmaceutically acceptable carrier. In some embodiments, the composition includes a combination of multiple (e.g., two or more) concatemeric RNA molecules.

The pharmaceutical compositions disclosed herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; or (2) parenteral administration, for example, by subcutaneous, intramuscular, intravenous or epidural injection as, for example, a sterile solution or suspension, or sustained-release formulation.

Methods of preparing these formulations or compositions include the step of bringing into association any of the concatemeric RNA molecules described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions suitable for parenteral administration comprise any of the concatemeric RNA molecules described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such ethyl oleate. Proper fluidity can be maintained, for example, by the use of coating materials, such as lecithin, by the maintenance of the required particle size in the case of dispersions, and by the use of surfactants.

Regardless of the route of administration selected, the agents provided herein, which may be used in a suitable hydrated form, and/or the pharmaceutical compositions disclosed herein, are formulated into pharmaceutically-acceptable dosage forms by conventional methods known to those of skill in the art.

In some embodiments, the pharmaceutical composition described herein, when administered to a subject, can be useful for silencing genes particular to any of the aforementioned diseases, disorders, and conditions. Said pharmaceutical compositions can be useful for the prophylactic and/or therapeutic treatment of these diseases, disorders, and conditions.

D. Particles

In certain aspects, provided herein are particles comprising the concatemeric RNA molecules of the present invention. Said particles can contain a particle core, which can optionally be coated by a film. Upon coating, a particle can be converted from a first configuration to a second configuration. In some embodiments, the greatest dimension of a particle (in its first or second configuration) may be greater or less than 5 µm, 2 µm, 1 µm, 800 nm, 500 nm, 200 nm, 100 nm, 90 nm, 80 nm, 70 nm, 60 nm, 50 nm, 40 nm, 30 nm, 20 nm, 10 nm, or even 5 nm. In some embodiments, the greatest dimension a particle (in its first or second configuration) may be in a range of any two values above. In some embodiments, a particle in a first configuration has the greatest dimension in a range of about 5 µm to about 2 µm or about 2 µm to about 1 .mu.m. In some embodiments, a particle in a second configuration has the greatest dimension in may be in a range of about 500 nm to about 200 nm, about 200 nm to about 100 nm or about 100 nm to about 50 nm. In some embodiments, a particle can be substantially spherical. In some embodiments, the dimension of a particle is a diameter, wherein the diameter can be in a range as mentioned above.

In various embodiments, a particle described herein can comprise a particle core, a coating film (including one or more layers; in some embodiments one or more polyelectrolyte layers), and one or more agents such as diagnostic, therapeutic and/or targeting agents.

i. Nucleic Acid-Containing Core

A particle core can consist of or include one or more nucleic acid molecules. In some embodiments, a core is comprised of a plurality of nucleic acid molecules. Individual nucleic acid molecules within a core can have different nucleic acid sequences or substantially the same nucleic acid sequence. In some embodiments, nucleic acid molecule(s) within a core have sequences that share at least one common sequence element.

In some embodiments, at least one nucleic acid molecule in a core has a nucleotide sequence that comprises multiple copies of at least a first sequence element. In some embodiments, at least one nucleic acid molecule in a core has a nucleotide sequence that comprises multiple copies of each of at least a first and a second sequence element. In some embodiments, at least one nucleic acid molecule has a nucleotide sequence that comprises alternating copies of the first and second sequence elements. In some embodiments, at least one nucleic acid molecule has a nucleotide sequence that comprises multiple copies of each of three or more sequence elements.

In some embodiments, at least one nucleic acid molecule has a nucleotide sequence that includes one or more sequence elements found in a natural source. In some embodiments, at least one nucleic acid molecule has a nucleotide sequence that includes a first sequence element that is found in a first natural source and a second sequence element that is found in a second natural source. The first and second natural sources can be the same or difference.

In some embodiments, at least one nucleic acid molecule has a nucleotide sequence that represents an assemblage of sequence elements found in one or more source nucleic acid molecules. In some embodiments, at least one nucleic acid molecule has a nucleotide sequence that represents an assemblage of at least two different sequence elements found in two different source nucleic acid molecules.

In some embodiments, nucleic acid molecule(s) within a core have nucleotide sequences that fold into higher order structures (e.g., double and/or triple-stranded structures). In some embodiments, nucleic acid molecule(s) within a core have nucleotide sequences that comprise two or more complementary elements. In some embodiments, such complementary elements can form one or more (optionally alternative) stem-loop (e.g., hairpin) structures. In some embodiments, nucleic acid molecule(s) within a core have nucleotide sequences that include one or more portions that remain single stranded (i.e., do not pair intra- or intermolecularly with other core nucleic acid sequence elements).

In some embodiments, at least one nucleic acid molecules in a core contains at least one cleavage site. In some embodiments, a cleavage site is a bond or location susceptible to cleavage by a cleaving agent such as a chemical, an enzyme (e.g., nuclease, dicer, DNAase and RNAase), radiation, temperature, etc. In some embodiments, the cleaving agent is a sequence specific cleaving agent in that it selectively cleaves nucleic acid molecules at a particular site or sequence.

In some embodiments, at least one nucleic acid molecules in a core contains at least one cleavage site susceptible to cleavage after delivery or localization of a particle as described herein to a target site of interest. In some embodiment, nucleic acid molecule(s) in a core have a plurality of cleavage sites and/or are otherwise arranged and constructed so that multiple copies of a particular nucleic acid of interest are released at the target site, upon delivery of a particle as described herein.

In some embodiments, nucleic acid molecule(s) within a core have a self-assembled structure and/or are characterized by an ability to self-assemble in that it/they fold(s) into a stable three-dimensional structure, typically including one or more non-covalent interactions that occur between or among different moieties within the nucleic acid, without requiring assistance of non-nucleic acid entities. In some embodiments, nucleic acid molecule(s) within a core are arranged in a crystalline structure comprising lamellar sheets. In some embodiments, a core comprises or consists of one or more entangled nucleic acid molecules.

In some embodiments, nucleic acid molecule(s) in a core have a molecular weight greater than about $1 \times 10^{10}$ g/mol, about $1 \times 10^{9}$ g/mol, about $1 \times 10^{8}$ g/mol, about $1 \times 10^{7}$ g/mol, about $1 \times 10^{6}$ g/mol, or about $1 \times 10^{5}$ g/mol.

As described herein, in some embodiments, nucleic acid molecule(s) in a core includes multiple copies of at least one sequence element (e.g., concatenated in one or more long nucleic acid molecules whose sequence comprises or consists of multiple copies of the sequence element, and/or as discrete nucleic acid molecules each of which has a sequence that comprises or consists of the element, or a combination of both) whose length is within the range between a lower length of at least 5, 10, 15, 20, 25, 30, 35, 40, 45, or more and an upper length of not more than 10000, 9000, 8000, 7000, 6000, 5000, 4000, 3000, 2000, 1000, 900, 800, 700, 600, 500, 400, 300, 200, 100, 90, 80, 70, 60, 50, 40, 30 or less, wherein the upper length is greater than the lower length.

Particles described herein are characterized by a high loading of nucleic acids. In some embodiments, a particle core comprises at least about $1 \times 10^3$, about $1 \times 10^4$, about $1 \times 10^5$, about $1 \times 10^6$, about $1 \times 10^7$, about $1 \times 10^8$, about $1 \times 10^9$, or about $1 \times 10^{10}$ copies of a particular sequence element of interests. In some embodiments, a particle core comprises copies of a particular sequence element of interests in a range of about $1 \times 10^3$ to about $1 \times 10^4$, about $1 \times 10^4$ to about $1 \times 10^5$, about $1 \times 10^5$ to about $1 \times 10^6$, about $1 \times 10^6$ to about $1 \times 10^7$, about $1 \times 10^7$ to about $11 \times 10^8$, about $11 \times 10^8$ to about $11 \times 10^9$, or about $11 \times 10^9$ to about $11 \times 10^{10}$. In some embodiments, a particle core comprises copies of a particular sequence element of interests in a range of about $1 \times 10^3$ to about $1 \times 10^{10}$, about $1 \times 10^4$ to about $1 \times 10^8$ or about $1 \times 10^5$ to about $1 \times 10^7$. In some embodiments, a particle core comprises copies of a particular sequence element of interests in a range of any two values above.

ii. Coating Films

Particles provided by the present invention may include a coating film on a nucleic acid-containing core. In some embodiments, a film substantially covers at least one surface of a particle core. In some embodiments, a film substantially encapsulates a core.

A film can have an average thickness in various ranges. In some embodiments, an averaged thickness is about or less than 200 nm, 100 nm, 50 nm, 40 nm, 30 nm, 20 nm, 15 nm, 10 nm, 5 nm, 1 nm, 0.5 nm, or 0.1 nm. In some embodiments, an averaged thickness is in a range from about 0.1 nm to about 100 nm, about 0.5 nm to about 50 nm, or about 5 nm to about 20 nm. In some embodiments, an averaged thickness is in a range of any two values above.

In some embodiments, a coating film include one or more layers. A plurality of layers each can respectively contain one or more materials. According to various embodiments of the present disclosure, a layer can consist of or comprise metal (e.g., gold, silver, and the like), semi-metal or non-metal, and metal/semi-metal/non-metal oxides such as silica ($SiO_2$). In certain embodiments, a layer can consist of or comprise a magnetic material (e.g., iron oxide).

Additionally or alternatively, materials of a layer can be polymers. For example, a layer can be polyethyleneimine as demonstrated in Example 1. In some embodiments, a layer is or includes one or more polymers, particularly polymers that which have been approved for use in humans by the U.S. Food and Drug Administration (FDA) under 21 C.F.R. § 177.2600, including, but not limited to, polyesters (e.g. polylactic acid, poly(lactic-co-glycolic acid), polycaprolactone, polyvalerolactone, poly(1,3-dioxan-2-one)); polyanhydrides (e.g. poly(sebacic anhydride)); polyethers (e.g., polyethylene glycol); polyurethanes; polymethacrylates; polyacrylates; polycyanoacrylates; copolymers of PEG and poly(ethylene oxide) (PEO). In some embodiments, a polymer is a lipid.

In some embodiments, a layer is or includes at least a degradable material. Such a degradable material can be hydrolytically degradable, biodegradable, thermally degradable, enzymatically degradable, and/or photolytically degradable polyelectrolytes. In some embodiments, degradation may enable release of one or more agents associated with a particle described herein.

Degradable polymers known in the art, include, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine (e.g., poly(L-lysine) (PLL)), poly(lactic acid) (PLA), poly(glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly(beta-amino esters), which may be suitable for use in accordance with the present application.

In some embodiments, layer-by-layer (LBL) films can be used alternatively or in addition to other layers to coat a particle core in accordance with the present invention. A LBL film may have any of a variety of film architectures (e.g., numbers of layers, thickness of individual layers, identity of materials within films, nature of surface chemistry, presence and/or degree of incorporated materials, etc), as appropriate to the design and application of a coated particle core as described herein. In certain embodiments, a LBL film may has a single layer.

LBL films may be comprised of multilayer units in which alternating layers have opposite charges, such as alternating anionic and cationic layers. Alternatively or additionally, LBL films for use in accordance with the present invention may be comprised of (or include one or more) multilayer units in which adjacent layers are associated via other non-covalent interactions. Exemplary non-covalent interactions include, but are not limited to ionic interactions, hydrogen bonding interactions, affinity interactions, metal coordination, physical adsorption, host-guest interactions, hydrophobic interactions, pi stacking interactions, van der Waals interactions, magnetic interactions, dipole-dipole interactions and combinations thereof Detailed description of LBL films can be found in U.S. Pat. No. 7,112,361, the contents of which are incorporated herein by reference. Features of the compositions and methods described in the patent may be applied in various combinations in the embodiments described herein.

In some embodiments, a layer can have or be modified to have one or more functional groups. Apart from changing the surface charge by introducing or modifying surface functionality, functional groups (within or on the surface of a layer) can be used for association with any agents (e.g., detectable agents, targeting agents, or PEG).

iii. Agents

In some embodiments, the present invention provides compositions that comprise one or more agents. In some embodiments, one or more agents are associated independently with a core, a film coating the core, or both. For example, agents can be covalently linked to or hybridized to a nucleic acid-containing core, and/or encapsulated in a coating film of a particle described herein. In certain embodiments, an agent can be associated with one or more individual layers of an LBL film that is coated on a core, affording the opportunity for exquisite control of loading and/or release from the film.

In theory, any agents including, for example, therapeutic agents (e.g. antibiotics, NSAIDs, glaucoma medications, angiogenesis inhibitors, neuroprotective agents), cytotoxic agents, diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be associated with the LBL film disclosed herein to be released.

In some embodiments, compositions described herein include one or more therapeutic agents. Exemplary agents include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, a therapeutic agent to be delivered is an agent useful in combating inflammation and/or infection.

In some embodiments, a therapeutic agent is or comprises a small molecule and/or organic compound with pharmaceutical activity. In some embodiments, a therapeutic agent is a clinically-used drug. In some embodiments, a therapeutic agent is or comprises an antibiotic, anti-viral agent, anesthetic, anticoagulant, anti-cancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, etc.

In some embodiments, a therapeutic agent may be a mixture of pharmaceutically active agents. For example, a local anesthetic may be delivered in combination with an anti-inflammatory agent such as a steroid. Local anesthetics may also be administered with vasoactive agents such as epinephrine. To give but another example, an antibiotic may be combined with an inhibitor of the enzyme commonly produced by bacteria to inactivate the antibiotic (e.g., penicillin and clavulanic acid).

In some embodiments, a therapeutic agent may be an antibiotic. Exemplary antibiotics include, but are not limited to, β-lactam antibiotics, macrolides, monobactams, rifamycins, tetracyclines, chloramphenicol, clindamycin, lincomycin, fusidic acid, novobiocin, fosfomycin, fusidate sodium, capreomycin, colistimethate, gramicidin, minocycline, doxycycline, bacitracin, erythromycin, nalidixic acid, vancomycin, and trimethoprim. For example, β-lactam antibiotics can be ampicillin, aziocillin, aztreonam, carbenicillin, cefoperazone, ceftriaxone, cephaloridine, cephalothin, cloxacillin, moxalactam, penicillin G, piperacillin, ticarcillin and any combination thereof.

An antibiotic used in accordance with the present disclosure may be bacteriocidial or bacteriostatic. Other antimicrobial agents may also be used in accordance with the present disclosure. For example, anti-viral agents, antiprotazoal agents, anti-parasitic agents, etc. may be of use.

In some embodiments, a therapeutic agent may be or comprise an anti-inflammatory agent. Anti-inflammatory agents may include corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylate, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

Those skilled in the art will recognize that this is an exemplary, not comprehensive, list of agents that can be released using compositions and methods in accordance with the present disclosure. In addition to a therapeutic agent or alternatively, various other agents may be associated with a coated device in accordance with the present disclosure.

More details of particle can be found in U.S. Patent Application No. US2014/0328931, the contents of which are incorporated herein by reference.

E. DNA Templates

The DNA template may comprise a stem region, a first loop region, and a second loop region. These regions together form a dumbbell DNA template. Each first and second loop region can comprise 4 nucleotides to 20 nucleotides. In some embodiments, the first and second loop region can comprise 4, 5, 6, 7, 8, 9, 10, 11, 12, 13, 14, 15, 16, 17, 18, 19, or 20 nucleotides. In some embodiments, the first and second loop region can comprise the sequences comprises the nucleic acid sequences set forth in SEQ ID NOs: 20-26. Such sequences when transcribed by RCT/RCA may be digested by RNase T1.

```
                                        (SEQ ID NO: 20)
5'-CTGACC-3';

(SEQ ID NO: 21)
5'-TGATAGGAAGTT-3';

(SEQ ID NO: 22)
5'-TTTCTT-3';

(SEQ ID NO: 23)
5'-CCATAGGAAGCC-3';

(SEQ ID NO: 24)
5'-CCCCCCCCCCCC-3';

(SEQ ID NO: 25)
5'-TGATAT-3';

(SEQ ID NO: 26)
5'-CCCCCC-3'.
```

In some embodiments, the connecting or loop segment comprises the nucleic acid sequences set forth in SEQ ID NOs: 27-29. Such sequences when transcribed by RCT/RCA may be digested by RNase T2.

```
                                        (SEQ ID NO: 27)
5'-TTTTTT-3';

(SEQ ID NO: 28)
5'-GGGTGG-3';
and (SEQ ID NO: 29)
5'-TGGCCAGGAAGT-3'.
```

In some embodiments, the connecting or loop segment comprises the nucleic acid sequences set forth in SEQ ID NOs: 30-33. Such sequences when transcribed by RCT/RCA may be digested by RNase U2.

5'-TTTTTT-3'; (SEQ ID NO: 30)

5'-GGGTTT-3'; (SEQ ID NO: 31)

5'-GGGTGG-3'; (SEQ ID NO: 32)
and

5'-TGGCCAGGAAGT-3'. (SEQ ID NO: 33)

In some embodiments, the connecting or loop segment comprises the nucleic acid sequences set forth in SEQ ID NOs: 34-37. Such sequences when transcribed by RCT/RCA may be digested by RNase A.

5'-GGGGGG-3'; (SEQ ID NO: 34)

5'-AAAAAA-3'; (SEQ ID NO: 35)

5'-AAGAAG-3'; (SEQ ID NO: 36)
and

5'-AGTAACG-3'. (SEQ ID NO: 37)

In some embodiments, the connecting or loop segment comprises the nucleic acid sequence set forth in SEQ ID NO: 38. Such sequences when transcribed by RCT/RCA may be digested by Ribozyme.

5'-GGCAATAAAGCTGCATTAATGCCGCG-3'. (SEQ ID NO: 38)

In some embodiments, the nucleic acid sequences set forth in SEQ ID NOs: 8-14 may comprise substitutions and additions such that the sequences can be cleaved by RNAse T2, RNase U2, RNase A, RNase H, and ribozyme. A substitution may comprise the replacement of one or more nucleotides by different nucleotides, respectively, as compared to a nucleotide sequence of a parental fragment thereof. In some embodiments, the stem region of the DNA template may comprise 19 to 50 nucleotides. In some embodiments, the stem region may comprise 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to 50 nucleotides. In some embodiments, the stem region of said DNA template comprises contains 25 nucleotides. In some embodiments, the DNA template comprises a silencing sequence. In some embodiments, the first loop region of said DNA template comprises contains 6 nucleotides and the second loop region contains 12 nucleotides. In some embodiments, the first loop region of said DNA template comprises contains 12 nucleotides and the second loop region contains 12 nucleotides.

In some embodiments, the first loop region of said DNA template comprises a nucleotide sequence having at least one Cytosine nucleotide. In some embodiments, the first loop region of said DNA template comprises a nucleotide sequence having all Cytosine nucleotides. In some embodiments, the first loop region of said DNA template comprises a nucleotide sequence having no Cytosine nucleotides. In some embodiments, the second loop region of said DNA template comprises a nucleotide sequence having at least one Cytosine nucleotide. In some embodiments, the second loop region of said DNA template comprises a nucleotide sequence having all Cytosine nucleotides. In some embodiments, the second loop region of said DNA template comprises a nucleotide sequence having no Cytosine nucleotides. In some embodiments, the first fragment is provided as a complementary DNA fragment hybridized to the second fragment of at least one repeat to generate a DNA-RNA hybrid. In some embodiments, the DNA-RNA hybrid is cleaved by RNase H to generate the concatemeric RNA molecule of the present invention.

In some embodiments, the first loop region of said DNA template comprises a Cytosine nucleotide at positions 1, 5, and 6 from the 5' end of the first loop region. In some embodiments, the first loop region of said DNA template comprises a Cytosine nucleotide at position 4 from the 5' end of the first loop region. In some embodiments, the first loop region of said DNA template comprises the nucleotide sequence set forth in SEQ ID NO: 14 and the second loop region of said DNA template comprises the nucleotide sequence set forth in SEQ ID NO: 9. In some embodiments, the first loop region of said DNA template comprises the nucleotide sequence set forth in SEQ ID NO: 8 and the second loop region of said DNA template comprises the nucleotide sequence set forth in SEQ ID NO: 9. In some embodiments, the first loop region of said DNA template comprises the nucleotide sequence set forth in SEQ ID NO: 10 and the second loop region of said DNA template comprises the nucleotide sequence set forth in SEQ ID NO: 9. In some embodiments, the first loop region of said DNA template comprises the nucleotide sequence set forth in SEQ ID NO: 12 and the second loop region of said DNA template comprises the nucleotide sequence set forth in SEQ ID NO: 9. In some embodiments, the first loop region of said DNA template comprises the nucleotide sequence set forth in SEQ ID NO: 13 and the second loop region of said DNA template comprises the nucleotide sequence set forth in SEQ ID NO: 9.

Methods and Uses

The present invention among other things provide methods of making and using the concatemeric RNA molecules described herein. Those of ordinary skill in the art will appreciate that the concatemeric RNA molecules in accordance with the present invention may be prepared by any available technology. In some aspects, rolling circle amplification (RCA) and/or rolling circle transcription (RCT) can be a particularly useful methodology for production of the concatemeric RNA molecules described herein. Exemplary RCA strategies include, for example, single-primer initiated RCA and by various two-primer amplification methods such as ramification amplification (RAM), hyperbranched RCA, cascade RCA, and exponential RCA. In certain embodiments, RNA-containing molecules can be produced via rolling circle transcription (RCT). RCA/RCT may be particularly useful for production of long nucleic acid molecules, and/or furthermore may generate RNA molecules. Those skilled in the art will appreciate that a RNA molecule produced by RCA/RCT will typically have a nucleotide sequence comprising or consisting of multiple copies of the complement of the circular template being amplified.

In some embodiments, a template used for RCA/RCT as described herein is or comprises deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA).

In some embodiments, a template used for RCA/RCT as described herein has a nucleotide sequence that includes one or more silencing.

In some particular embodiments of RCA/RCT contemplated herein, a polymerase selected from the group consisting of T7, T3, or SP6 is utilized to perform the RCA/RCT.

More details of RCA can be found in US Patent Application No. 2010/0189794, the contents of which are incorporated herein by reference. Features of the compositions and methods described in the application may be applied in various combinations in the embodiments described herein. In some embodiments, a first single-stranded nucleic acid molecule is formed by RCA. In some embodiments, the first single-stranded nucleic acid molecule is formed with the aid of a first primer and a nucleic acid polymerase. In some embodiments, a second single-stranded nucleic acid molecule is formed by amplifying the first single-stranded nucleic acid with the aid of a second primer and a polymerase. In some embodiments, a third single-stranded nucleic acid molecule is formed by amplifying the second single-stranded nucleic acid molecule with the aid of a third primer and a polymerase.

A RCA can be repeated with as many primers as desired, e.g., 4, 5, 6, 7, 8, 9, 10 or more primers can be used. In some embodiments, a plurality of primers can be added to templates to form nucleic acid molecules, wherein the plurality can comprise at least about 2, 3, 4, 5, 6, 7, 8, 9, 10, 15, 20, 25, 30, 35, 40, 45, 50, 55, 60, 65, 70, 75, 80, 85, 90, 95, or 100 primers. In some embodiments, more than 100 primers are used. In some embodiments, random fragments of short nucleic acid fragments, e.g., comprising digested or otherwise degraded DNAs, are used as non-specific primers to prime the formation of nucleic acid molecules using rolling circle amplification. In some embodiments, the DNA templates described in section E above are used in the RCA/RCT.

As described herein and will be appreciated by those of skill in the art, polymerization reaction conditions can be adjusted as desired to form nucleic acid molecules and self-assembled particles. For example, reaction conditions that favor stringent nucleic acid hybridization, e.g., high temperature, can be used to favor more specific primer binding during amplification.

One aspect of the invention relates to a method of gene silencing comprising administering the concatemeric RNA molecules described herein to treat a subject in need thereof. In some embodiments, the concatemeric RNA molecules may be provided in as a pharmaceutical composition or as part of a particle. In some embodiments, a plurality of concatemeric RNA molecules are released at the target site.

In some embodiments, a plurality of concatemeric RNA molecules comprises one or more silencing sequence that targets one or more genes associated with a particular disease, disorder, or condition of interest (e.g., cancer, infection, etc).

In some embodiments, the concatemeric RNA molecules may be provided comprising a plurality of silencing sequences, for example targeting the same disease, disorder or condition of interest. To give but one example, in some embodiments, the concatemeric RNA molecules comprises a plurality of silencing sequences, each of which targets a different cancer pathway, for example, as an siRNA that inhibits expression of a protein whose activity contributes to or supports the pathway.

The present invention encompasses the recognition that the concatemeric RNA molecules can be designed and/or prepared to simultaneously deliver to a target site (e.g., to a cancer cell) a plurality of different silencing sequences (e.g., siRNAs), each of which is directed to a different specific molecular target of interest. Certain particles comprising the concatemeric RNA molecules permit facile and close control of relative amounts of such different nucleic acid agents that are or can be delivered (e.g., substantially simultaneously) to the site. To give but one example, RCA/RCT templates can be designed and/or assembled with desired relative numbers of copies of different sequences of interest (e.g., complementary to different siRNAs of interest), so as to achieve precise control over the stoichiometry of delivered siRNA(s). In some embodiments, such control achieves synergistic effects (e.g., with respect to inhibiting tumor growth).

In some embodiments, provided particles or pharmaceutical compositions are administered or implanted using methods known in the art, including invasive, surgical, minimally invasive and non-surgical procedures, depending on the subject, target sites, and agent(s) to be delivered. Particles or pharmaceutical compositions described herein can be delivered to a cell, tissue, organ of a subject. Examples of target sites include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in a subject.

EXEMPLIFICATION

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The following Examples are offered by way of illustration and not by way of limitation.

Example 1

Materials and Methods for Example 2

1. General

All reagents used for in vitro transcription were purchased from New England Biolabs (NEB). The transfection reagents used in this study were either Lipofectamine® 2000 (Life Technologies) or TransIT-X2® (Mirus). The poly-I:C used for all experiments was poly(I:C) HMW from Invivogen, which has an average size of 1.5-8 kb. Nucleic acid ladders were purchased from New England Biolabs and all gels were stained with GelRed (Biotium) for visualization and quantification. RNA quantification was carried out by UV-260 absorbance (Nanodrop) and Quant-iT Ribogreen assay (ThermoFisher). Antibodies used were NF-κB p65 (Abcam ab32536) and Alexa 488-labelled goat anti-rabbit 2° antibody (Thermo A-11008). Nuclear staining was carried out with NucBlue (Molecular Probes).

2. Circular DNA Template Design and Synthesis ssDNA oligos with a 5'-phosphate modification were purchased from Integrated DNA Technologies with PAGE purification. For a complete list of template sequences, please refer to Table 1. All templates were designed to fold into dumbbell structures with the 5' and 3' ends within the ds-region. For circularization, the templates were first diluted to 3 µM in 1× quick ligation buffer (NEB) and heated to 95° C. for 2 min followed by a gradual cooling to 25° C. (~1° C./min) to facilitate folding. T4 DNA ligase was next added to the DNA solution at a ratio of 400 U/0.4 nmol DNA, and the ligation reaction was left at 25° C. for 2 h. Ligation was confirmed by denaturing PAGE (15% TBE-urea); the circularized templates were immediately used for rolling circle transcription without purification.

TABLE 1

DNA Template Sequences Used Examples 1 and 2

| Code | Name | Sequence |
|---|---|---|
| 1 | GFP-3 (22 bp) | 5'P-CCTGAAGTTCATGACATGAACTTCAGG GTCAGCTTGCTGACAGCAAGCTGAC |
| 2 | GFP-5 (21 bp) | 5'P-CCTGAAGTTCATTGTTTGAACTTCAGG GTCAGCTTGCTTGTTGCAAGCTGAC |
| 3 | GFP-6 (22 bp) | 5'P-CCTGAAGTTCATGACAGGATGAACTTC AGGGTCAGCTTGCTGACAGGAGCAAGCTGAC |
| 4 | GFP-8 (21 bp) | 5'P-CCTGAAGTTCAACAGGAAGTGAACTTC AGGGTCAGCTTGCACAGGAAGCAAGCTGAC |
| 5 | GFP-5/10 (21 bp) | 5'P-CCTGAAGTTCATGACAGGAAGTGAACT TCAGGGTCAGCTTGCTTGTTGCAAGCTGAC |
| 6 | GFP-10a (21 bp) | 5'P-CCTGAAGTTCATGACAGGAAGTGAACT TCAGGGTCAGCTTGC TGACAGGAAGGCAAGCTGAC |
| 7 | GFP-10b (21 bp) | 5'P-CCTGAAGTTCATGACAGGAAGTGAACT TCAGGGTCAGCTTGC TGAGAGGAAGGCAAGCTGAC |
| 8 | GFP-10C (21 bp) | 5'P-CCTGAAGTTCATGAGAGGAAGTGAACT TCAGGGTCAGCTTGC TGAGAGGAAGGCAAGCTGAC |
| 9 | GFP-10d (21 bp) | 5'P-CCTGAAGTTCATCCGACCAGCTGAACT TCAGGGTCAGCTTGC TCCGACCAGCGCAAGCTGAC |
| 10 | GFP-10e (21 bp) | 5'P-CCTGAAGTTCACCCCCCCCCCTGAACT TCAGGGTCAGCTTGC CCCCCCCCCCGCAAGCTGAC |
| 11 | GFP-12 (21 bp) | 5'P-CCTGAAGTTCATGACAGGAAGATTGAA CTTCAGGGTCAGCTTGC TGACAGGAAGATGCAAGCTGAC |
| 12 | GFP-10 (25 bp) | 5'P-CCTGAAGTTCATCTGTGACAGGAAGCA GATGAACTTCAGGGTCAGCTTGCTGACAGGA AGGCAAGCTGAC |
| 13 | GFP-10 (25 bp w/ mismatch) | 5'P-CCTGAAGTTCATCTGTGACAGGAAGTA GATGAACTTTAGGGTCAGCTTGT TGACAGGAAGGCAAGCTGAC |
| 14 | GFP-10 (27 bp) | 5'P-CCTGAAGTTCATCTGCATGACAGGAAG TGCAGATGAACTTCAGGGTCAGCTTGCTGAC AGGAAGGCAAGCTGAC |
| 15 | GFP-10 (27 bp w/ mismatch) | 5'P-CCTGAAGTTCATCTGCATGACAGGAAG TGTAGATGAATTTTAGGGTTAGCTTGTTGAC AGGAAGGCAAGCTGAC |
| 16 | GFP-10 (29 bp w/ mismatch) | 5'P-CCTGAAGTTCATCTGCACCTGACAGGA AGGGTGTAGATGAATTTTAGGGTTAGTTTGT TGACAGGAAGGCAAGCTGAC |
| 17 | Luc-10 (21 bp) | CTCTAGAGGATGTGACAGGAAGCATCCTCTA GAGGATAGAATGTGACAGGAAGCATTCTATC |
| 18 | Luc-10 (25 bp) | 5'P-CTCAGCGTAAGTGATTGACAGGAAGAT CACTTACGCTGAGTACTTCGATTTGACAGGA AGAATCGAAGTA |
| 19 | Luc-12/6C (25 bp)' | 5'P-GAGCACTTCTTCATCTGATAGGAAGTT GATGAAGAAGTGCTCGTCCT CGTCCCCCCCCGGACGAGGAC |

TABLE 1-continued

DNA Template Sequences Used Examples 1 and 2

| Code | Name | Sequence |
|---|---|---|
| 20 | GFP-12/6C (25 bp) | 5'P-CCTGAAGTTCATCTGTGATAGGAAGTT CAGATGAACTTCAGGGTCAGCTTGCCCCCCC GCAAGCTGAC | i) Complementary regions highlighted in bold.

RCT Optimization

Figure 8:
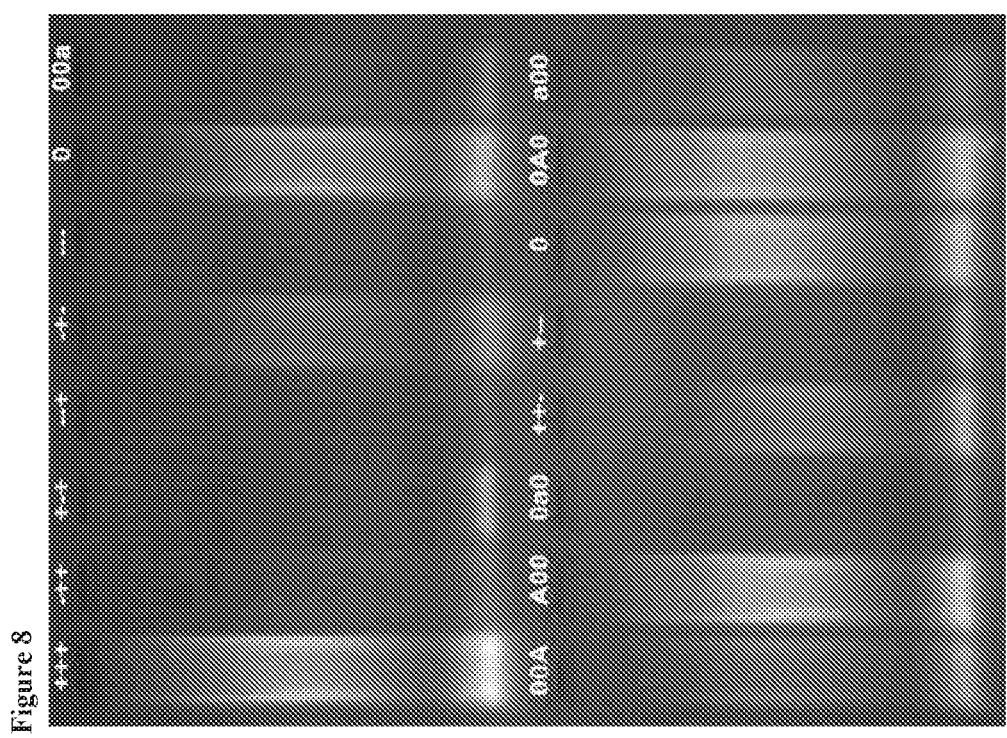
FIG. 8 is a photograph depicting an agarose gel electrophoresis (1.5%, TBE) of reaction products from CCD screen described in Table 2.

Rolling circle transcription was optimized according to a central composited design screen (SAS JMP 11). Reactions were all made to have a final volume of 25 µL with varying volumes of DNA template (3 µM), NTPs (25 mM each), and T7 RNA polymerase (50 U/µL). Reactions were allowed to proceed for 24 h at 37° C., treated with DNase, then analyzed by Quant-IT Ribogreen® assay and agarose gel electrophoresis (FIG. 8) to determine yield and the ratio of long/short product. Model selection was carried out using stepwise least squares regression with k-folds cross-validation (k=5). The optimal models for predicting RNA yield and long/short RNA are shown in Table 2.

TABLE 2

CCD Screen for RCT Optimization from Template 6

| Pattern[a] | Vol. Template (µL) | Vol. Enzyme (µL) | Vol NTP (µL) | RNA Yield (µg/µL) | Long/Short RNA |
|---|---|---|---|---|---|
| +++ | 16 | 4 | 2 | 0.68 | 1.98 |
| −++ | 4 | 4 | 2 | 0.06 | 0.01 |
| +−+ | 16 | 0.5 | 2 | 0.09 | 0.00 |
| −−+ | 4 | 0.5 | 2 | 0.01 | 0.00 |
| −+− | 4 | 4 | 0.5 | 0.18 | 1.20 |
| −−− | 4 | 0.5 | 0.5 | 0.02 | 0.00 |
| 0 | 10 | 2.25 | 1.25 | 0.35 | 2.47 |
| 00a | 10 | 2.25 | 0.5 | 0.10 | 0.19 |
| 00A | 10 | 2.25 | 2 | 0.22 | 1.05 |
| A00 | 16 | 2.25 | 1.25 | 0.48 | 3.08 |
| 0a0 | 10 | 0.5 | 1.25 | 0.05 | 0.00 |
| ++− | 16 | 4 | 0.5 | 0.27 | 1.46 |
| +−− | 16 | 0.5 | 0.5 | 0.06 | 0.00 |
| 0 | 10 | 2.25 | 1.25 | 0.32 | 3.02 |
| 0A0 | 10 | 4 | 1.25 | 0.69 | 3.05 |
| a00 | 4 | 2.25 | 1.25 | 0.17 | 1.72 |

[a]Patterns indicate relative amounts of different components used in the screen (0 = center point; a/− = lower point; A/+ = higher point).

3. Cell Culture

GFP-expressing HeLa and A549 cell lines were purchased form CellBioLabs and maintained in DMEM supplemented with 10% FBS and 1% penicillin/streptomycin. Luciferase-expressing SKOV3 and UCI101 ovarian cancer cells were kind gifts from Dr. Lorenzo Ceppi, Dr. Wei Wei, and Dr. Michael Birrer (Massachusetts General Hospital). These were maintained in RPMI with 10% FBS, 1% penicillin/streptomycin and 40 µg/mL blasticidin for selection. All cells were maintained at 37° C. in a 5% $CO_2$ humidified atmosphere.

4. Rolling Circle Transcription and Isolation of p-shRNA

Optimized reaction conditions for RCT were found by varying the concentrations of NTPs, circular DNA, and T7 RNA polymerase according to a central composite design. Optimal conditions were determined by response surface modeling carried out in JMP Pro 11; these conditions were then used for all subsequent experiments (for additional details see the Supplemental Information). The optimized RCT reaction conditions for a typical 200 µL reaction were as follows: 120 µL of the DNA ligation reaction (3 µM DNA) was combined with 20 µL of 10× RNAPol reaction buffer, 12.5 µL of 100 mM mixed NTPs, 40 µL of T7 RNA polymerase (50,000 U/mL), and 7.5 µL of RNase-free water. The reaction mixture was incubated for 48 h at 37° C. before quenching with 20 µL of 0.5 M EDTA (this step also dissolves magnesium pyrophosphate/RNA microsponge particles, releasing all RNA into the solution (Shopsowitz, K E et al. (2014) Small 10: 1623-1633)); 20 min later, the RNA was isolated by pressure-driven ultrafiltration (200 kDa MWCO), washed 3× with 1 mL of RNase-free water and resuspended in 200 µL of RNase-free water. p-shRNA concentration, quality, and size distribution were determined by UV-absorbance (Nanodrop) and gel electrophoresis (1.5% agarose, 1× TBE). Denaturing gel electrophoresis was performed by heating the RNA samples in formamide-containing buffer (RNA loading buffer, NEB) for 10 min at 70° C. then loading onto either a formaldehyde-agarose gel (1.5% agarose, 1× MOPS buffer, 7% formaldehyde) or a 15% PAGE-Urea gel (Bio-Rad).

5. Circular Dichroism

Circular dichroism was measured with an Aviv Model 202 CD spectrometer. RNA samples were dissolved at 60 ng/mL in TE buffer and spectra were collected from 200-300 nm with a 1 nm bandwidth and 5 s averaging. After collecting an initial spectrum at 25° C., the CD signal at 210 nm was monitored while heating to 95° C. (CD signal measured at 2° C. intervals with 0.25 min equilibration time). A final spectrum was then collected at 95° C.

6. Enzymatic Digests and Serum Stability

RNase I digests were performed with recombinant RNase $I_f$ (New England Biolabs). p-shRNA samples were dissolved at a final concentration of 60 ng/µL in the recommended buffer (NEBuffer 3) and sonicated for 5 min prior to the addition of 1 µL of enzyme solution (50,000 Units/mL). The reaction was incubated at 37° C. for 10 min, then inactivated through the addition of 3 µL of 0.5 M EDTA and heating for 10 min at 70° C. For analysis, 10 µL aliquots from each reaction were run on a non-denaturing 15% TBE-PAGE gel for 1.5 h at 80 V, stained with GelRed® (Biotium) and imaged under UV illumination.

RNase T1 digests were performed using recombinant RNase T1 (New England Biolabs) following a similar procedure except that 50 mM Tris buffer containing 2 mM EDTA was used with 7 Units of enzyme, and the digests were carried out for 5 h at 37° C. For analysis, 10 µL aliquots were immediately loaded onto a non-denaturing PAGE gel (15% TBE), or for denaturing PAGE analysis, samples were mixed with formamide-containing denaturing buffer and heated to 70° C. for 10 min prior to loading onto a denaturing PAGE gel (15% TBE-urea). Band quantification was performed using Image J and the ratios of large to small fragments are reported as the average of three experiments±s.e.m.

Serum degradation studies were carried out using 50% human serum (Corning Cellgro). p-shRNA or siRNA samples were first diluted to 25 ng/µL in PBS then mixed with an equal volume of human serum and incubated at 37° C. Aliquots were removed at the indicated time points, combined with RNaseOut (to inactivate serum nucleases), and stored at −80° C. until analysis. Samples were run on a non-denaturing PAGE gel (15% TBE) at 80 V for 1.5 h, stained with GelRed, and imaged under UV illumination. Band quantification was performed using Image J and half-lives were calculated by fitting an exponential decay function in Prism. An additional gel showing a serum only control is provided in the Supplemental Information (FIG. 13, Panel (C)).

7. Structural Prediction

Folding predictions were performed using 2-6 repeat sequences of p-shRNA, assuming that transcription was initiated at one of the single-stranded loops. The minimum free energy (MFE) and co-transcriptionally folded structures were determined using the RNAfold (Gruber, A R et al. (2008) Nucleic Acids Res 36: 70-74) and CoFold (Proctor, J R et al. (2013) Nucleic Acids Res 41: 1-11) web servers, respectively. Both predictions were carried out using the energy/folding parameters indicated in the text. 3D models based on MFE or co-transcriptional folding were generated using RNAComposer (Popenda, M et al. (2012) Nucleic Acids Res 40: 1-12) and measurements/rendering was performed using PyMol.

8. p-shRNA Complexation with Transfection Reagents

Complexation with Lipofectamine® 2000: RNA was dissolved in Opti-MEM at a concentration of 6 µg/mL and combined with Lipofectamine® 2000 reagent dissolved in an equal volume of Opti-MEM (1.7 µL of Lipofectamine/µg RNA). After mixing, the sample was allowed to sit for 15 min at room temperature prior to use, giving a final RNA concentration of 3 µg/mL.

Complexation with Mirus TransIT-X2®: TransIT-X2® reagent was added to a 5.5 µg/mL solution of RNA in Opti-MEM at a ratio of 3.7 µL of reagent/µg of RNA. The solution was mixed thoroughly and allowed to sit for 25 min before diluting with Opti-MEM to a final RNA concentration of 3 µg/mL. Lipofectamine® and TransIT-X2® only samples were both prepared following the above procedures but excluding RNA.

9. Cell Viability and Knockdown Assays

Cell viability: Experiments were carried out 24 h after seeding cells in a 96-well plate with 100 µL of complete DMEM (10% FBS), at which point the cells were ~50% confluent. Complexes formed in serum-free Opti-MEM were added to the cells at volumes ranging from 1 µL to 100 µL (each condition was performed in triplicate); following the addition of RNA, well volumes were all adjusted to 200 µL final volume with Opti-MEM and left to incubate for 48 h (final [FBS]=5%). Cell viability was then assayed with CellTiter-Glo reagent (Promega) according to the manufacturer's instructions and $IC_{50}$ values were calculated by fitting a 3-parameter log-logistic model to the dose-response data via the DRC package in R (Ritz, C et al. (2005) J Sta Softw 12: 1-22).

Caspase activity: Caspase activation was measured using the Caspase-Glo 3/7, Caspase-Glo 8, and Caspase-Glo 9 assay systems (Promega). Cells were incubated with p-shRNA or poly-I:C/Lipofectamine complexes for 14 h prior to measuring caspase activity according to the manufacturer's protocol.

GFP knockdown: Cells were prepared in a 96-well plate as described above. RNA complexes formed in Opti-MEM were added to the cells to give a final RNA concentration of 10 or 30 nM (with respect to dsRNA units; this corresponds to ~180-540 ng/mL RNA); after 24 h, the media was replaced with fresh DMEM and the cells were left for an additional 48 h before analyzing reporter gene expression (i.e., 72 h after adding RNA). GFP was analysed by flow cytometry using a FACSCalibur flow cytometer equipped with a high-throughput sampler ($\lambda_{Ex}$=488 nm; $\lambda_{Em}$=530/30 nm). To prepare the cells for flow cytometry, they were first washed with PBS, disassociated with trypsin, and resuspended in DMEM containing 10% FBS. The resulting data was analyzed using FloJo and presented as mean fluorescence averaged over three independent samples, normalized to the average fluorescence of untreated cells.

Luciferase knockdown: Cells were prepared in a 96-well plate as described above. RNA complexes formed in Opti-MEM were added to cells to give a final concentration of 15 nM and the medium was replaced with fresh RPMI medium 24 hours after transfection. After an additional 48 hours, the cells were lysed with 75 μL 1× Glo Lysis Buffer (Promega). For each well, a 25 μL aliquot of the cell lysate was transferred to another 96-well plate and assayed for total protein content with the Pierce BCA Protein Assay Kit. Luciferase expression in the remaining cell lysate was measured with the Steady-Glo luciferase assay system (Promega) using a Tecan Infinite M200 Pro 96-well plate reader. Luminescence readings were first normalized to total protein and presented as the mean for three independent samples normalized to the corresponding value for untreated cells.

10. NF-κB Nuclear Translocation Assay p-shRNA or poly-I:C/Lipofectamine complexes were added to SKOV3 cells in a 24 well plate (~50% confluent) 24 h after seeding at varying concentrations. After 1 h, the media was removed and cells were fixed with 3.7% formaldehyde in PBS (10 min), permeabilized with 0.1% Triton-X in PBS (5 min), incubated with 1° NF-κB antibody (diluted 350×) for 1 h at RT, then stained with 2° antibody (500× dilution) for 1 hr in the dark at RT. During the final 10 min of staining, DAPI (NucBlue) was added to each well (one drop/well) prior to washing the cells with PBS and adding mounting medium. Cells were imaged on an Olympus IX51 epifluorescence microscope using appropriate filter sets for DAPI and AF488. Image analysis was carried out using Cell Profiler (Carpenter, A E et al. (2006) *Genome Biol* 7: R100).

11. Statistical Analysis

All pairwise statistical comparisons were made using a two-sided Welch's test. A p-value cutoff of 0.05 was used for determining statistical significance. Where appropriate, p-values were corrected for multiple comparisons using Holm's method. Results are presented as mean or geometric mean±s.d., s.e.m., or 95% C.I., as specified in the figure legends.

Example 2

Figure 2:
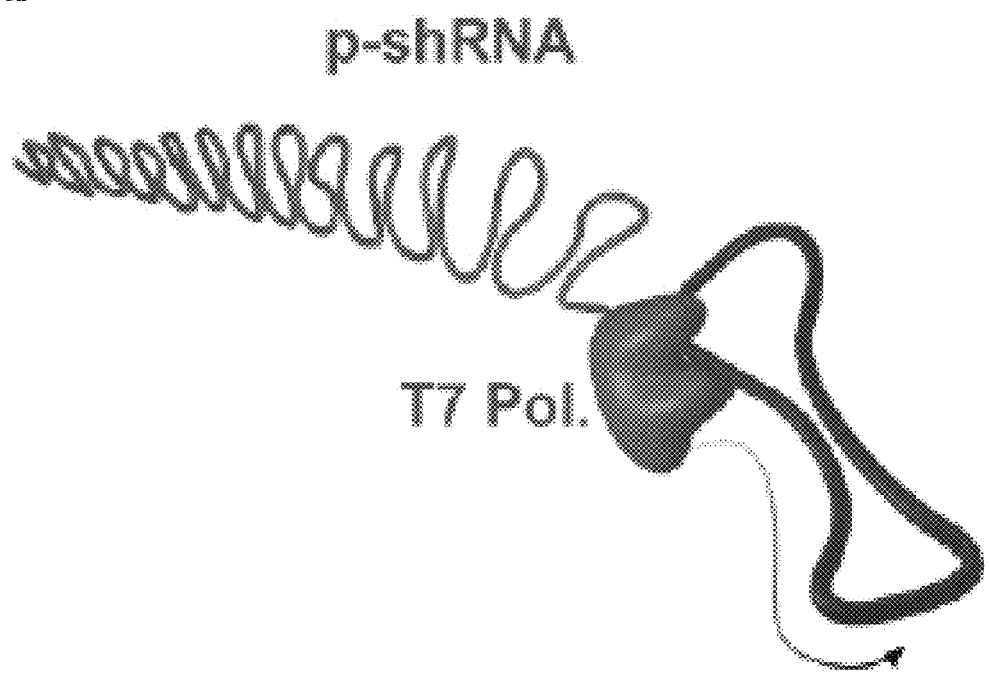
FIG. 2, Panel (A) is a schematic representation of rolling circle transcription from a dumbbell-shaped circular DNA template.
Figure 2:
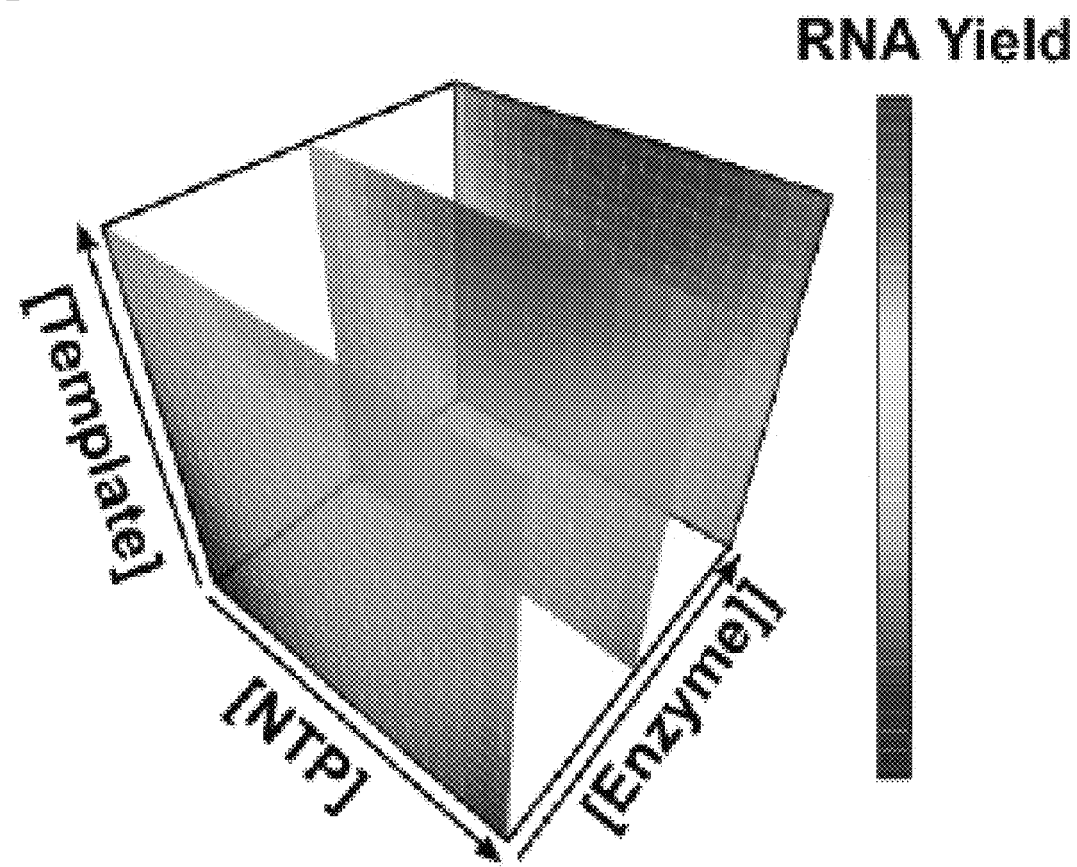
Figure 2:
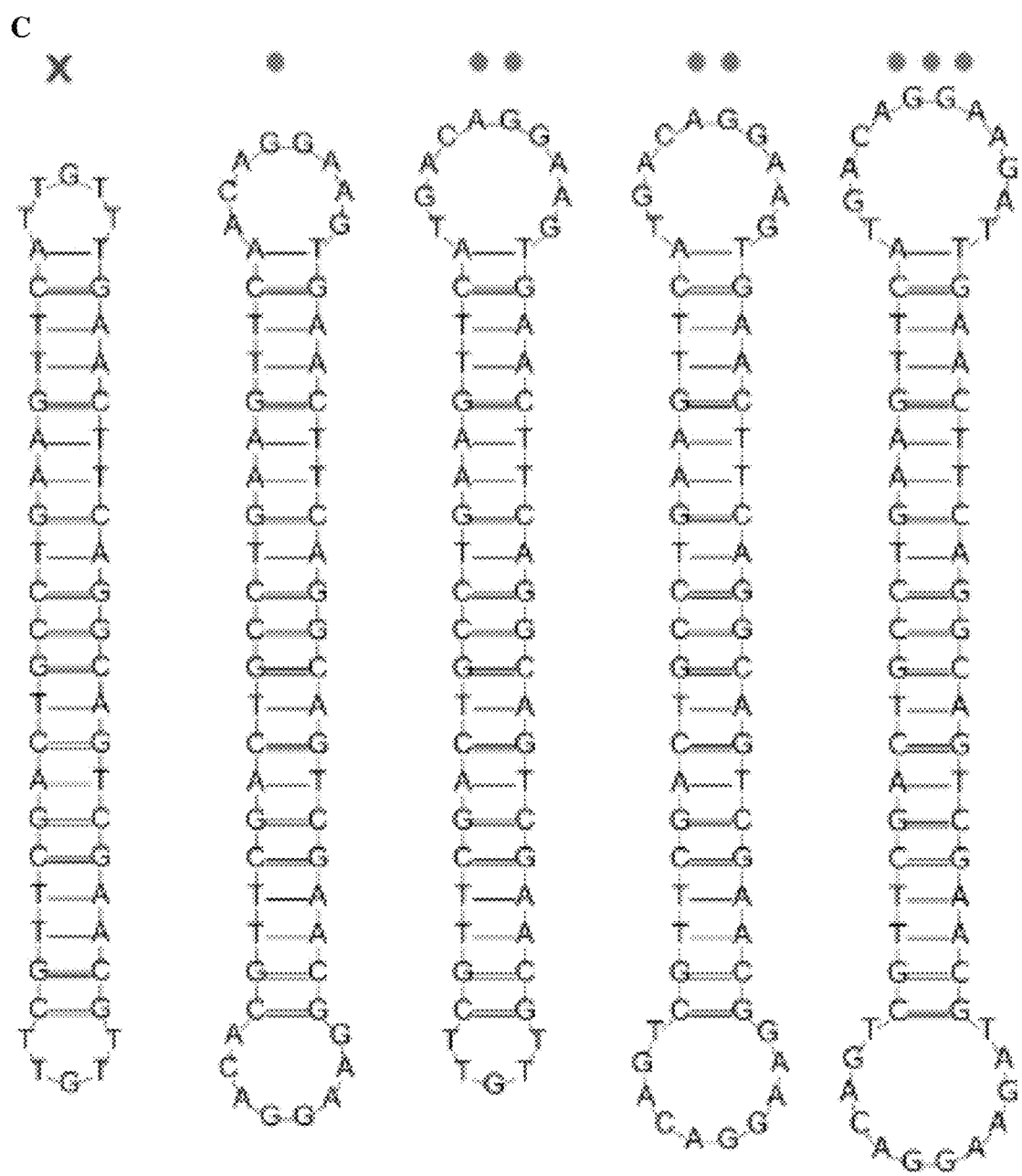
Figure 2:
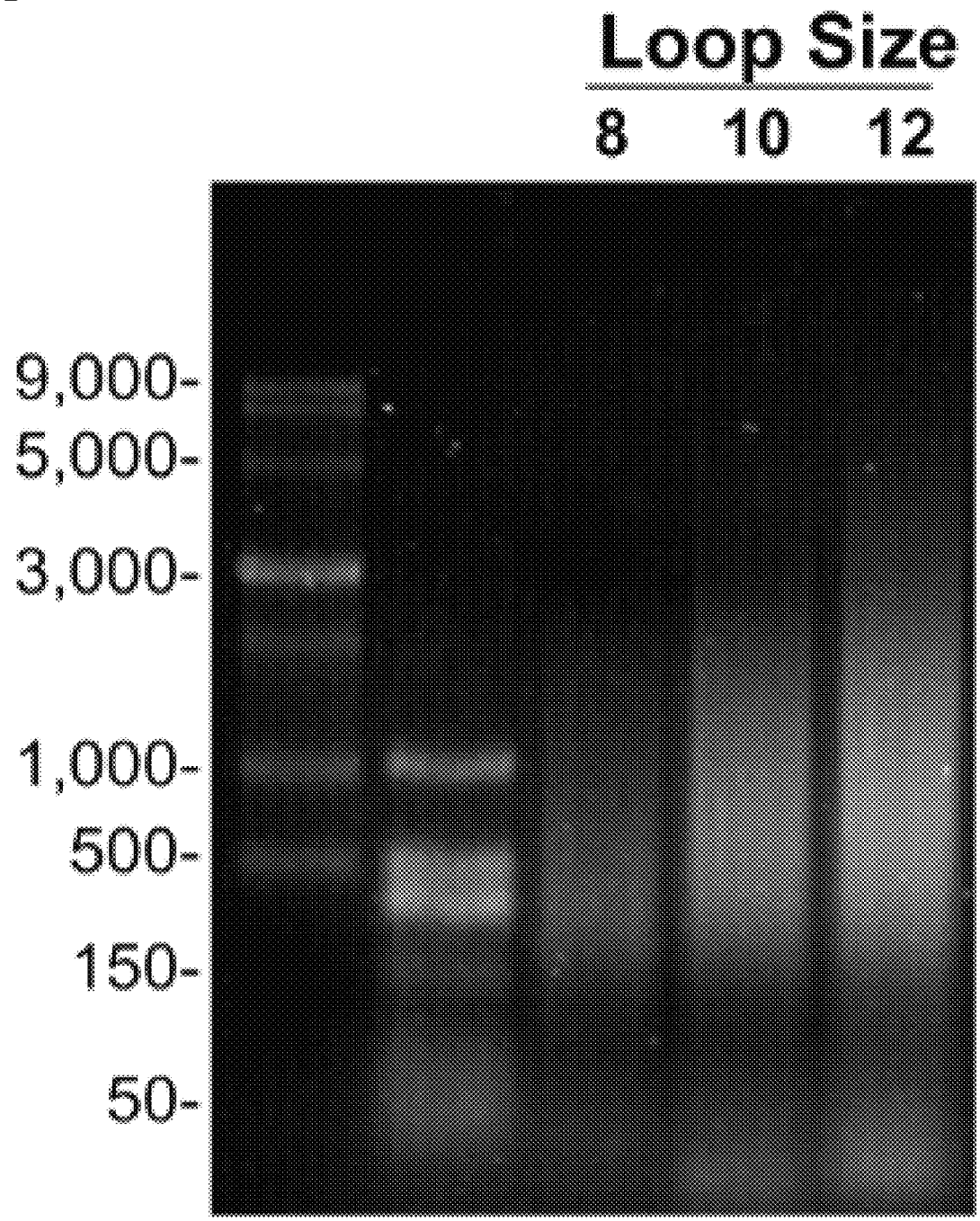
Figure 2:
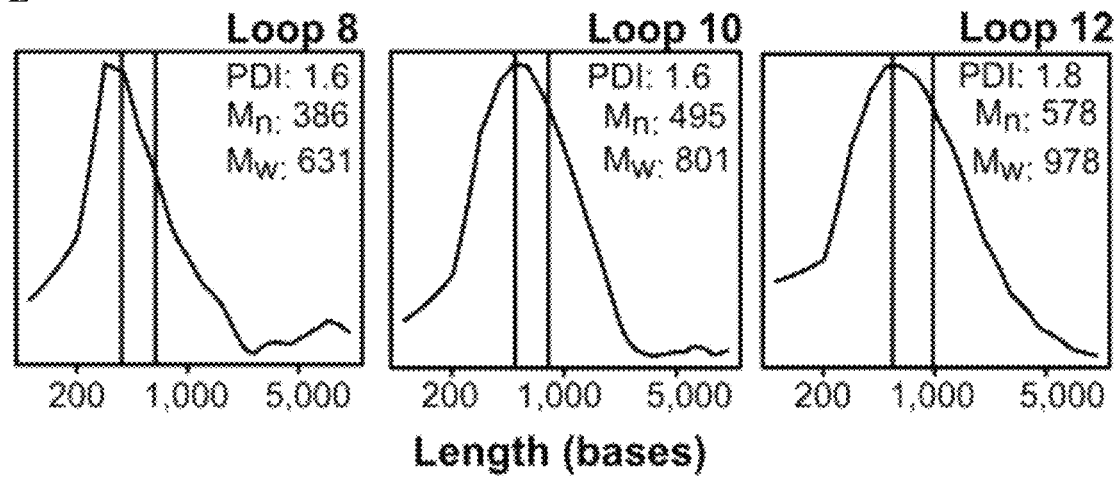
Figure 2:
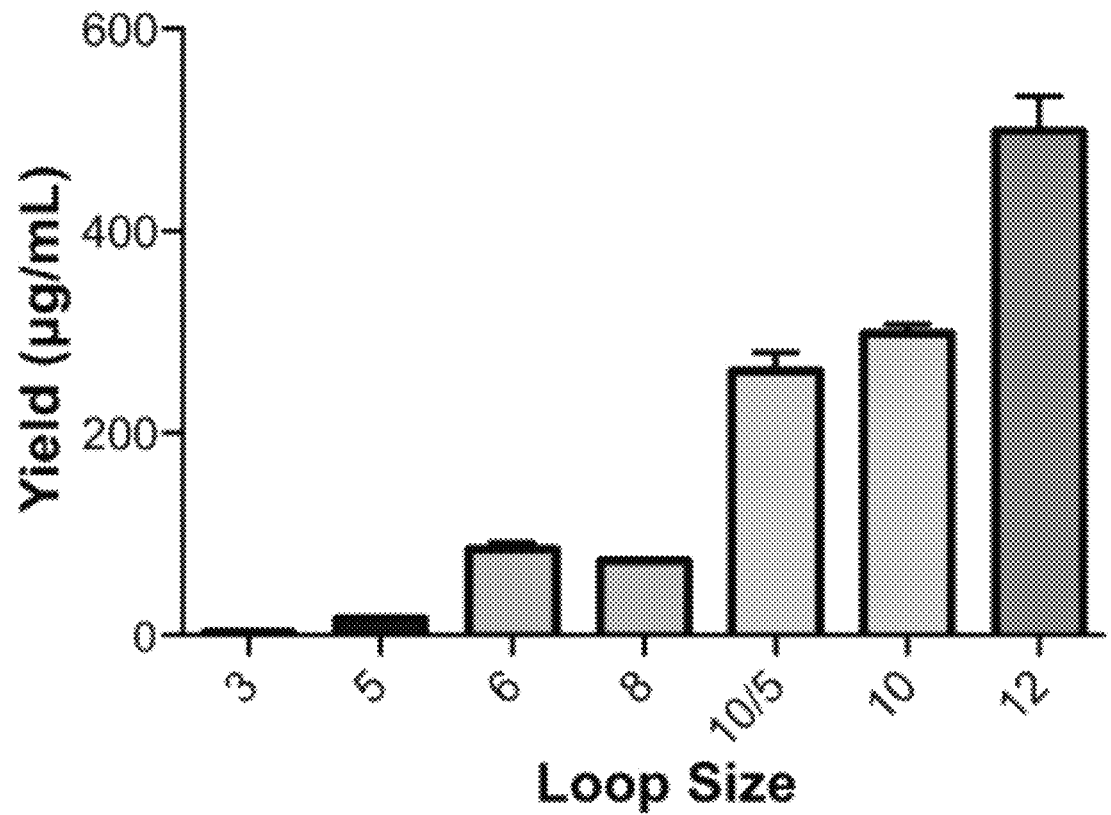
Figure 9:
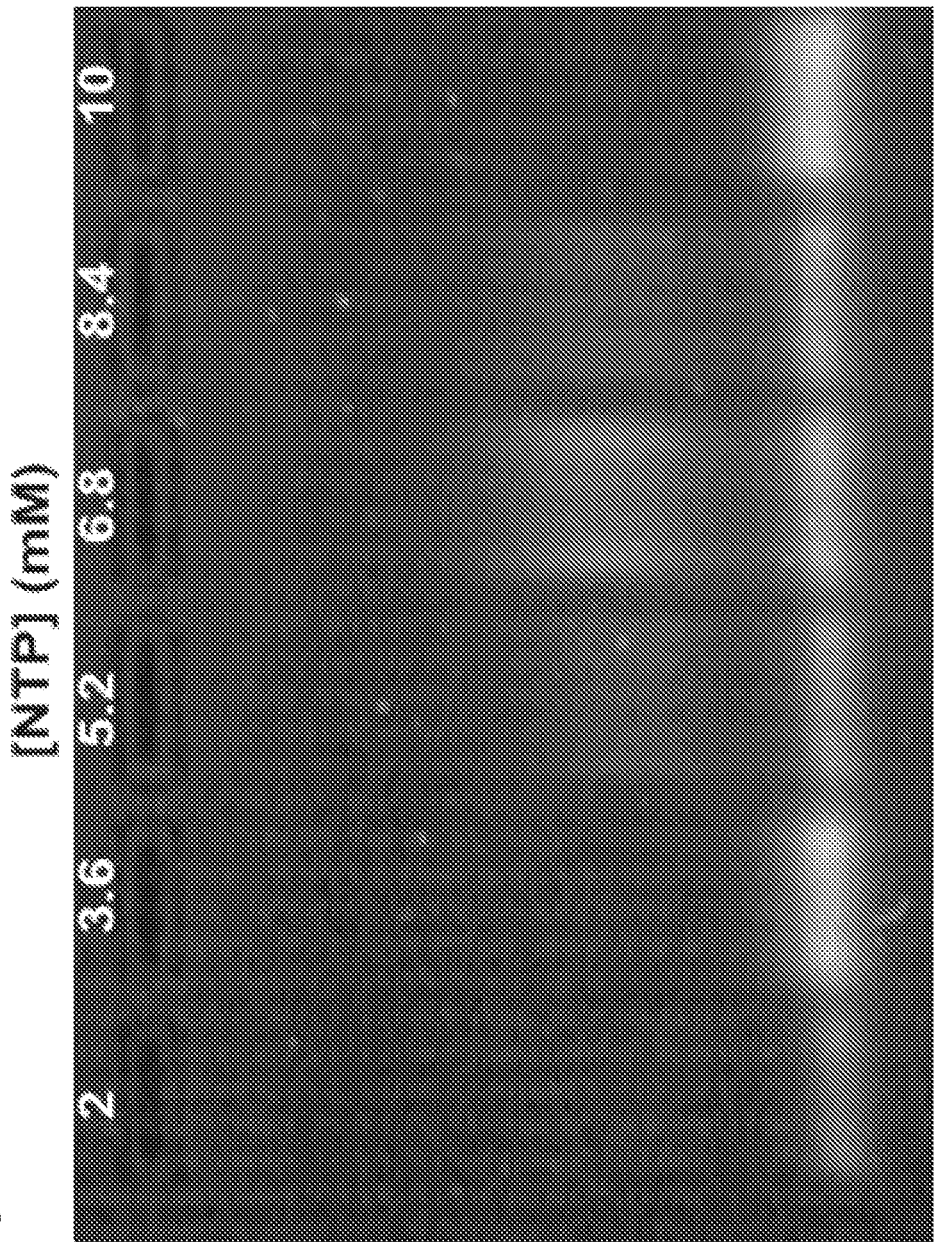
FIG. 9 is a photograph depicting an agarose gel electrophoresis (1.5%, TBE) of follow-up experiment looking at effect of [NTP] on RCT.

Periodic-shRNA Molecules are Capable of Gene Silencing, Cytotoxicity and Innate Immune Activation in Cancer Cells 1. p-shRNA Synthesis A schematic of the rolling circle transcription reaction used in this study is illustrated in FIG. 2, Panel (A). A dumbbell template design (Seyhan, A A et al. (2006) *Oligonucleotides* 363: 353-363) was adopted that is predicted to introduce alternating double-stranded and single-stranded regions into the transcribed RNA. The RCT reaction was first optimized from a DNA template with two equivalent ten-base loops (template 6: loop sequence corresponds to the miR-23a loop) and a 21 bp ds stem by varying the concentrations of T7 RNA polymerase, DNA, and NTPs according to a central composite design screen. The response surface model generated from the screen identified that [Enzyme], [Template], and [NTP]*[NTP] significantly influenced ($p<0.05$) the reaction yield and the ratio of long/short RNA generated through RCT (FIG. 2, Panel (B); for further details see the Supplemental Information, Tables 2 and 3 and FIG. 8). The second-order response to [NTP] was confirmed in a follow-up experiment, where [NTP] was varied from 2-10 mM at a constant concentration of template and enzyme, which demonstrated inhibition of the RCT reaction at [NTP] greater than ~7 mM (FIG. 9).

TABLE 3

Fitted Parameters for Linear Models Predicting RNA Yield and Long/Short RNA

| Y-Parameter | Term | Estimate | Std Error | t Ratio | Prob > \|t\| |
|---|---|---|---|---|---|
| RNA Yield | Intercept | 0.3431243 | 0.054021 | 6.35 | <.0001 |
| RNA Yield | [Template](4.16) | 0.1138413 | 0.041844 | 2.72 | 0.0199 |
| RNA Yield | [Enzyme](0.5.4) | 0.1650017 | 0.041844 | 3.94 | 0.0023 |
| RNA Yield | [NTP](0.5.2) | 0.0421143 | 0.041844 | 1.01 | 0.3358 |
| RNA Yield | [NTP]*[NTP] | −0.174741 | 0.068332 | −2.56 | 0.0266 |
| Long/Short | Intercept | 2.3876419 | 0.301311 | 7.92 | <.0001 |
| Long/Short | [Template](4.16) | 0.3592858 | 0.210678 | 1.71 | 0.1265 |
| Long/Short | [Enzyme](0.5.4) | 0.7685621 | 0.210678 | 3.65 | 0.0065 |
| Long/Short | [NTP](0.5.2) | 0.0184949 | 0.210678 | 0.09 | 0.9322 |
| Long/Short | [Template]*[Enzyme] | 0.2794688 | 0.235546 | 1.19 | 0.2695 |
| Long/Short | [Template]*[NTP] | 0.2144736 | 0.235546 | 0.91 | 0.3691 |
| Long/Short | [Enzyme]*[Enzyme] | −0.498333 | 0.388991 | −1.28 | 0.236 |
| Long/Short | [NTP]*[NTP] | −1.400933 | 0.388991 | −3.6 | 0.007 |

Figure 10:
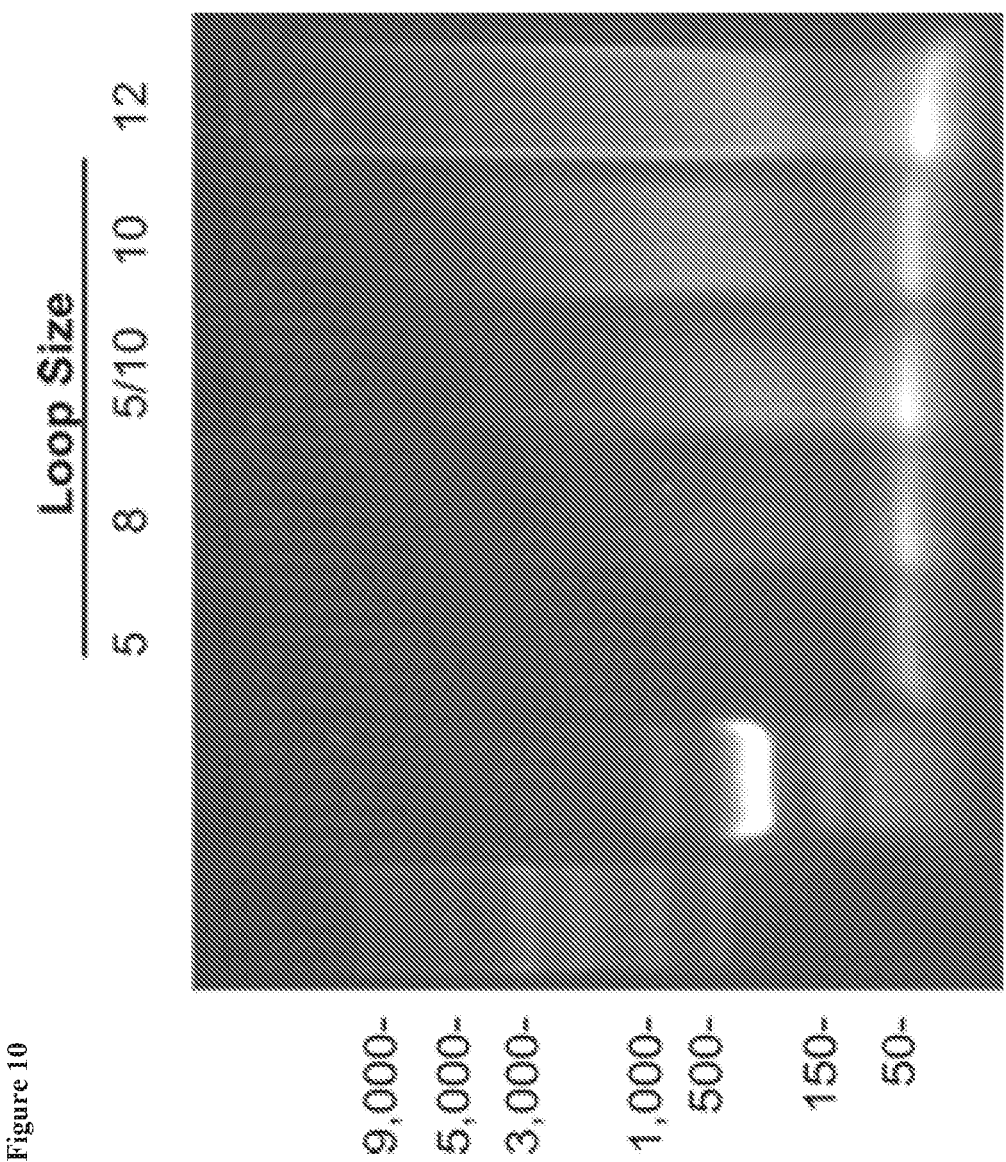
FIG. 10 is a photograph depicting an agarose gel electrophoresis (1.5% TBE) of crude reaction products from templates with different loop sizes (from templates 2 ,4 , 5, 6, and 11).

To assess the scope of useable dumbbell templates for RCT, the lengths and sequences were varied of both the single-stranded and double-stranded regions of DNA dumbbells and analysed the RNA products by gel electrophoresis and Ribogreen assays after 24 h in vitro transcription reactions (FIG. 2, Panels (C)-(F); for a list of all sequences used in this study see Table 1). A series of templates were initially investigated containing a constant 21 bp double-stranded stem corresponding to an siGFP sequence, and loops with variable lengths ranging from 3 to 12 bases (templates with 3- and 6-base loops had one additional base pair). These loop sequences were derived by adding or subtracting bases to the 10-base miR-23a loop sequence while avoiding the introduction of secondary structure. Dumbbell templates that contained two identical loops shorter than 6 bases did not yield any concatenated RNA product (FIG. 2, Panel (F) and FIG. 10). Trends of increasing RNA size and yield were observed with increasing loop size, with the average size for the RNA corresponding to 6-10 repeats based on denaturing agarose (formaldehyde/MOPS) gel analysis (FIG. 2, Panels (D)-(F) and FIG. 10). A similar trend was previously reported for transcription from unstructured circular templates, where an increase in transcript size/yield was observed in going from a 13- to 18-base circular template with T7 RNA polymerase (Frieden, Metal. (1999) *Angew Chemie Int Ed* 38: 3654-3657).

Figure 11:
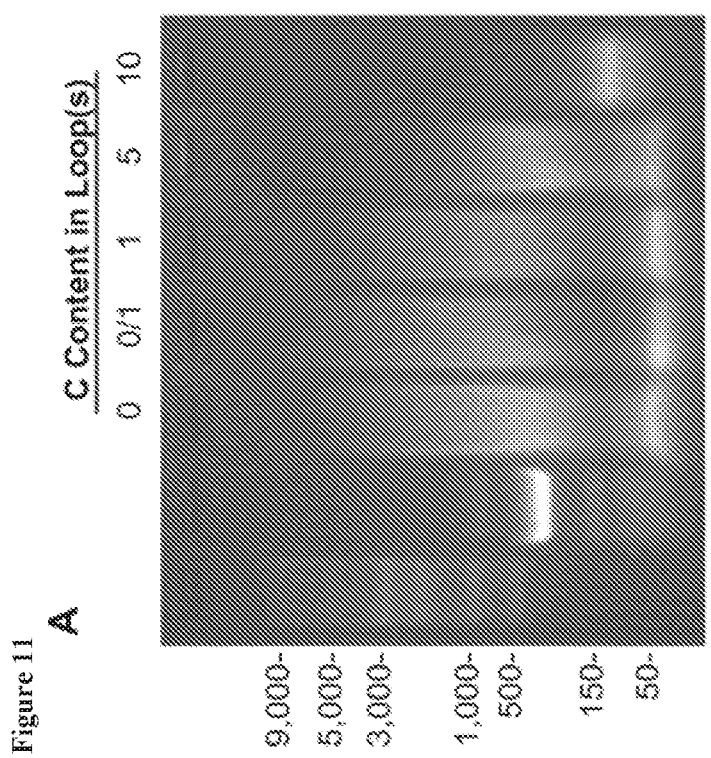
FIG. 11, Panel (A) is a photograph depicting an agarose gel electrophoresis (1.5%, TBE) of crude RCT reaction products from templates with 10 base loops, but different loop sequences (from templates 6-10).
Figure 11:
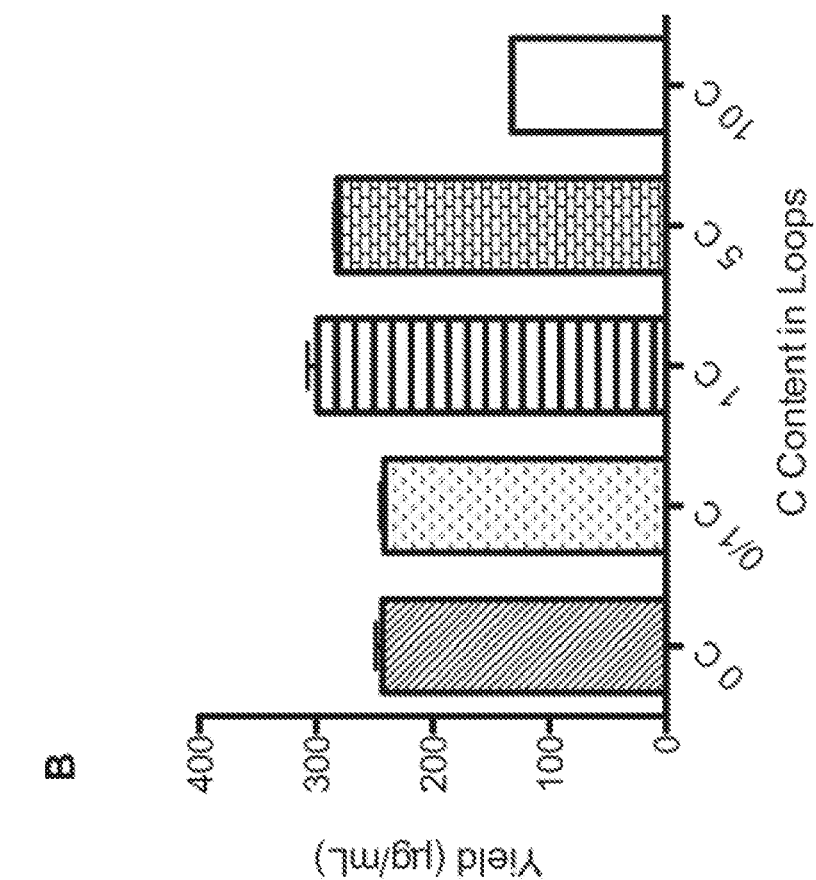

To test whether the effect of loop size on RCT productivity was primarily due to transcription initiation or elongation, RCT from an asymmetric DNA dumbbell was carried out containing 5- and 10-base loops (GFP-5/10). RCT from GFP-5/10 yielded only slightly less RNA than the symmetric template with two 10-base loops (262 vs. 299 µg/mL), with a similar RNA size distribution (FIG. 2, Panels (D)-(F)); a single loop of 5 bases is thus tolerated during the elongation phase of transcription, suggesting that loop size mainly influences transcription initiation. Transcription initiation by T7 RNA polymerase is known to heavily favour incorporating GTP as the first nucleotide (Chamberlin, M et al. (1973) *J Biol Chem* 248: 2235-2244). Whether the presence of Cs in the template loops had an influence on transcription initiation was tested. Five DNA dumbbell templates were compared with 10 base loops containing either no Cs, 1 C in one of the loops, 1 C in both loops (i.e., the original loop sequence), 5 Cs in both loops, and 10 Cs in both loops (i.e., all Cs). Agarose gel electrophoresis comparing the products from these templates showed no difference in size distribution when comparing 0-1 C in the loop sequence; however, a notable decrease in transcript size was observed upon increasing to 5 Cs in the loops, and the 10-C template gave only a short transcript at roughly 100 bases (FIG. 11, Panel (A)). The yields from these different templates were also compared, and found minimal differences for loops with 0-5 Cs, but a significant drop-off in yield (>50%) for the 10-C loop (FIG. 11, Panel (B)).

Figure 12:
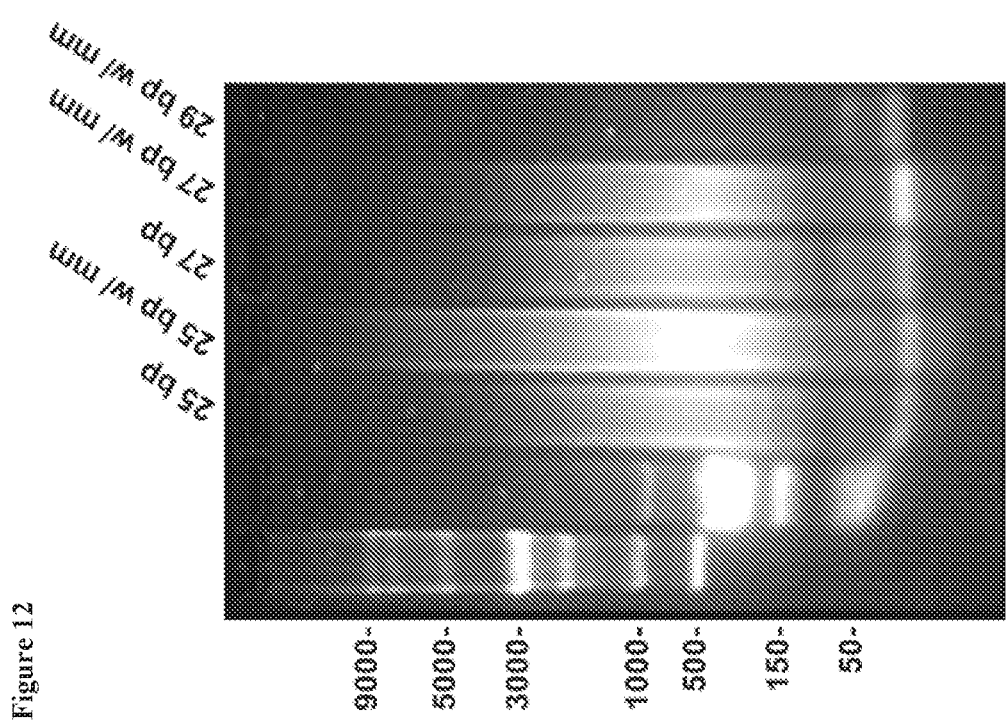
FIG. 12 is a photograph depicting an agarose gel electrophoresis (1.5%, TBE) of RCT products from dumbbell templates with different stems. The templates used were #'s 9-13 (see Table 1).

We also investigated the influence of the double-stranded stem length on the yield of RCT. It was previously reported that a stem length of 29 bp required the introduction of mismatches for efficient transcription, whereas stems of ≤25 bp gave efficient transcription without mismatches (Seyhan, A A et al. (2006) *Oligonucleotides* 363: 353-363). These findings were confirm and similar p-shRNA products were observed from templates with 25 and 27 bp stems (with 10-base loops; templates 12-16) compared to the analogous 21 bp template, with the introduction of three mismatches appearing to improve the reaction yield. In contrast, a drop-off in yield for a template containing a 29 bp stem with three mismatches was observed (FIG. 12).

2. p-shRNA Structure and Stability

Figure 3:
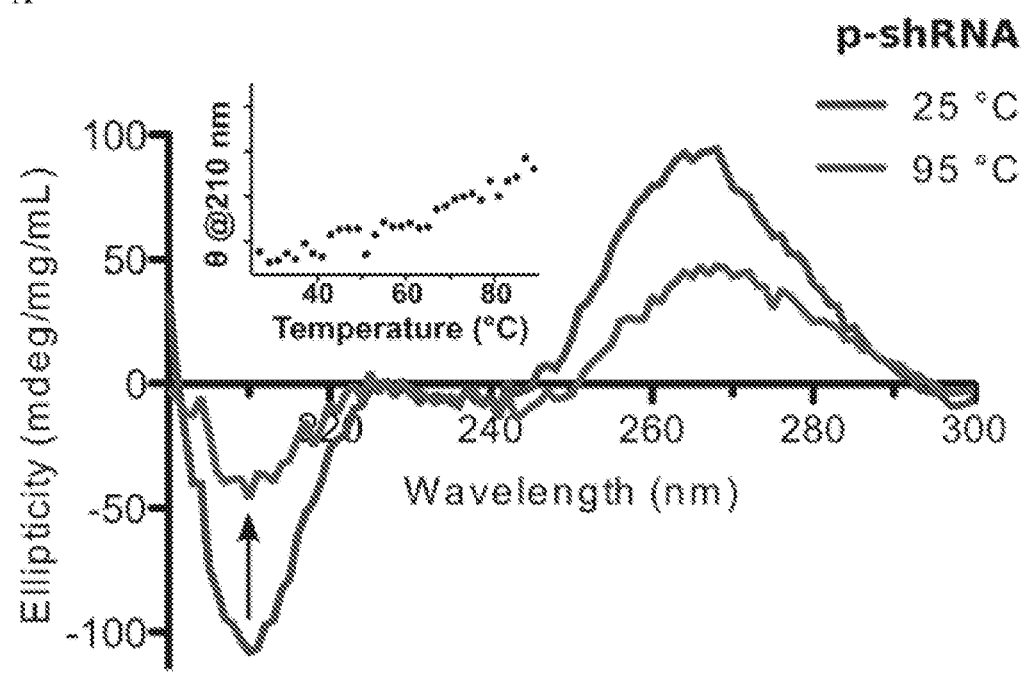
FIG. 3, Panels (A) and (B) are graphs depicting CD spectra of p-shRNA (21 bp stem/10 base loops) and siRNA (21 bp with same sequence) measured at 25 and 95° C. The insets plot the CD signal at 210 nm as a function of temperature.
Figure 3:
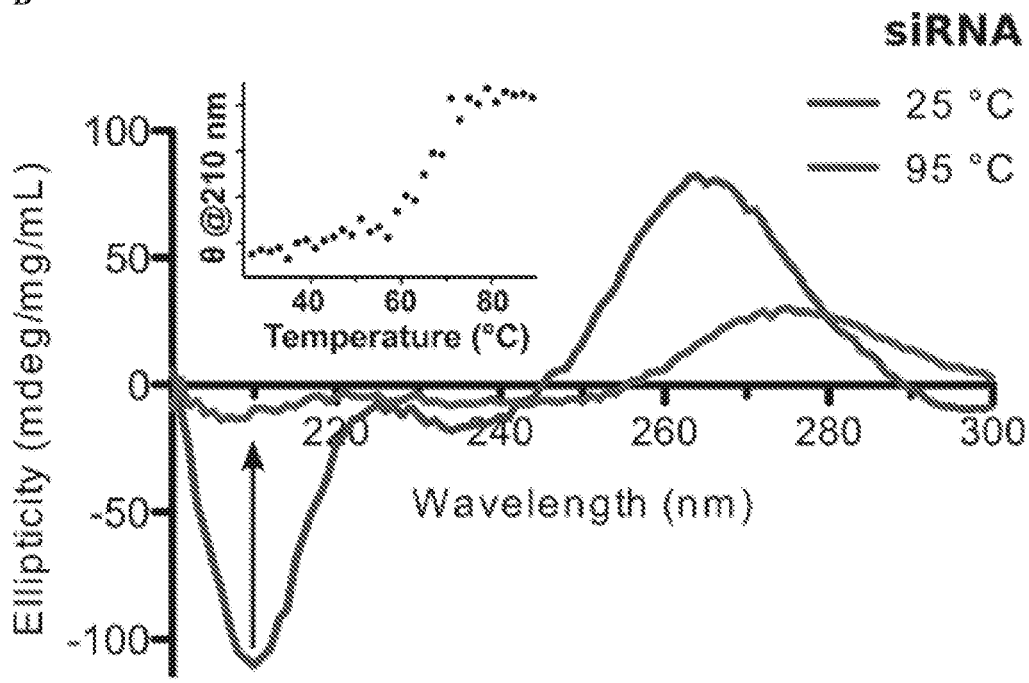
Figure 3:
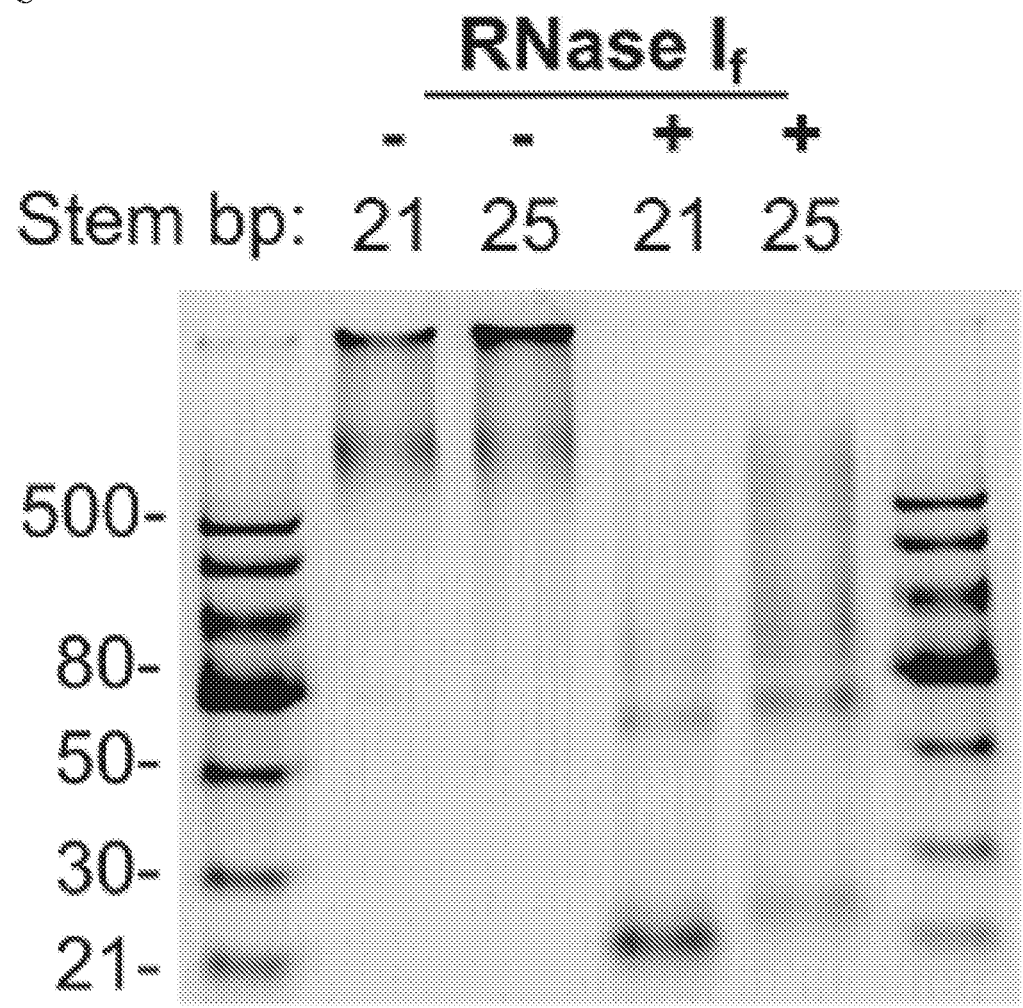
Figure 3:
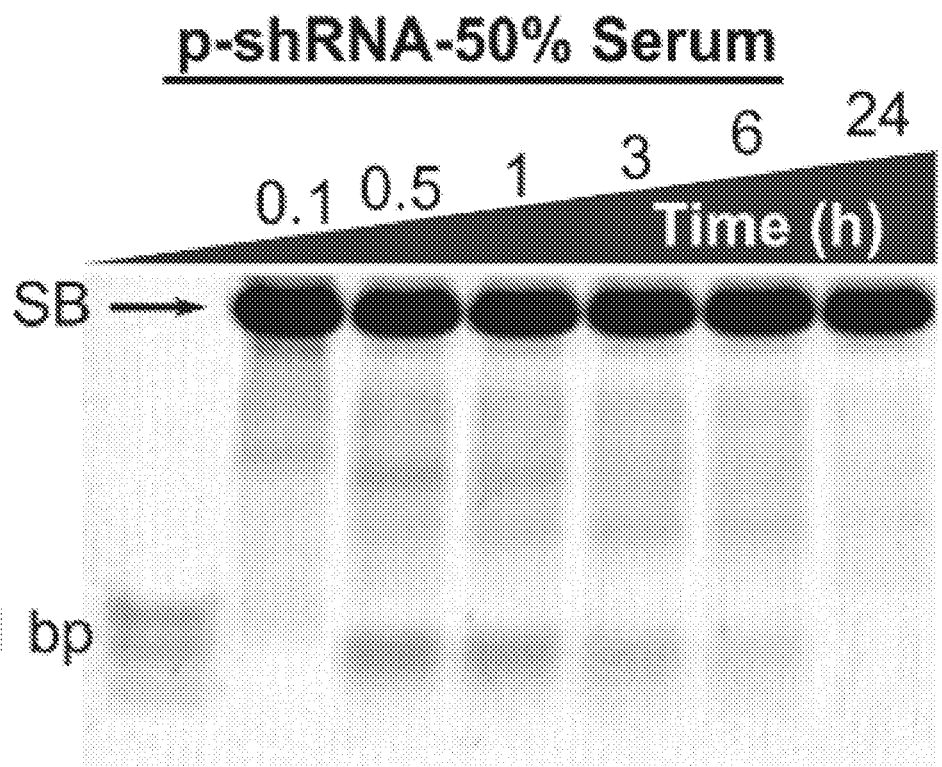
Figure 3:
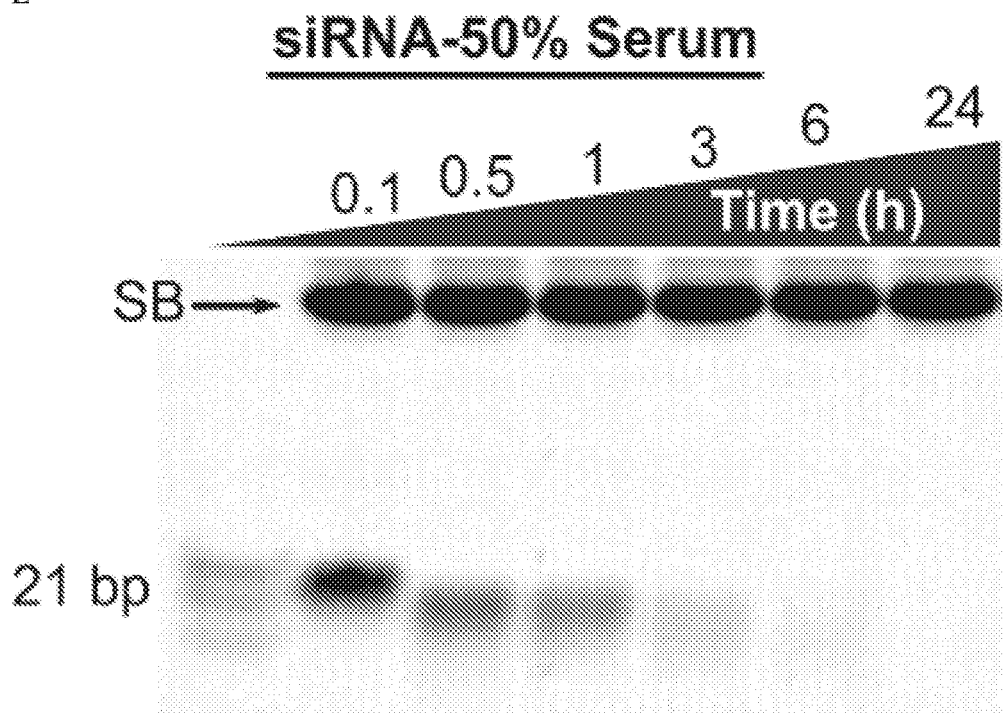
Figure 4:
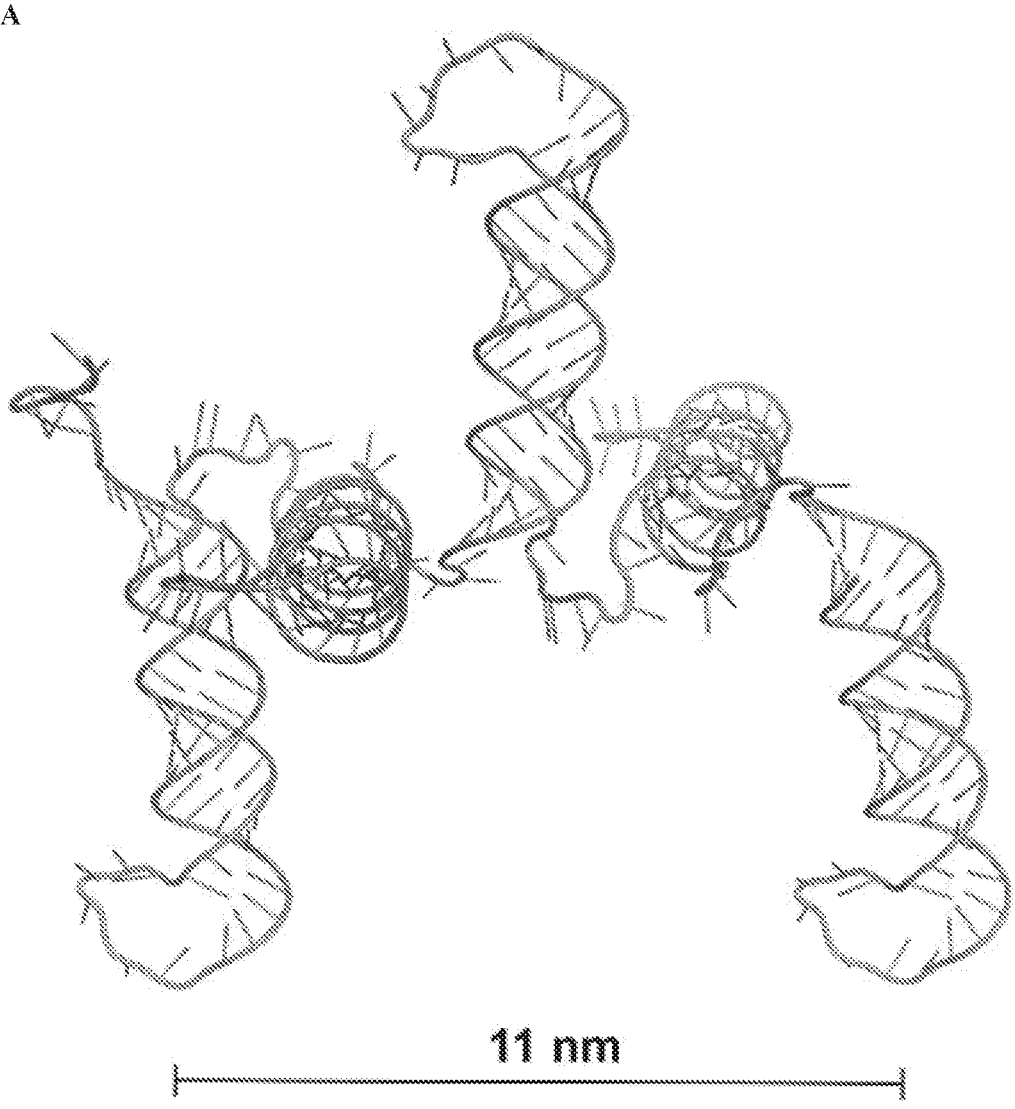
FIG. 4, Panels (A) and (B) are graphics depicting side and front views of a 3D model based on the secondary structure of p-shRNA (5 repeats) predicted to form through co-transcriptional folding.
Figure 4:
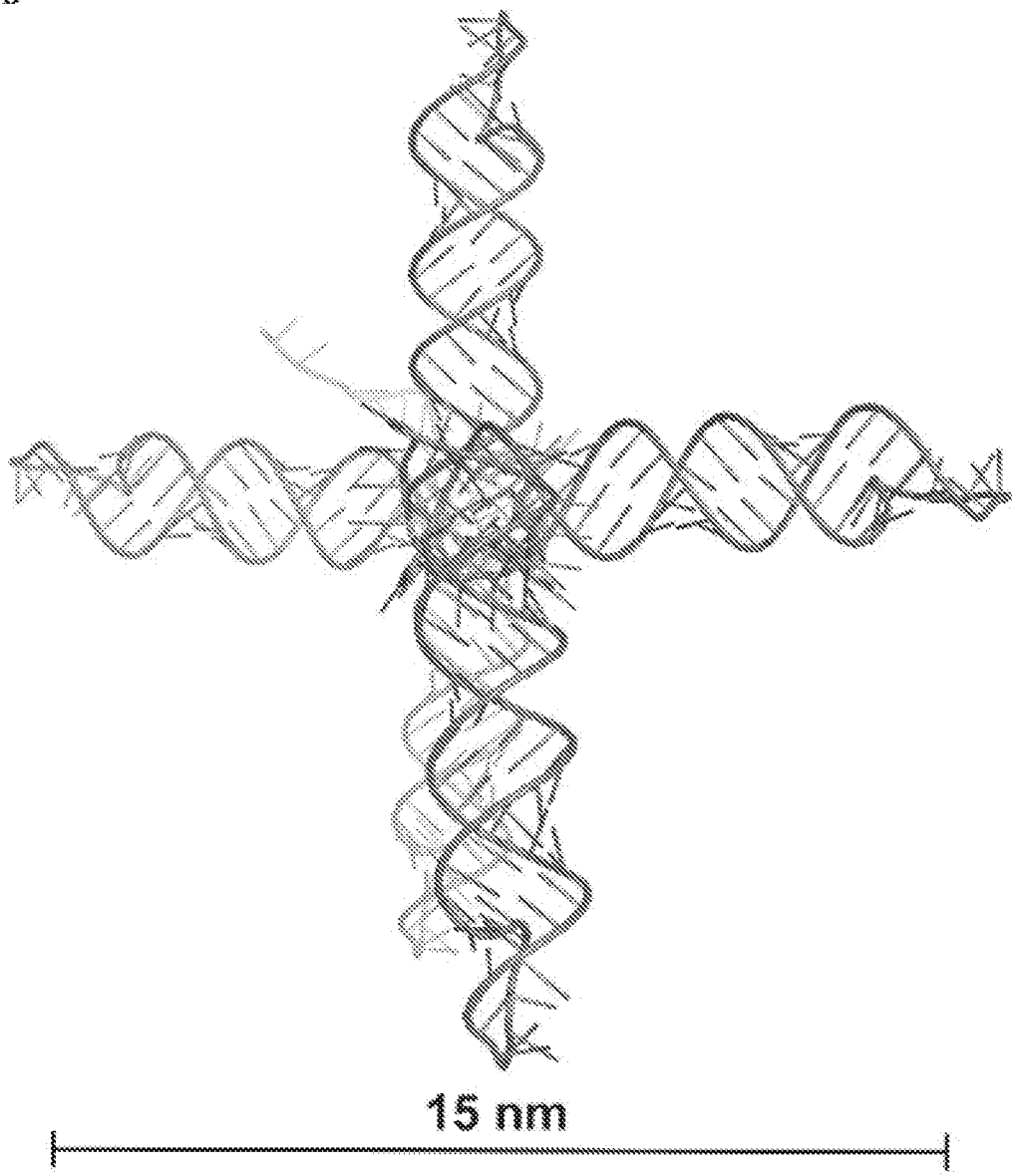
Figure 4C:
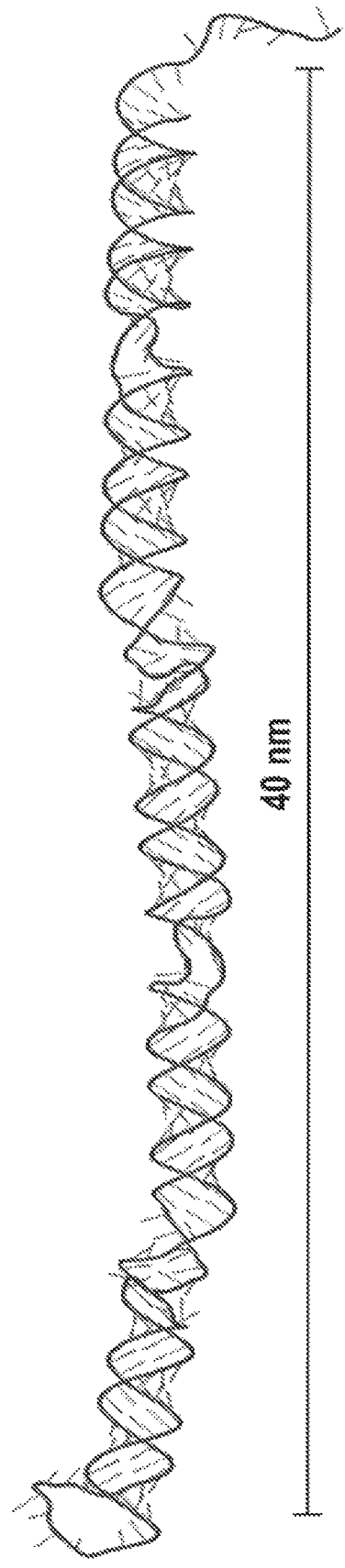
Figure 13:
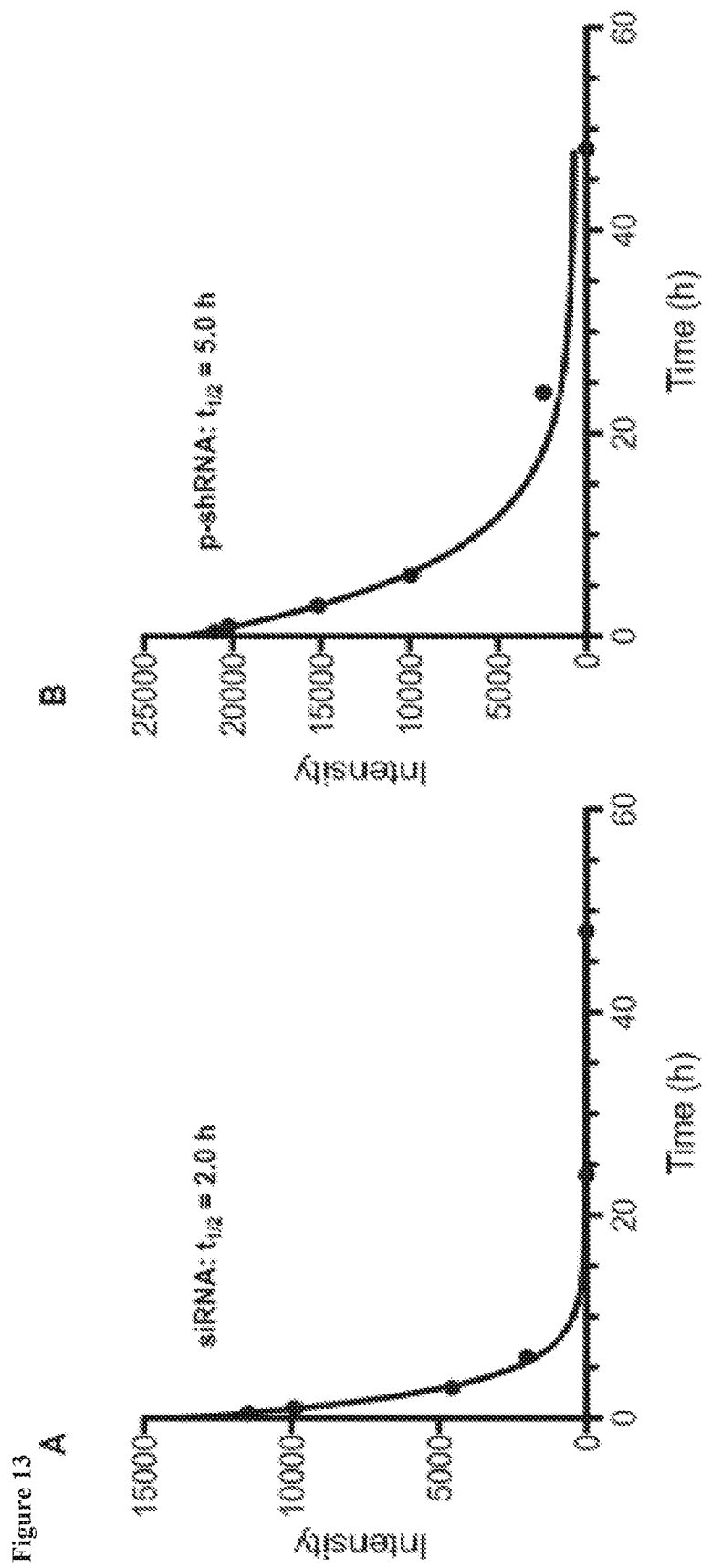
FIG. 13, Panels (A) and (B) are graphs depicting an degradation kinetics of siRNA (Panel (A)) and csiRNA (Panel (B)) in 50% human serum. Intensity corresponds to the 21 bp band intensity quantified with Image J from the gels shown in FIG. 2D-E.
Figure 13C:
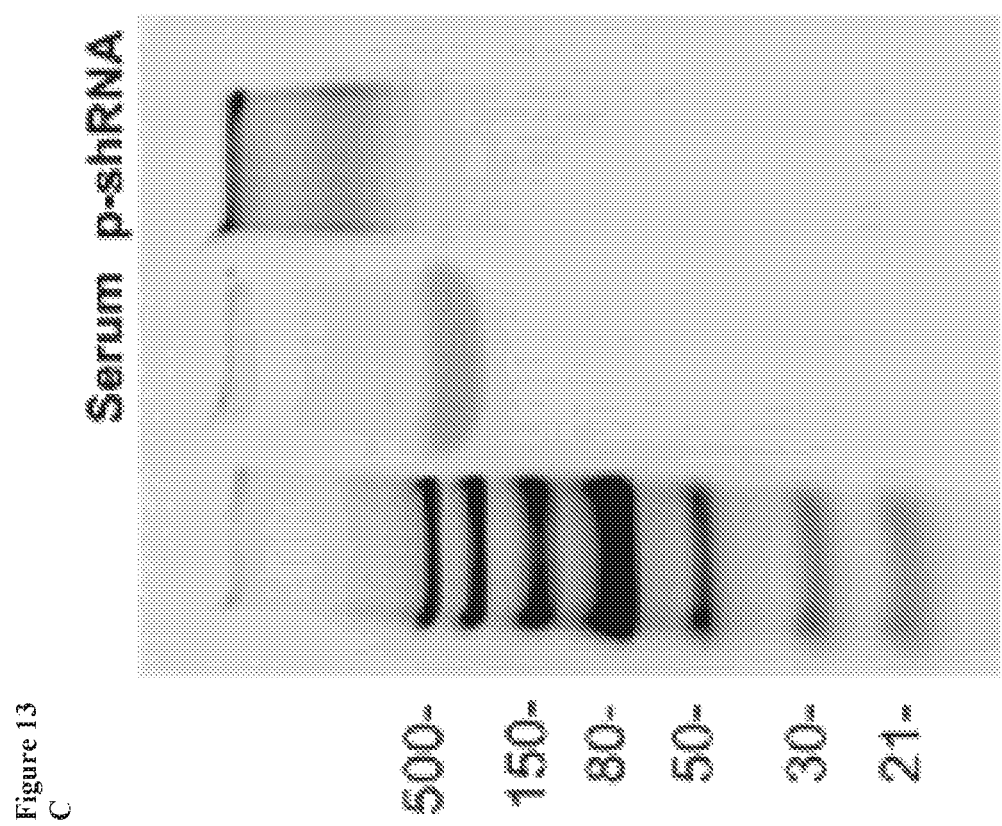

The secondary structure of the RNA molecules produced by RCT were characterized using circular dichroism (CD) and enzymatic digests, focusing on RNA produced from template 6 (GFP-10a). FIG. 3, Panels (A)-(B) shows CD spectra for p-shRNA and a 21 bp siRNA for comparison. The spectra for the two samples have similar shapes and normalized peak intensities, which are consistent with the A-form double helical structure expected for dsRNA. However, differences between the p-shRNA and siRNA spectra were observed upon heating the samples to 95° C. As expected, the siRNA sample underwent a sharp melting transition at ~65° C. (monitored at 210 nm) (Lesnik, E et al. (1995) *Biochemistry* 34: 10807-15); in contrast, p-shRNA showed a near-linear, loss of order with increased temperature, and appeared to retain some of its secondary structure up to 95° C. Digesting p-shRNA with RNase I, which is selective for ssRNA, yielded products consistent with the predicted secondary structure of alternating single-stranded and double-stranded regions. p-shRNAs predicted to have 21 and 25 bp double-strand regions (p-shRNA-21 and p-shRNA-25; synthesized from templates 6 and 12) were treated with RNase I: following 15 minutes, prominent bands at 21 and 25 bp, respectively, were observed (FIG. 3, Panel (C)). Treatment of the 21 bp p-shRNA with 50% human serum resulted in a similar banding pattern compared with RNase I treatment. FIG. 3, Panel (D) shows the appearance of a prominent 21 bp band—along with other larger fragments—within 30 minutes; the 21 bp band subsequently decreased in intensity over the course of the experiment. Degradation half-lives were calculated for siRNA and the 21 bp fragment derived from p-shRNA by image densitometry, which gave values of 2.0 h and 5.0 h, respectively (FIG. 13). Although the 21 bp p-shRNA fragment is expected to degrade at the same rate as 21 bp siRNA, p-shRNA must first be broken down from larger fragments: these appear to be degraded more slowly than siRNA, and thereby prolong the effective serum half-life of p-shRNA compared to siRNA.

p-shRNA molecules can potentially fold into several different structures that are consistent with the above results. The predicted MFE structure for p-shRNAs involves the entire molecule folded back on itself, as depicted in FIG. 4, Panel (A); however, the realization of this MFE structure is unlikely since p-shRNA folding is expected to occur co-transcriptionally. CoFold—a free energy minimization algorithm that takes folding kinetics into account—to model p-shRNA folding was used (Proctor, J R et al. (2013) *Nucleic Acids Res* 41: 1-11). Folding predictions were performed for 2-6 repeats of a p-shRNA sequence with symmetric 10-base loops while varying the folding parameter τ (lower values of τ place a greater emphasis on kinetic control of folding) and using the Turner (1999) energy parameters. The simple periodic hairpin structure shown in FIG. 4, Panel (A) was predicted across a wide range of τ values including the default value of 640, which was previously optimized for predicting the folded structure of large RNAs (Proctor, J R et al. (2013) *Nucleic Acids Res* 41: 1-11). It was noted that this structure is predicted to be only ~1 kcal/mol/repeat higher in energy than the MFE prediction using the same energy parameters. The 3D structures for the periodic hairpin and MFE structures are unique in their dimensions, with five repeats of the co-transcriptionally folded structure measuring 11 nm×15 nm compared to 40 nm×3 nm for the minimum free energy structure. Notably, the MFE structure appears similar to a conventional dsRNA, whereas the co-transcriptionally folded structure is considerably different. Increasing τ to roughly double or triple the default value gave structures with double- and triple-hairpins through further back-folding of the RNA molecule. This suggests that the simple periodic hairpin arrangement likely predominates, but a mixture of further back-folded structures could be present depending on the rates of transcription and folding.

Figure 5:
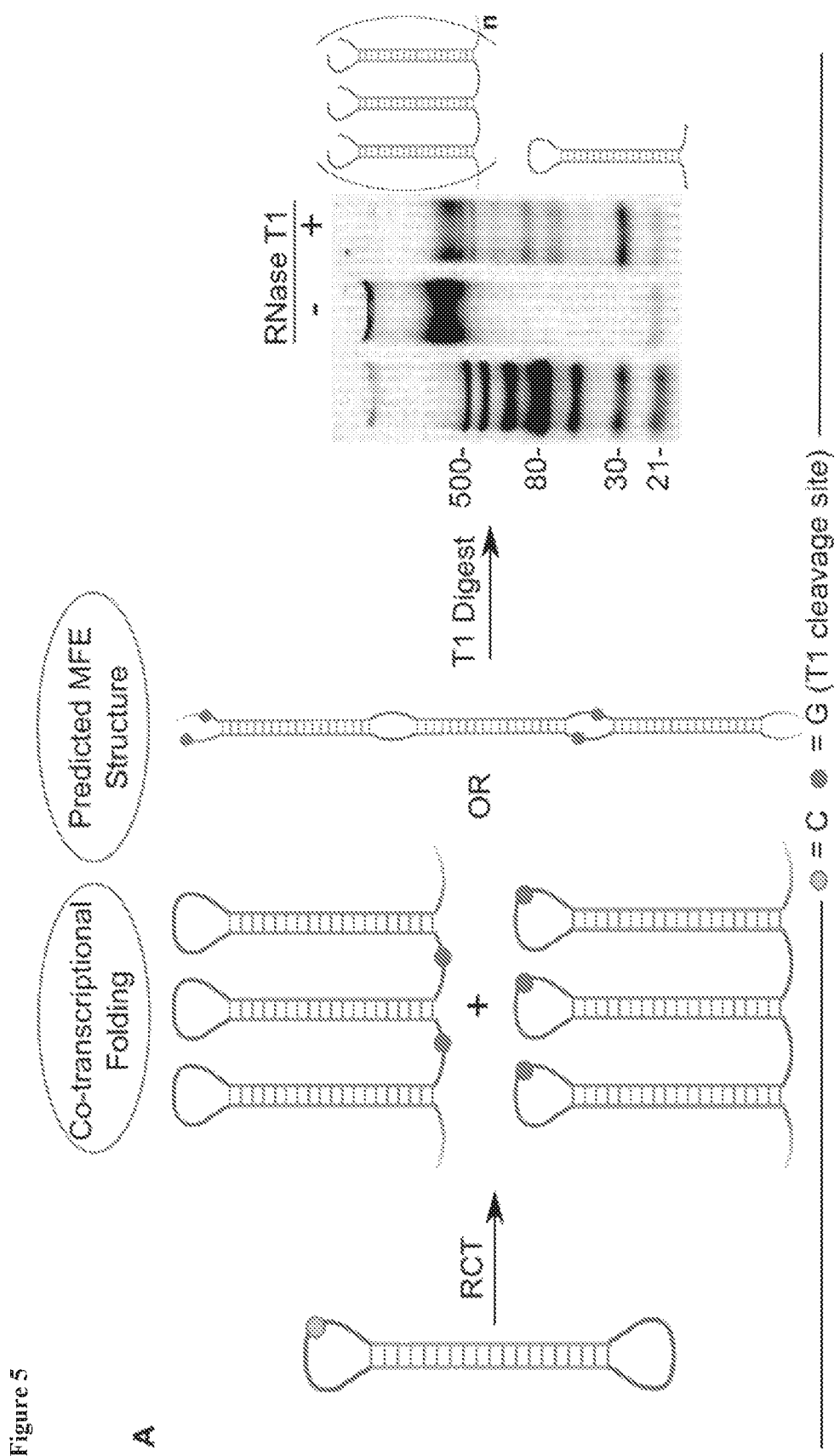
FIG. 5, Panel (A) are schematic diagram and native PAGE gel (15% TBE) depicting T1 digest of p-shRNA derived from template 7 (one C in one loop). The gel shows prominent bands corresponding to knicked, intact p-shRNA (>500 bp) and a single hairpin unit (~30 bp).
Figure 5:
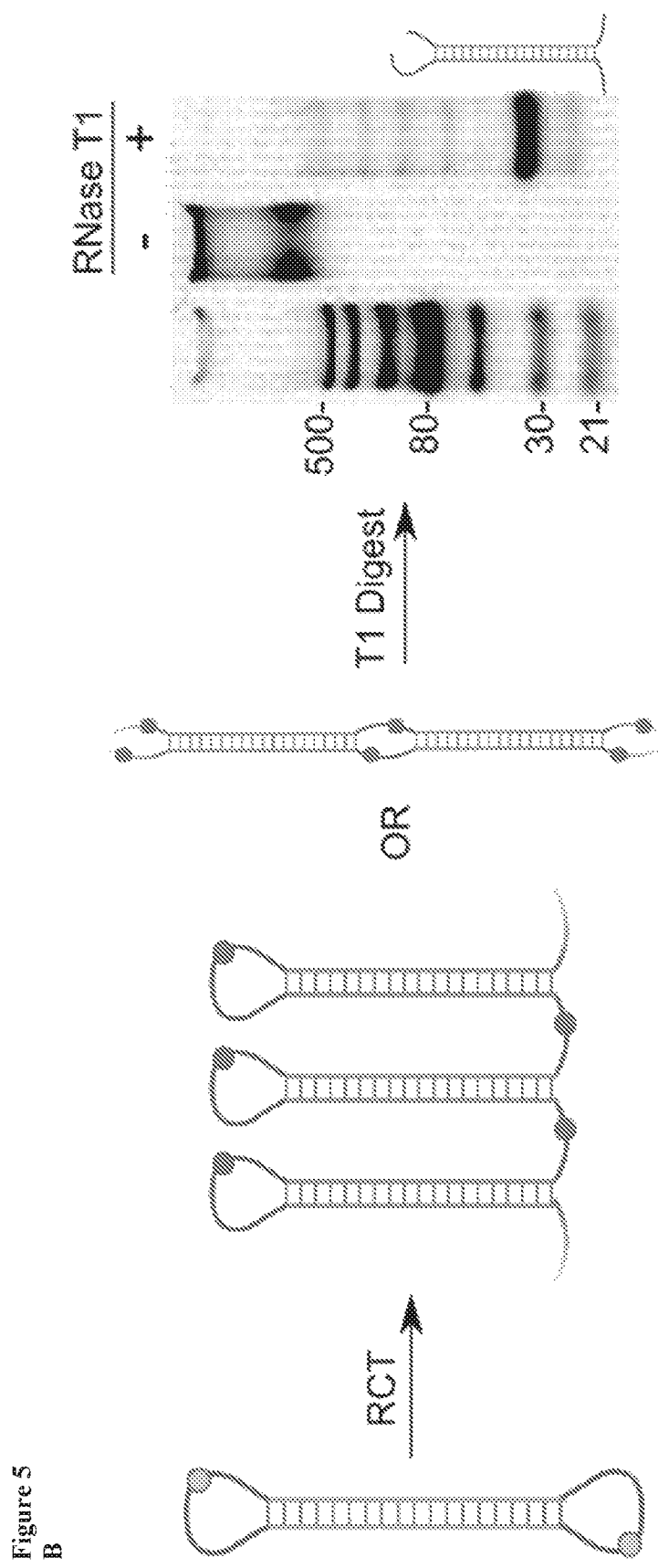

RNase T1—which selectively cleaves ssRNA 3' to guanines—was next used to distinguish between the different predicted folded structures of p-shRNA. A DNA template was used with two different 10-base loops—one containing a single cytosine and the other lacking cytosines (template 7)—to give p-shRNA with one loop containing a single guanine and the other loop without any guanines. Since this template had equally sized loops with nearly identical sequences, it was predicted that transcription would initiate randomly from either loop leading to the two co-transcriptionally folded structures shown in FIG. 5, Panel (A). Treatment of these RNA products with RNase T1 would then either cleave at the top of the hairpin loop or at the bottom of the stem, theoretically yielding a 1:1 mixture of intact p-shRNA and a band near 30 bp under non-denaturing conditions. In contrast, periodic double- or triple-hairpin structures would lead to a larger fraction of ~60 bp fragments and smaller amounts of single hairpin fragments and "trimmed" periodic RNA; RNase T1 treatment of the predicted MFE structure should lead almost entirely to ~60 bp fragments. The results of the experiment are shown in FIG.

Figure 14:
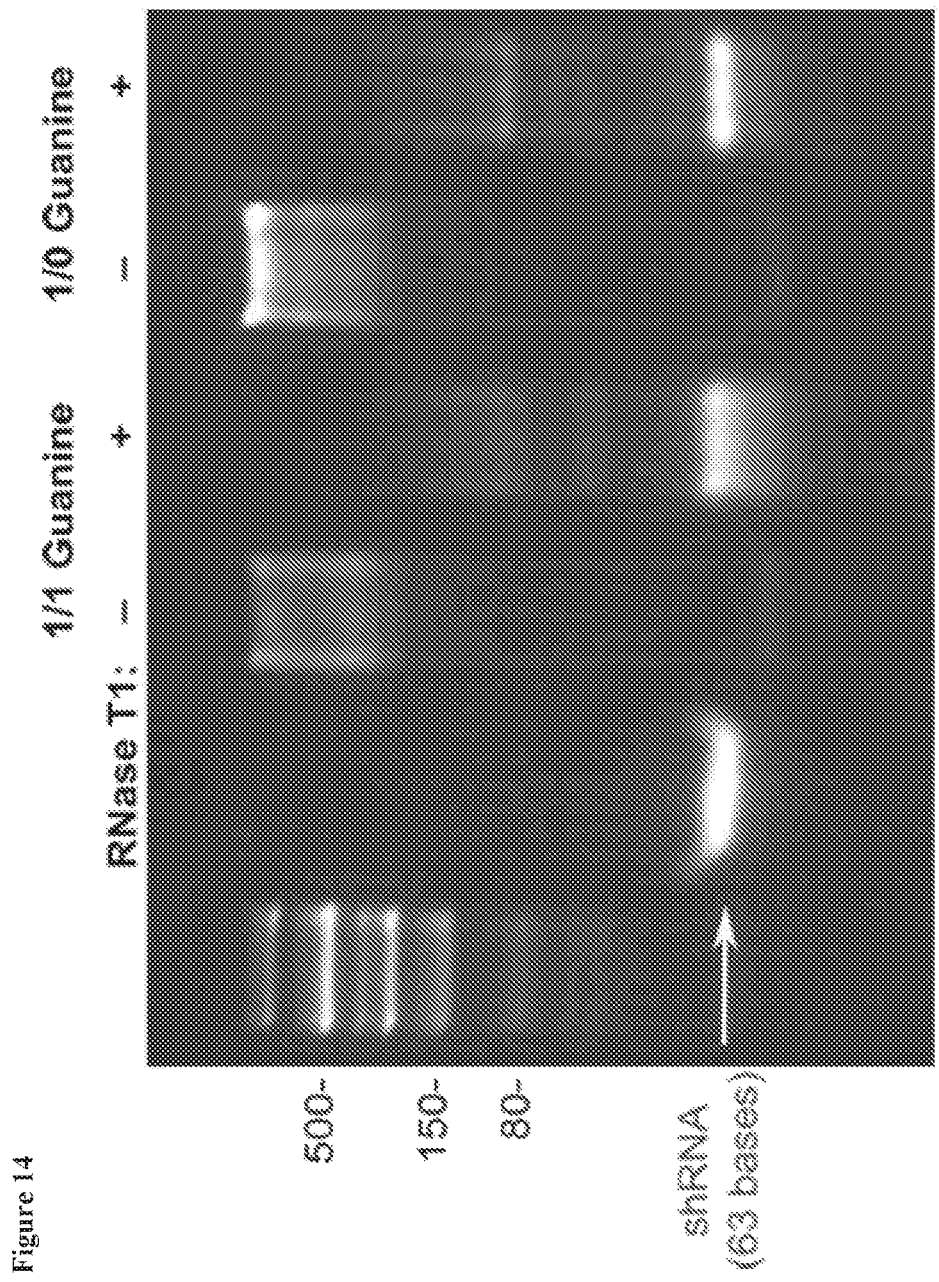
FIG. 14 is a photograph depicting a denaturing PAGE gel (15%, TBE-Urea) of p-shRNA from templates 6 and 7, with and without RNase T1 treatment.
Figure 15:
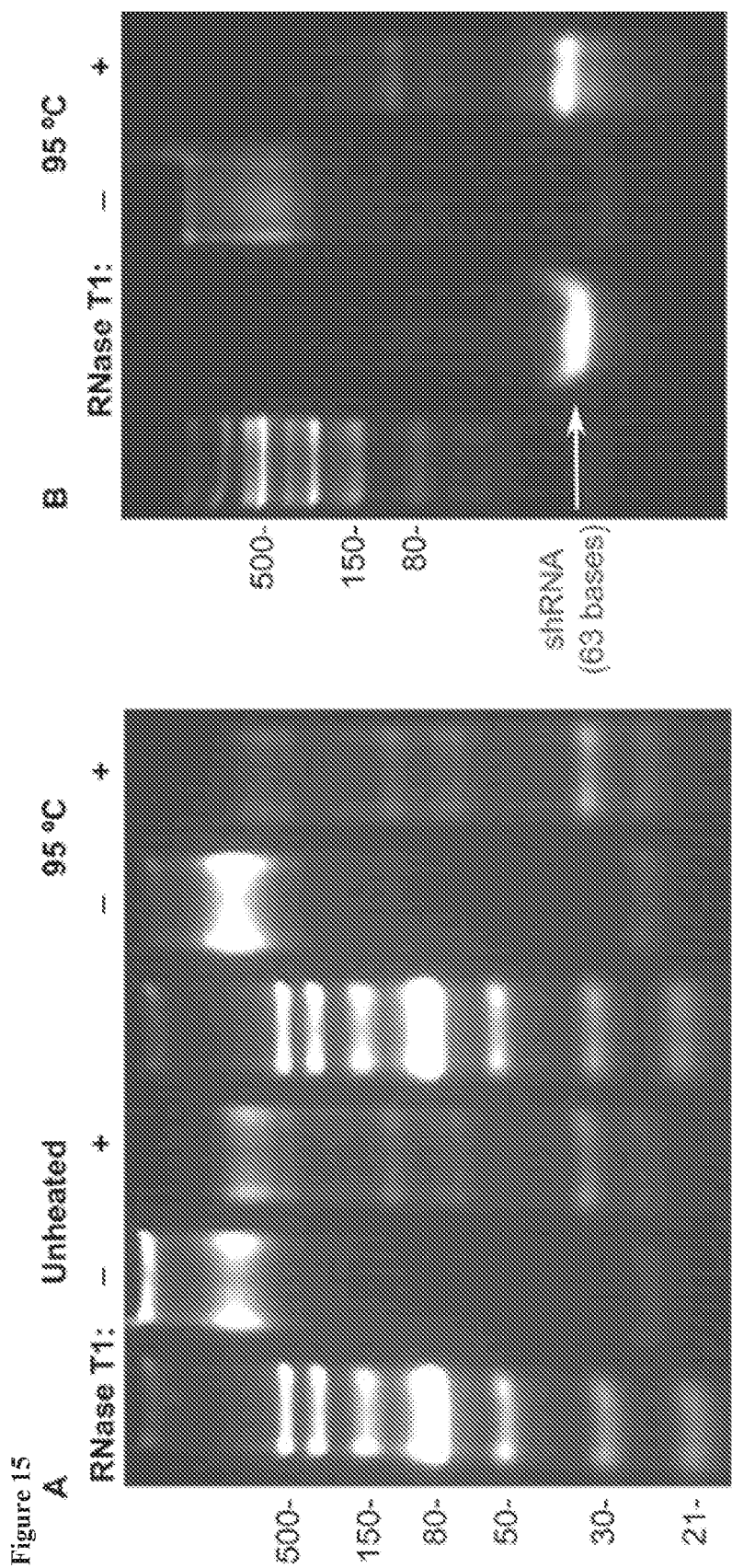
FIG. 15, Panels (A) and (B) are photographs depicting the results of RNase T1 treatment of p-shRNA (from template 7) after heating to 95° C.
Figure 16:
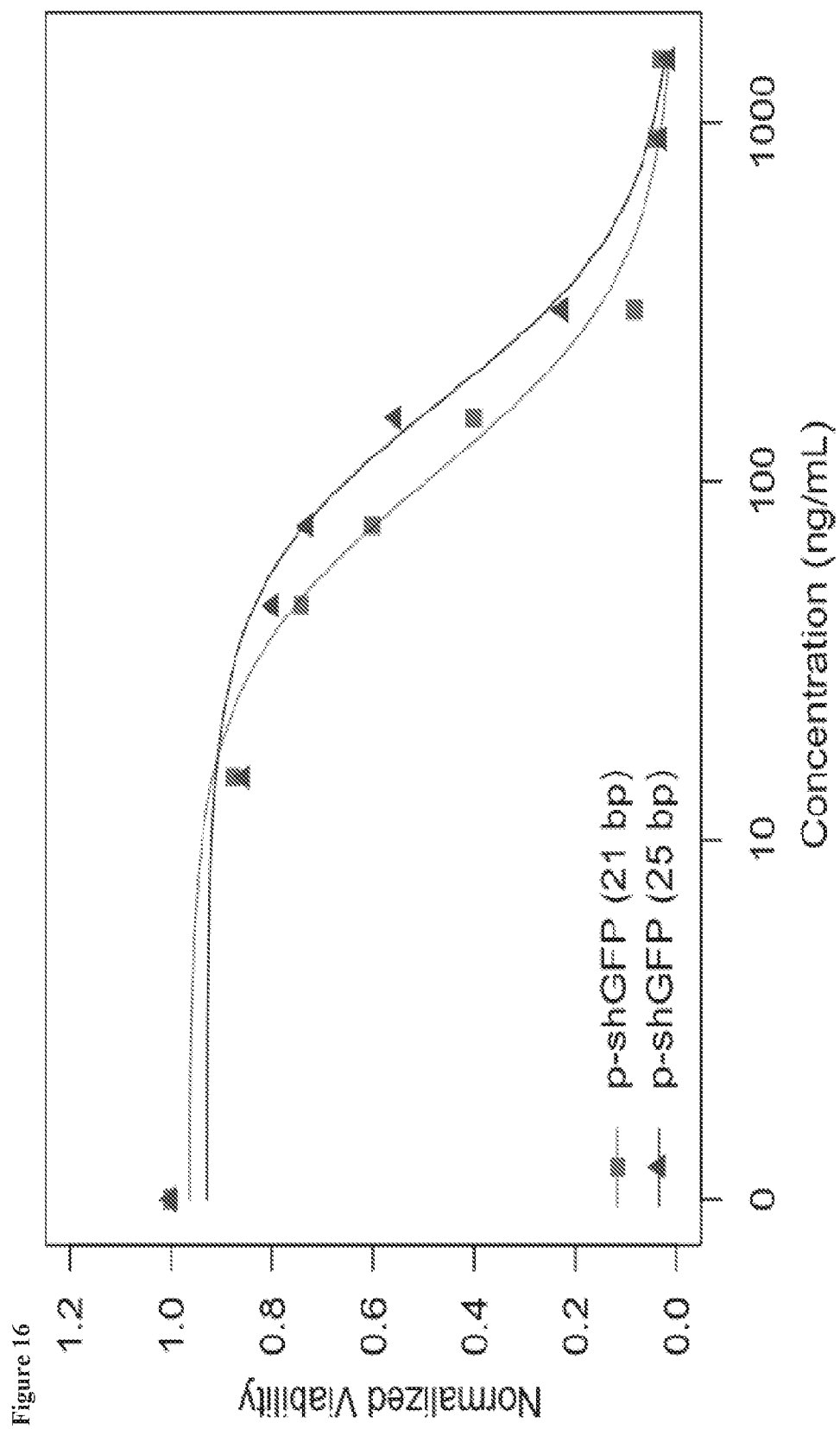
FIG. 16 is a graph depicting cell viability curves for SKOV3 cells treated with 21 bp (from template 6) and 25 bp p-shRNA (from template 9) delivered with Lipofectamine 2000.
Figure 19:
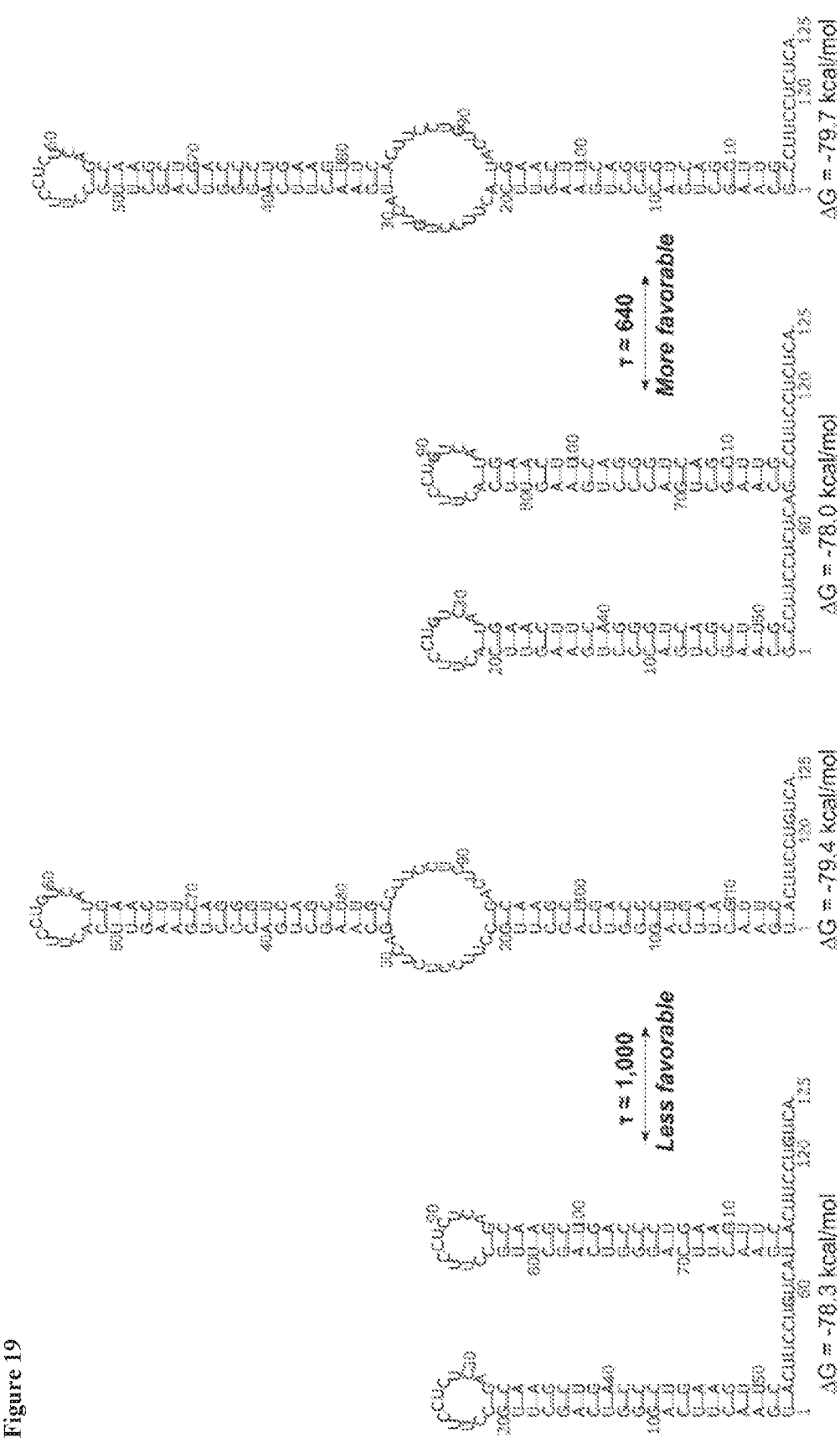
FIG. 19 is a schematic representation depicting two possible scenarios corresponding to initiation at the different loops. These schematics aim to show when attempts were made to refold p-shRNA derived from template 7 leading to a substantial increase in the relative amount of single hairpins produced with RNase T1 treatment. According to the CoFold folding predictions, the transition from a single hairpin to double hairpin structure is more kinetically favorable for the p-shRNA with Gs in the hairpin loops vs. p-shRNA with Gs in the linker region (lower value of τ where back-folded structure becomes favored). A scenario was proposed where the major products after thermal refolding are those on the far left and far right of the above diagram, which are predicted to give a product distribution similar to what was observed experimentally (i.e., mostly single hairpins with some larger fragments).
Figure 20:
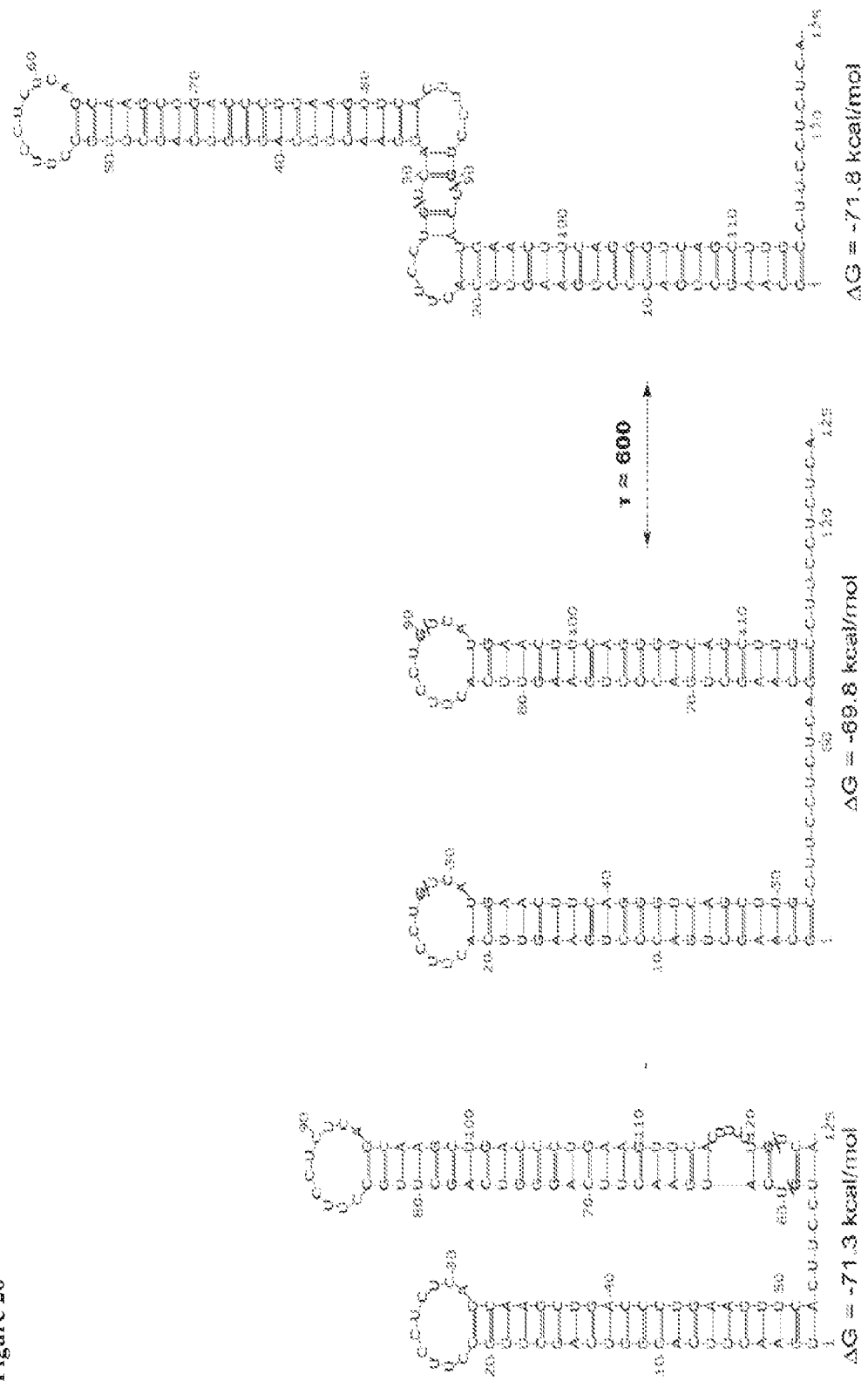
FIG. 20 is a schematic representation depicting additional base pairing in linker regions predicted for p-shRNA derived from template 7 when using the Andrenescu-2007 A-parameters in place of the Turner-1999 T-parameters available to model folding with CoFold. With these additional base pairs, the structure with Gs at the bottom is further stabilized relative to the structure with Gs on top, and refolding to a more back-folded structure becomes even less kinetically favored for the structure on the left. On the other hand, the transition from the structure with Gs on top to the double-hairpin structure is now slightly more favorable, due to the new base pairs introduced upon refolding. These extra base pairs involve the RNase T1 cleavage sites, which are known from experiments must be labile. However, in other experiments (unpublished results), it was observed that base-paired Gs adjacent to 3' single-stranded regions were still cleaved by RNase T1; as this would be the case in the above structures, they could still be consistent with observations made herein.

4 and agree well with the predictions for the simple co-transcriptionally folded structure. Following treatment with RNase T1, a prominent band at 30 bp (corresponding to a single hairpin) was observed, two faint bands at ~60 and 90 bp (corresponding to two/three hairpins), and a group of bands>500 bp that migrated alongside the untreated sample. Integration of these bands (>500 bp vs. 30/60/90 bp bands) gave close to the predicted 1:1 ratio (measured=0.9±0.2). An otherwise identical RNA with a G in both loops (from template 6) was almost completely broken down into 30 bp fragments under the same conditions; some higher order bands were again apparent, suggesting that these are the result of incomplete digestion (FIG. 5, Panel (B)). Denaturing PAGE gels of the above products were virtually identical, both showing one major band corresponding to the length of a single hairpin repeat (FIG. 14); this result confirms that the apparently intact p-shRNA in FIG. 5, Panel (A) was indeed nicked. Lastly, an attempt was made to convert the p-shRNA from FIG. 5, Panel (A) to a lower energy structure by heating to 95° C. and slowly cooling back to room temperature. Treating this "refolded" p-shRNA with RNase T1 gave a similar banding pattern, however, the relative intensity of the intact p-shRNA band compared to the shorter bands was around three times less than observed for the original p-shRNA sample (ratio=0.3±0.1; FIG. 15). While this result is inconsistent with the predicted MFE structure, it suggests that some structural rearrangement of p-shRNA occurred upon heating (see FIGS. 19-20).

3. Cytotoxicity, Silencing Activity, and Immunostimulation

The toxicity of large dsRNA in cancer cells has been largely attributed to TLR3 (Salaun, B et al. (2006) *J Immunol* 176: 4894-4901; Jiang, Q et al. (2008) *BMC Cancer* 8: 12) and the cytosolic PRRs RIG-I/MDA5, particularly when dsRNA is delivered with transfection reagents (Besch, R et al. (2009) *J Clin Invest* 119: 2399-2411; Ktibler, K et al. (2011) *Eur J Immunol* 41: 3028-39; Liu, J et al. (2012) *Exp Hematol* 40: 330-341; Duewell, P et al. (2014) *Cell Death Differ* 21: 1825-1837). The cytotoxicity of p-shRNA in HeLa cells was tested when delivered with Lipofectamine as a function of p-shRNA length (FIG. 6, Panel (A)). Intact p-shRNA (21 bp) delivered with Lipofectamine caused a concentration-dependent decrease in cell viability with an $IC_{50}$ value of 110 ng/mL. When p-shRNA was first broken down into small fragments (by treating with RNase T1) it was ~4-fold less potent, with an $IC_{50}$ value of 461 ng/mL. For comparison, a 21 bp siRNA with the same dsRNA sequence as the p-shRNA was much less toxic than the enzymatically digested p-shRNA when delivered with Lipofectamine ($IC_{50}$>1500 ng/mL). Lipofectamine on its own was also found to be non-toxic to HeLa cells when administered at the same concentrations without RNA (data not shown).

The dose-response behavior for the lipofection of p-shRNA and HMW poly-I:C were compared in a panel of cancer cell lines (HeLa, A549, SKOV3, and UCI101) and NIH-3T3 fibroblasts. Two different p-shRNAs were tested with 21 or 25 bp ds-regions (from templates 17 and 18; referred to here as p-shRNA-21 and p-shRNA-25). Overall, poly-I:C and p-shRNA-25 were found to be similarly cytotoxic (FIG. 6, Panel (B)), and p-shRNA25 was ~two-fold more potent than p-shRNA-21. Out of the different cell lines tested, the lowest p-shRNA and poly-I:C toxicities were observed in 3T3 fibroblast cells. The $IC_{50}$ values for p-shRNA-21, p-shRNA-25, and poly-I:C in 3T3 cells were >1500, 880, and 711 ng/mL, respectively; in contrast the corresponding $IC_{50}$ values averaged across the cancer cell lines tested were 200, 75, and 129 ng/mL. It is important to note that in addition to having different ds-lengths, p-shRNA-21 and p-shRNA-25 also had unrelated sequences. To test whether ds-length was an important factor in determining p-shRNA cytotoxicity, another pair of 21 bp and 25 bp p-shRNA sequences was tested in SKOV3 cells (p-shGFP-21 and p-shGFP-25; from templates 6 and 12), which had identical sequences except for the four extra base pairs in the 25 bp p-shRNA. Of these two p-shRNAs, p-shGFP-21 was slightly more toxic to SKOV3 cells ($IC_{50}$=103 vs. 168 ng/mL, see Figure S9), suggesting that ds-length alone is not a strong predictor of cytotoxicity; however, different double-strand sequences do appear to have different potencies.

The cytotoxicity of lipofected poly-I:C was previously shown to proceed through a caspase-dependent apoptotic pathway in cancer cells (Besch, R et al. (2009) *J Clin Invest* 119: 2399-2411). Caspase activation in SKOV3 cells 14 h following treatment with p-shRNA-25 or poly-I:C delivered with Lipofectamine was compared (FIG. 6, Panel (D)). Both poly-I:C and p-shRNA-25 caused significant increases in caspase 3/7, caspase 8, and caspase 9 relative to untreated cells, suggesting that p-shRNA activates apoptotic pathways in a similar manner to poly-I:C following lipofection.

Figure 6:
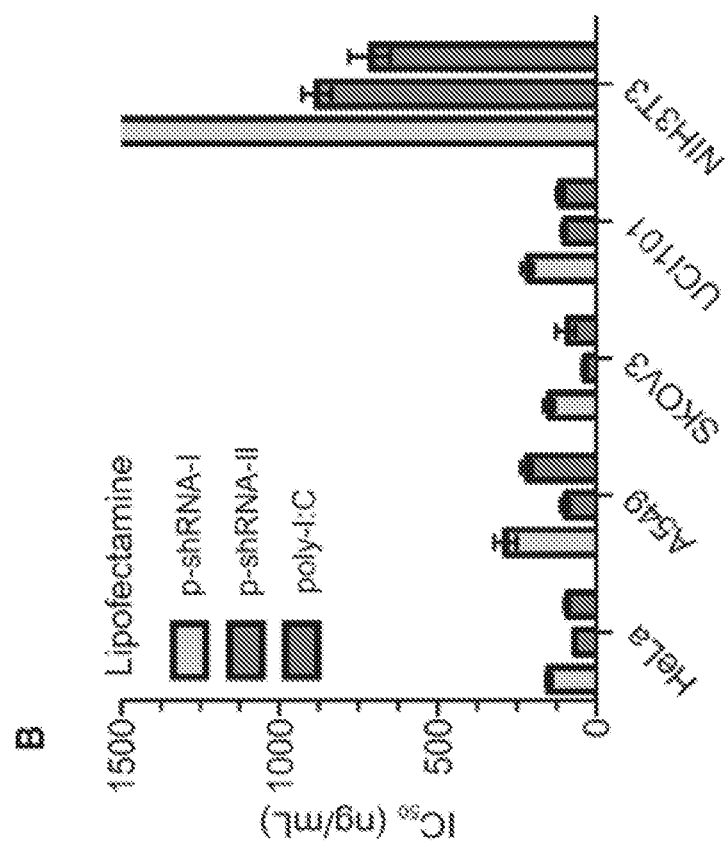
FIG. 6, Panel (A) is a graph depicting a cell viability dose-response curves for p-shRNA, RNase T1-digested p-shRNA, and siRNA delivered with Lipofectamine to HeLa cells. Viability was measured by the CellTiterGlo assay and normalized to untreated cells. p-shRNA for this experiment was derived from template 6.
Figure 6:
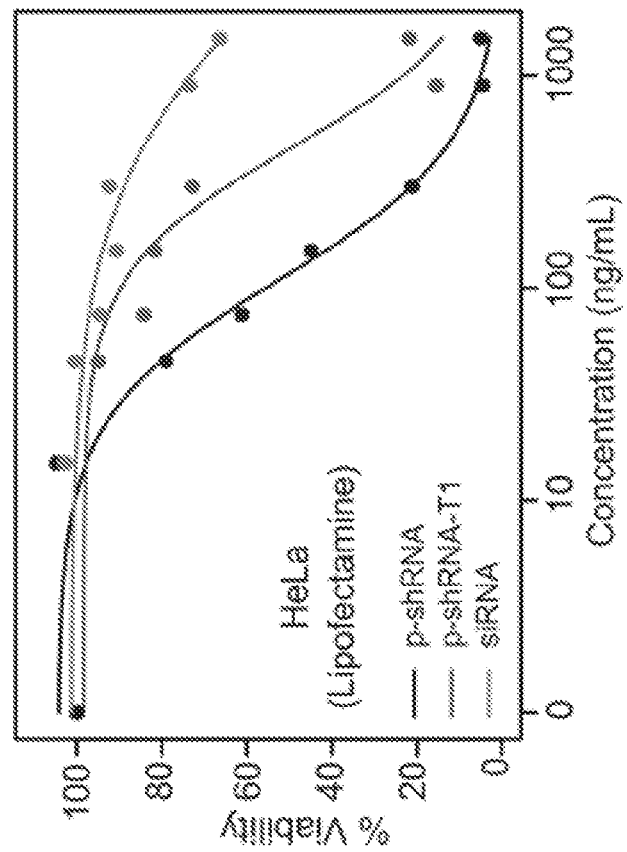
Figure 6:
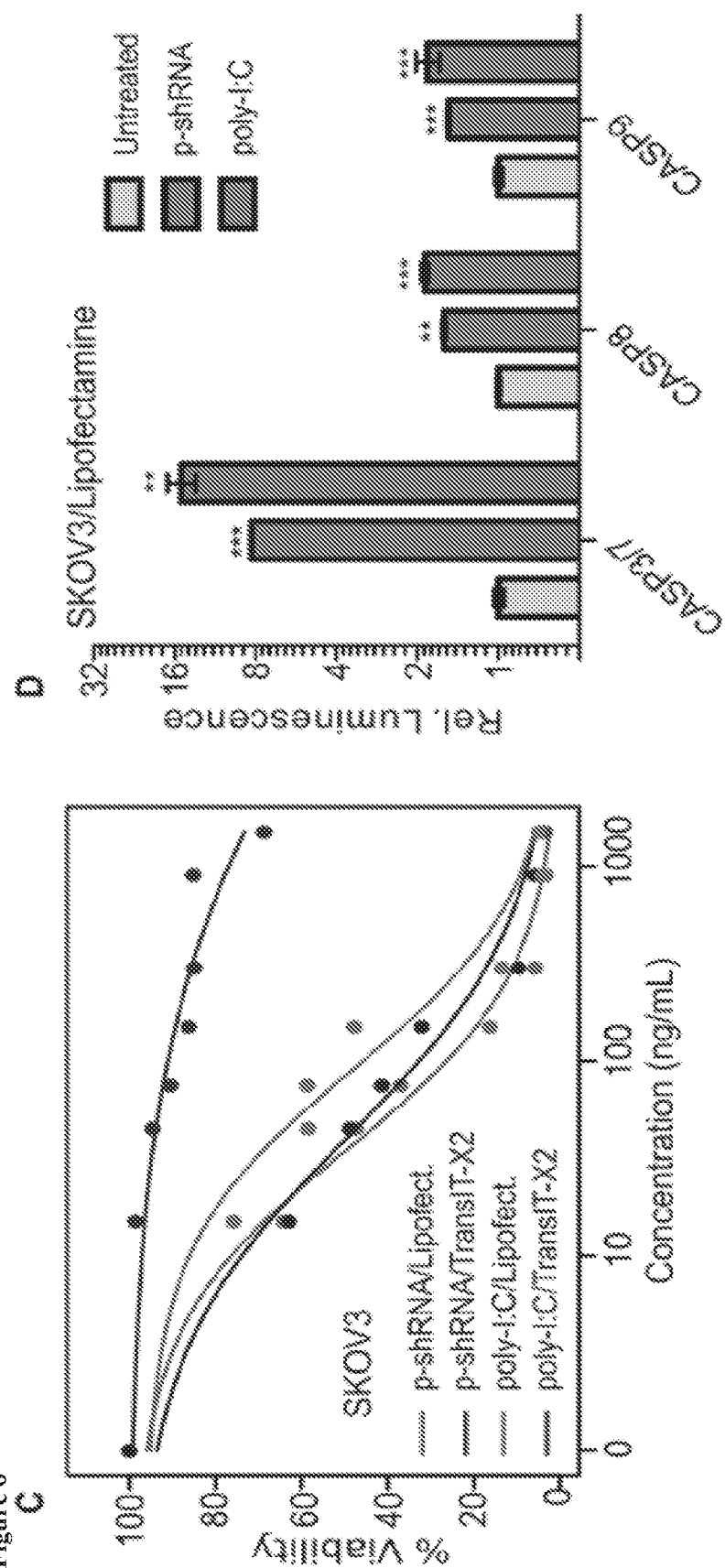
Figure 6:
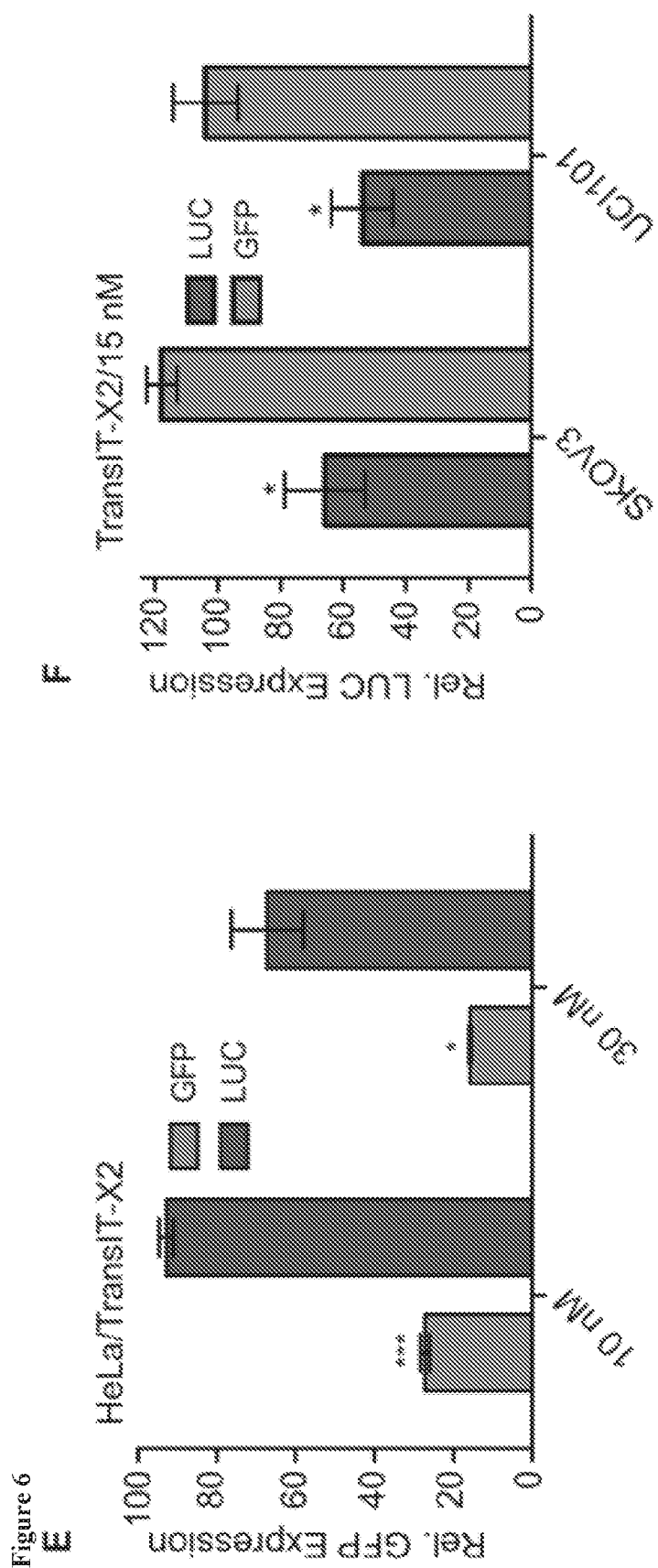

To test the generality of p-shRNA toxicity in cancer cells, the same four cancer cell lines were treated with p-shRNA-25 complexed to a polymeric transfection reagent (TransIT-X2). FIG. 6, Panel (C) shows the dose-response curves for p-shRNA-25 and poly-I:C delivered with TransIT-X2 or Lipofectamine in SKOV3 ovarian cancer cells. Notably, p-shRNA showed nearly identical toxicity when delivered with TransIT-X2, whereas poly-I:C was more than an order of magnitude less toxic when transfected with TransIT-X2 (>1500 ng/mL) compared to Lipofectamine. The average $IC_{50}$ value for p-shLUC-25 delivered with TransIT-X2 in the four cancer cell lines was 239 ng/mL; in contrast poly-I:C delivered with TransIT-X2 was moderately toxic to A549 cells ($IC_{50}$=947 ng/mL) and relatively nontoxic to all other cell lines ($IC_{50}$>1500 ng/mL).

Figure 17:
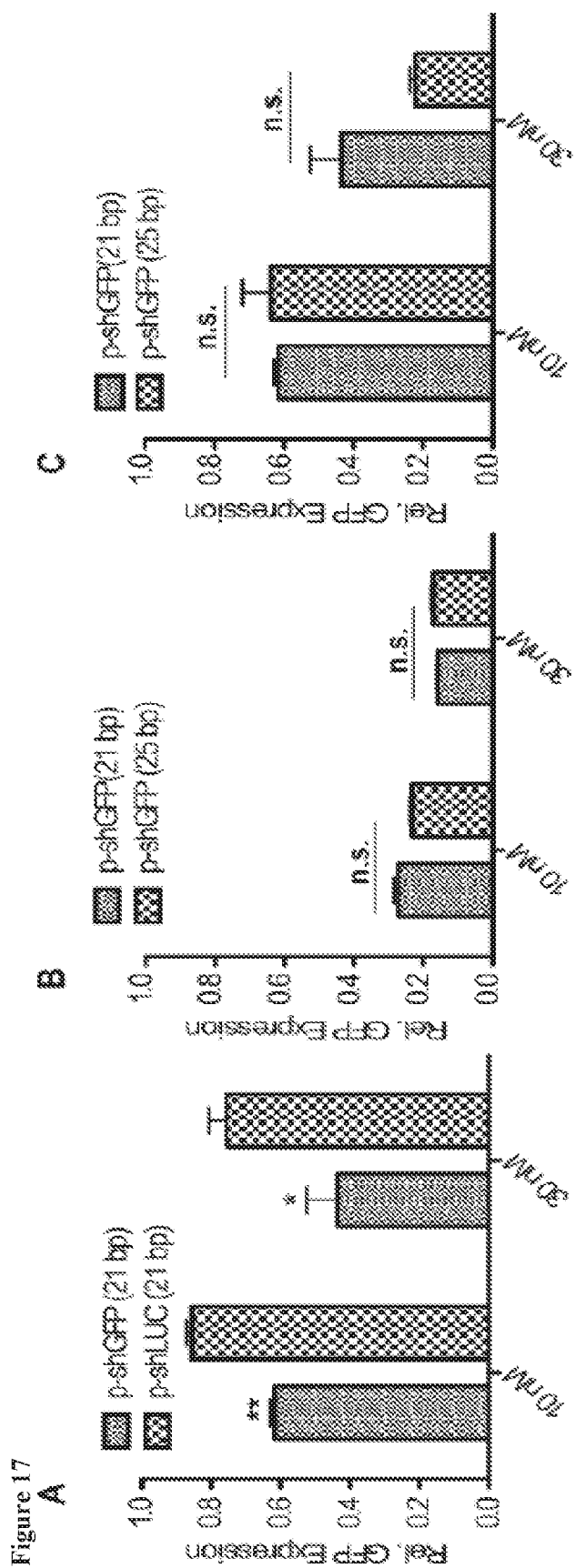
FIG. 17, Panels (A)-(C) are bar graphs depicting GFP knockdown in HeLa cells measured by flow cytometry (mean fluorescence).
Figure 18:
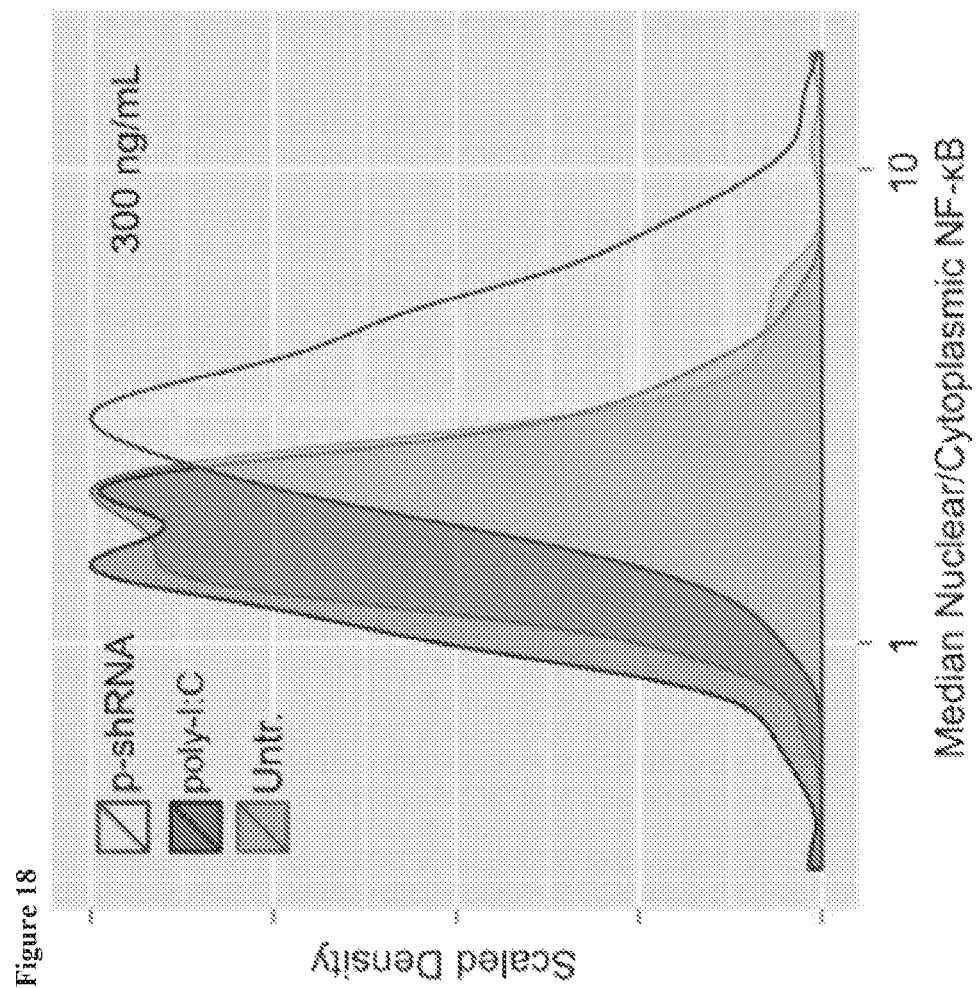
FIG. 18 is a graph depicting the nuclear localization of NF-κB quantified using Cell Profiler by taking the ratio of median NF-κB fluorescence in the nucleus divided by median NF-κB fluorescence in the cytoplasm for untreated cells or cells treated with 150 ng/mL RNA/Lipofectamine complexes.

Reporter gene knockdown using p-shRNA was initially measured in GFP-expressing HeLa cells (FIG. 6, Panel (E)). Using TransIT-X2, 73% and 84% GFP knockdown was observed relative to untreated cells for 10 and 30 nM p-shGFP-21 doses at 72 h (mean fluorescence measured by flow cytometry). Minimal non-specific knockdown was observed with the negative control p-shRNA (p-shLUC-21) at 10 nM, however, a 33% decrease in GFP expression was seen at the higher 30 nM dose. p-shRNA delivered with Lipofectamine also caused knockdown in HeLa cells, however, the effect size was smaller than with TransIT-X2 (48% and 56% knockdown at 10 nM and 30 nM doses; see FIG. 17, Panel (A)). p-shRNA with a 25 bp stem (p-shGFP-25) was also effective at causing knockdown in HeLa cells, with no significant differences in activity observed relative to p-shGFP-21 (FIG. 17, Panels (B)-(C)). Knockdown with TransIT-X2 was also tested in luciferase-expressing SKOV3 and UCI101 ovarian cancer cells using 25 bp p-shRNA derived from template 19. In both cell lines, 50-60% knockdown was observed relative to untreated cells at a 15 nM dose (measured as luminescence signal normalized to total protein); this knockdown was significant (p<0.05) compared to cells treated with negative control p-shRNA (containing an siGFP sequence; transcribed from template 20).

Figure 7:
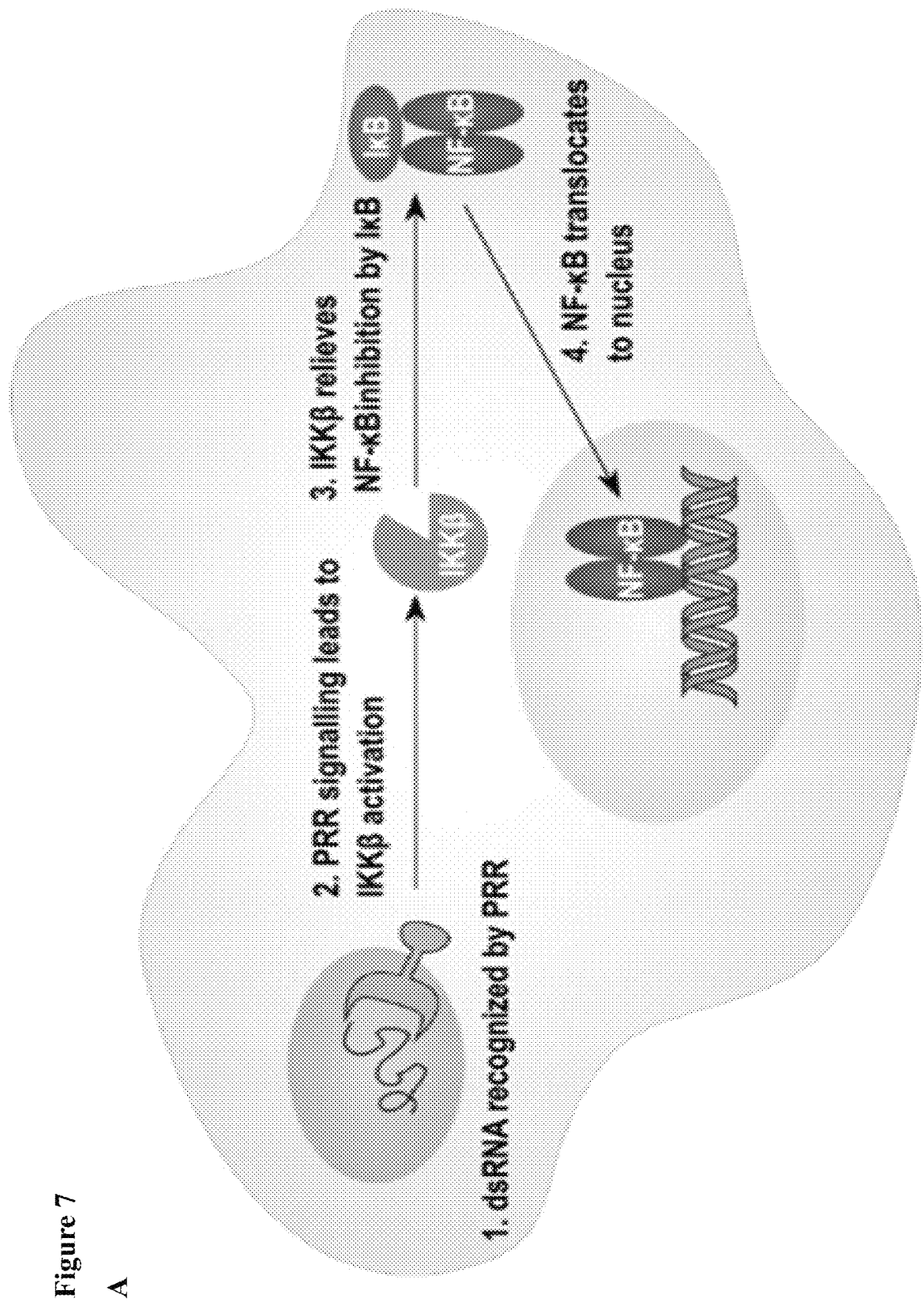
FIG. 7, Panel A is a carton depiction showing that NF-κB is activated by dsRNA through pattern recognition receptor (PRR)-mediated signaling, resulting in nuclear translocation and transcriptional activation of myriad genes.
Figure 7:
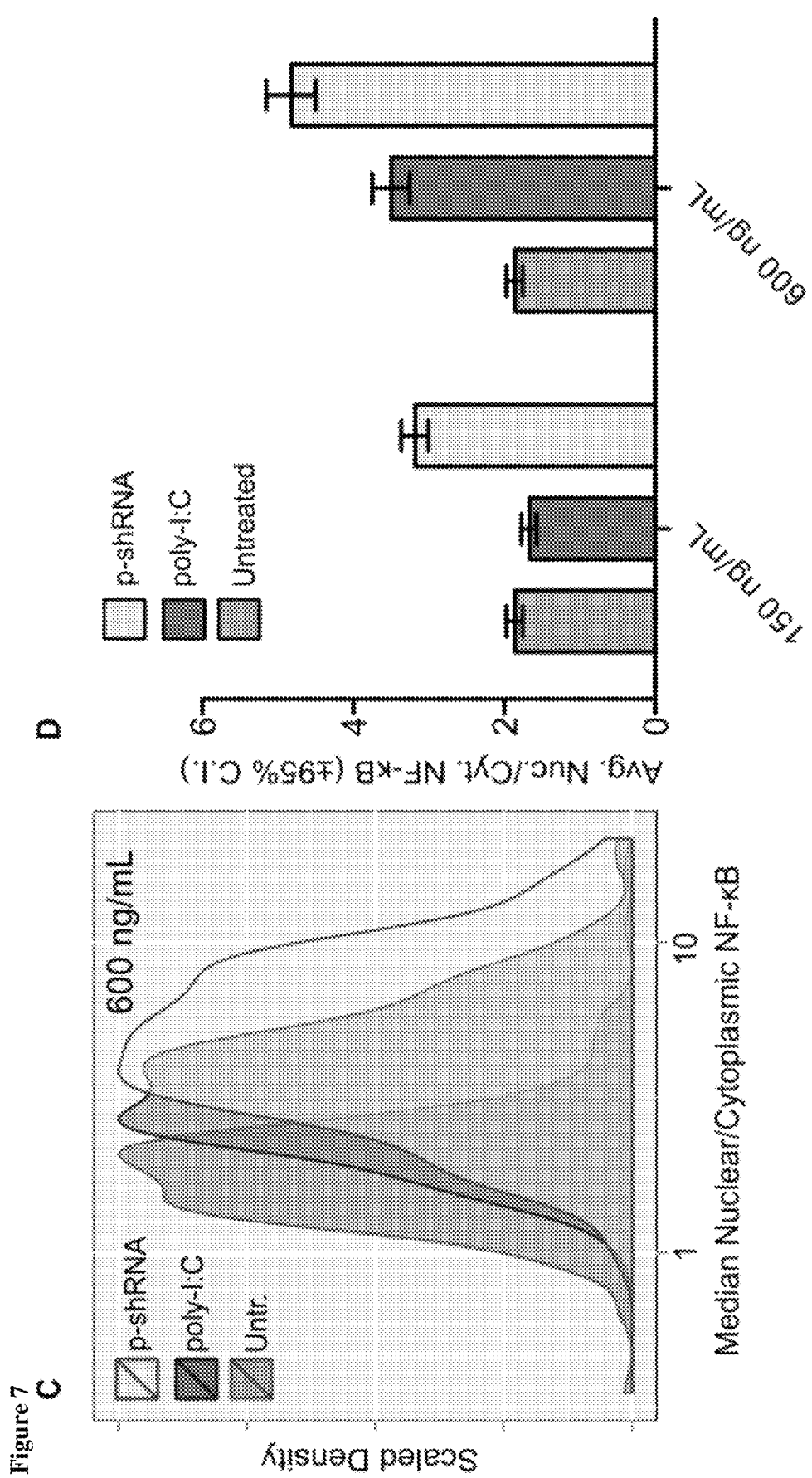

The activation and nuclear translocation of NF-κB is a canonical marker of innate immune stimulation (FIG. 7, Panel (A)). To test if p-shRNA transfection leads to NF-κB activation, SKOV3 cells were stained with AF488-labelled NF-κB antibody before and after transfection with p-shRNA-25/Lipofectamine and compared with poly-I:C as a positive control. Following stimulation with p-shRNA-25/Lipofectamine, an increase in nuclear NF-κB signal was apparent after 1 h, as evidenced by co-localization of the NF-κB stain with the DAPI nuclear stain (FIG. 7, Panel (B); yellow color indicates overlap). The extent of NF-κB nuclear translocation was quantified for untreated, p-shRNA treated, and poly-I:C treated cells by taking the ratio of median fluorescence inside the nucleus to median fluorescence in the cytoplasm. Based on this metric, a concentration-dependent shift was observed in the cell population to higher nuclear localization following p-shRNA transfection, with a 2.6-fold increase relative to untreated cells for cells treated at 600 ng/mL (FIG. 7, Panels (C)-(D)). The nuclear localization of NF-κB following p-shRNA treatment was greater than for poly-I:C (1.9-fold increase at 600 ng/mL), indicating that p-shRNA is a potent activator of innate immune pathways.

Example 3

Materials and Methods for Example 4

1. DNA Template and p-shRNA Synthesis.

All reagents for in vitro transcription were purchased from New England Biolabs (NEB, Ipswich, Mass.). Custom PAGE-purified, 5'-phosphorylated DNA oligos and HPLC-purified RNA oligo were purchased from Integrated DNA Technologies (Coralville, Iowa) and resuspended in RNase-free water. For a typical reaction, DNA oligo was diluted to 3 µM in NEBNext® Quick Ligation Reaction Buffer and heated at 95° C. for 2 minutes before slowly cooling to room temperature. Ligation was carried out by adding 1 µL T4 DNA ligase (400,000 units/mL) to give a total ligation reaction volume of 120 µL. After a 2 hour incubation at room temperature, the ligation reaction was mixed with 20 µL 10× T7 RNA polymerase reaction buffer, 12.5 µL ribonucleotide solution mix, 1.5 µL water, 6 µL $MgCl_2$ (200 mM), and 40 µL T7 RNA polymerase (50,000 units/mL). Transcription was allowed to proceed for 24 hours at 37° C. before addition of 20 µL of 0.5 M ethylenediaminetetraacetic acid (EDTA) to dissolve RNA microsponges that were formed from RCT. The resulting p-shRNA from both the dissolved microsponges and the rest of the transcription reaction was purified by filtration using Advantec disposable ultrafiltration units (200 kDa molecular weight cutoff; Cole-Parmer, Vernon Hills, Ill.). For RCT yield quantification, the transcription reaction before purification was treated with DNase I, followed by addition of EDTA and analysis by Quant-IT Ribogreen® assay (Thermo Fisher Scientific, Cambridge, Mass.).

2. RNase Digestions.

Purified p-shRNA was diluted and incubated with RNase T1 (Thermo Fisher Scientific, Cambridge, Mass.) at a ratio of 1 µg RNA:1 unit RNase T1 in 50 mM Tris-HCl (pH 7.5) and 2 mM EDTA at 37° C. for one hour. For RNase I digestion, 1.5 µg p-shRNA was diluted in 1× NEBuffer 3 and incubated with 50 units of RNase $I_f$ (NEB) at 37° C. for 10 minutes before addition of 3 uL EDTA (0.5 M) and heating at 70° C. for 20 minutes to inactivate the enzyme. Digest products were analyzed on 15% precast Tris-borate-EDTA (TBE) or TBE-urea polyacrylamide gels (Bio-Rad, Hercules, Calif.), which were stained with GelRed™ (Biotium, Hayward, Calif.) for 1 hour before visualization with a UV transilluminator.

3. Dicer Cleavage Assays.

For each p-shRNA and op-shRNA, 500 ng of RNA were incubated with 1 unit of recombinant human Dicer enzyme (Genlantis, San Diego, Calif.) and reaction buffer at 37° C. according to the manufacturer's instructions. Aliquots of 10 µL were withdrawn at the specified timepoints, and 2 µL Dicer stop solution was added. Each timepoint sample along with a control RNA sample incubated at 37° C. without Dicer was analyzed on a 15% precast TBE polyacrylamide gel.

4. In Vitro Transfections.

GFP-expressing HeLa cells (Cell Biolabs, San Diego, Calif.) were cultured in Dulbecco's Modified Eagle Medium (Mediatech, Manassas, Va.) with 10% fetal bovine serum (FBS) and 1% penicillin-streptomycin (P/S), and firefly luciferase-expressing SKOV3 and UCI101 cells (generously contributed from Dr. Michael Birrer's group at Massachusetts General Hospital) were cultured in RPMI-1640 with 10% FBS, 1% P/S, and 40 µg/mL blasticidin, at 37° C. in a 5% $CO_2$ humidified atmosphere. One day before transfection, cells were seeded at 10,000 cells/well in a 96-well plate. After 24 hours, transfections with TransIT-X2 (Mirus Bio, Madison, Wis.) and Lipofectamine 2000 (Life Technologies, Carlsbad, Calif.) were carried out (with or without 1% P/S in the medium, respectively) with p-shRNA, op-shRNA, and siRNA according to the manufacturers' instructions. Complexes were added at the appropriate concentrations of effective siRNA, with each condition performed in triplicates. The medium was replaced with fresh medium 24 hours after transfection. Three days after transfection, GFP expression of HeLa cells was analyzed by flow cytometry (excitation 480 nm; emission 530 nm) using a BD FACSCalibur equipped with a high throughput sampler. Luciferase expression in SKOV3 and UCI101 cells was analyzed by the Steady-Glo luciferase assay system (Promega, Madison, Wis.) and normalized to total protein per well (Pierce BCA Protein Assay Kit, Thermo Fisher Scientific, Cambridge, Mass.), using a Tecan Infinite M200 Pro 96-well plate reader. For extended knockdown experiments, a quarter of the cells trypsinized for flow cytometry analysis were propagated every two days.

5. Cell Viability Assays.

For each cell line used for transfections, cells were seeded at 10,000 cells/well in a white 96-well plate. After 24 hours, p-shRNA and op-shRNA complexed with Lipofectamine 2000 or TransIT-X2 were added at increasing concentrations in triplicate wells. Cell viability was assessed by CellTiter-Glo luminescent cell viability assay (Promega, Madison, Wis.) after 48 hours of incubation.

6. Complex Formation with bPEI.

RNase T1-cleaved p-shRNA was purified and washed with 10 mM NaCl using a Nanosep centrifugal device (30 kDa MWCO; Pall Corporation, Westborough, Mass.). For the gel retardation assays, 2 kDa branched PEI (Sigma-Aldrich, St. Louis, Mo.) was added to an equal volume of either op-shRNA or siRNA diluted to 120 ng/µL at increasing N/P ratios. After thorough pipette mixing and incubation for 30 minutes at room temperature, the complexes were analyzed on a 2% agarose gel containing GelRedi'm in TBE buffer. The hydrodynamic sizes and zeta potentials of op-shRNA and siRNA complexes formed with 2 kDa branched PEI were measured using a Malvern Zetasizer Nano ZS90 particle analyzer. For the heparin displacement assays, op-shRNA and siRNA complexes were allowed to form with bPEI at N/P 15 for 30 minutes before addition of increasing amounts of heparin (Santa Cruz Biotechnology, Dallas, Tex.). After equilibration for 30 minutes, the heparin-complex mixtures were analyzed on a 2% agarose gel (1× TBE).

Example 4

Engineering Periodic shRNA for Enhanced Silencing Efficacy

Figure 21:
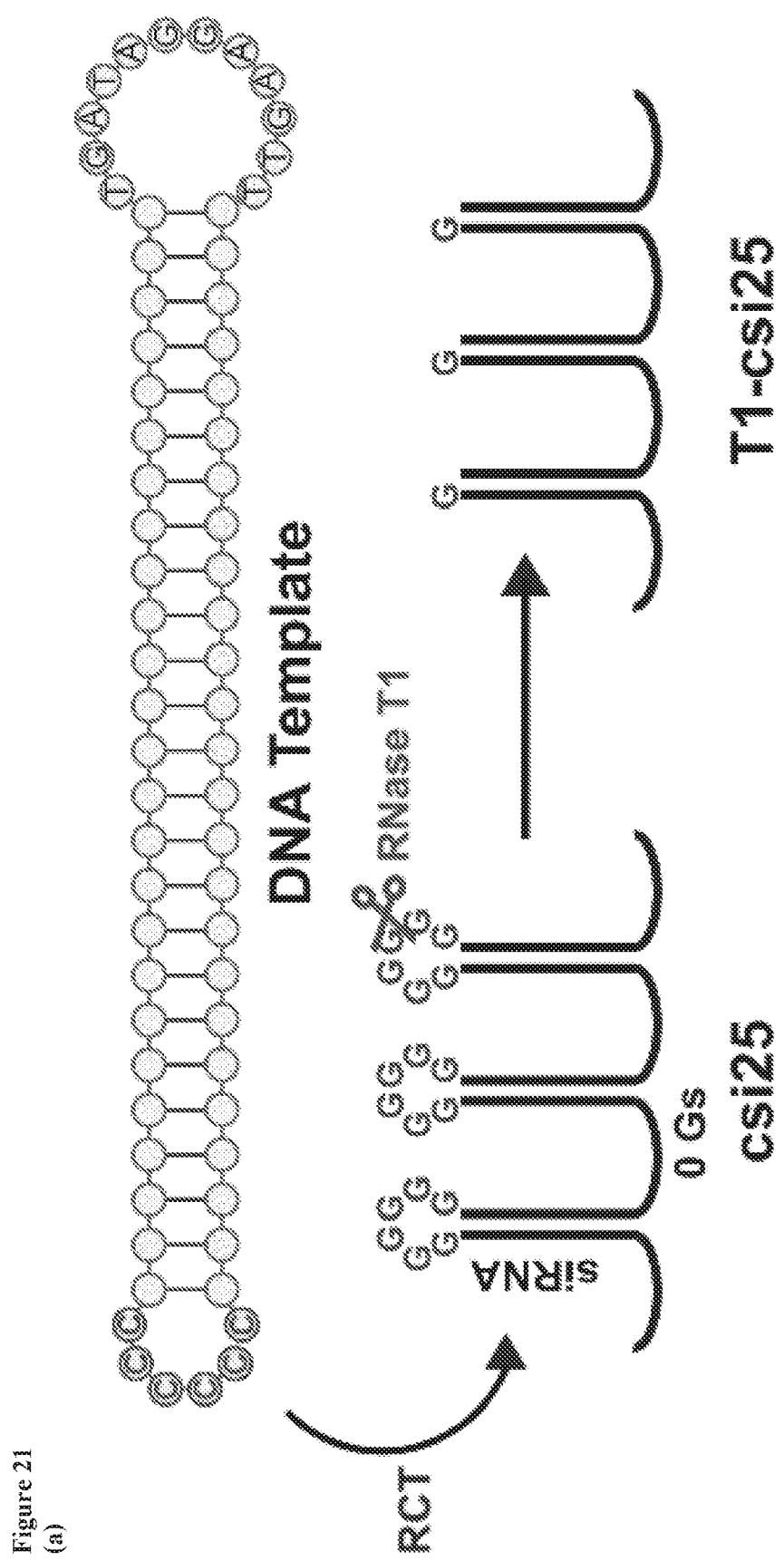
FIG. 21, Panel (a) is a schematic representation of the synthesis of open-ended p-shRNA by molecular engineering of p-shRNA structures enzymatically assembled from a dumbbell DNA template.
Figure 21:
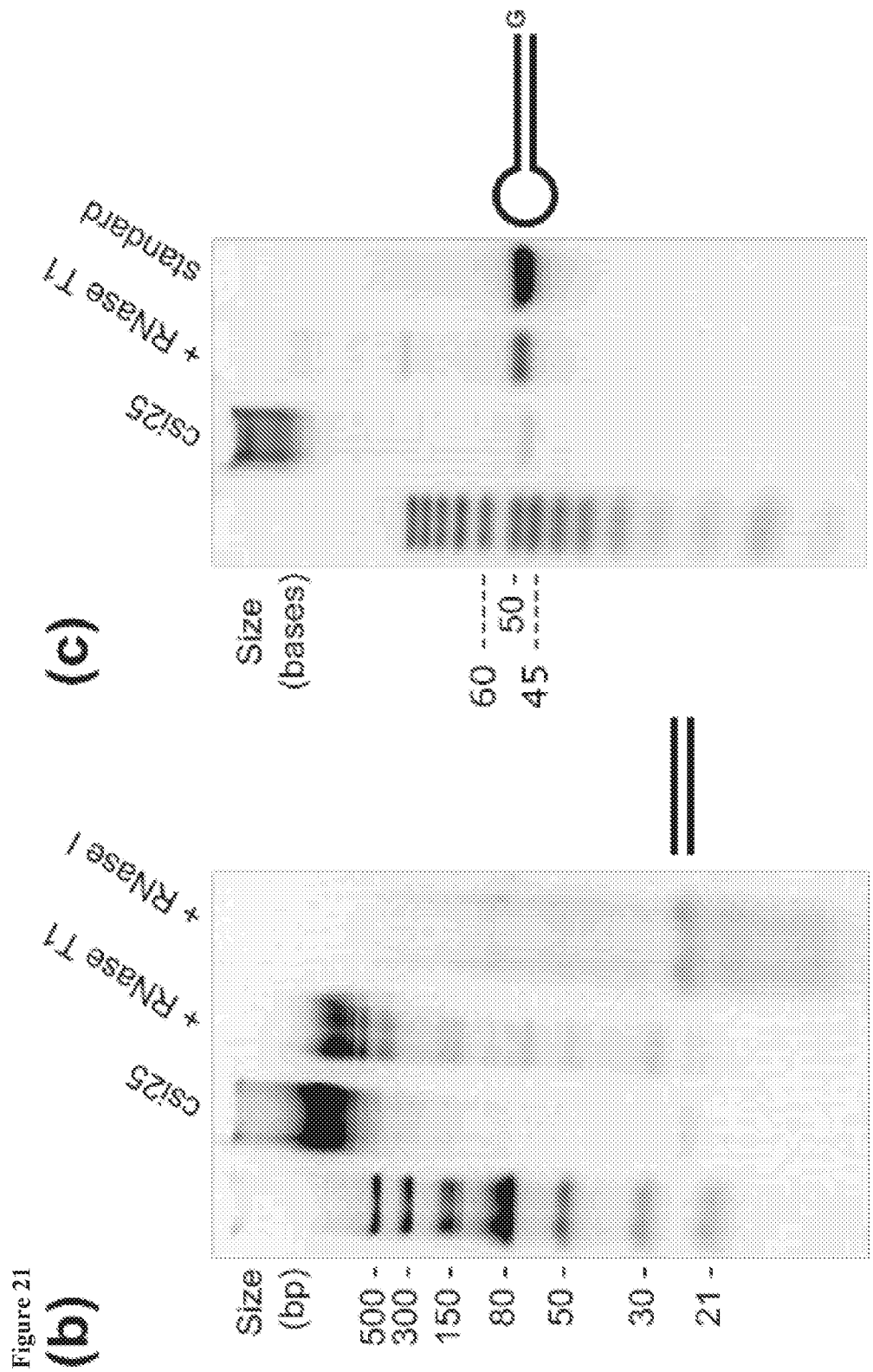
Figure 26:
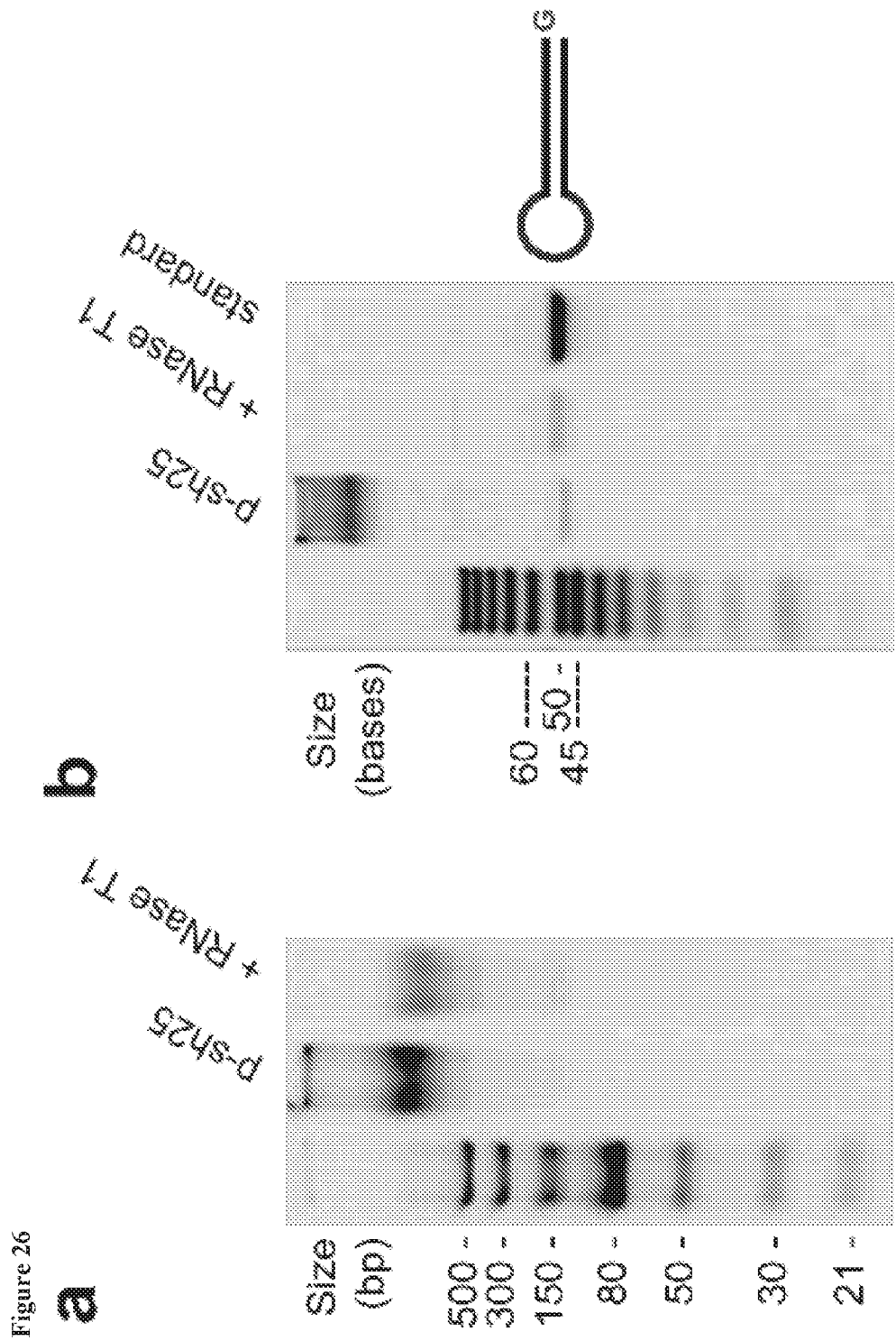
FIG. 26, Panel (a) is a photograph that depicts the results of analysis of RNase T1 digestion (one hour at 37° C.) of p-shRNA synthesized from the template in a (p-sh25), with a luciferase-targeting stem sequence, by 15% native polyacrylamide gel electrophoresis (PAGE).
Figure 26:
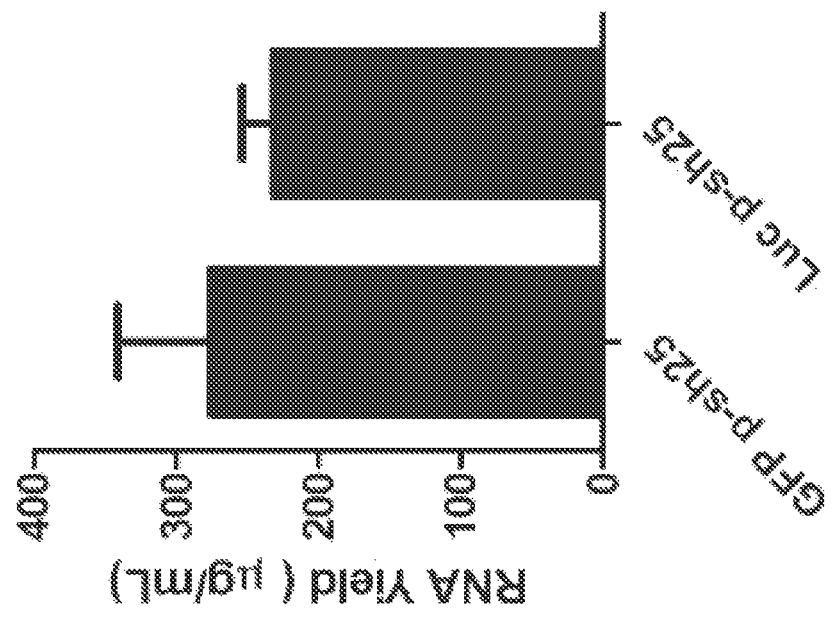

1. Design of Open-Ended p-shRNA by RNase T1 Digestion of p-shRNA Hairpin Loops To achieve selective processing, RNase T1 was used, which preferentially cleaves single stranded RNA (ssRNA) at the 3' ends of guanine (G) residues. The p-shRNA generated by RCT from a dumbbell template, using T7 RNA polymerase, folds into a kinetically trapped configuration: the loop at which RNA transcription initiates acts as the linker between shRNA monomers, while the other loop acts as the hairpin loop in each monomer (Shopsowitz, K E et al. (2015) *Nucleic Acids Res* 44: 545-557). By controlling the hairpin loops to contain one or more Gs and the linker loops to contain no Gs, it was predicted that RNase T1 would selectively cleave the hairpin loops to yield an open-ended p-shRNA (op-shRNA) that stably retains its polymeric form through base-pairing interactions. As an initial investigation, RCT was performed on a dumbbell DNA template with a 25 base pair (bp) stem and asymmetrically sized loops: a smaller loop (6 nt) containing all cytosines (Cs), encoding a loop of all Gs, and a larger loop (12 nt) containing no Cs (FIG. 21, Panel (a); all template sequences used in this study are listed in Table 4). The resulting p-shRNA (p-sh25) was a polydisperse high molecular weight polymer, as observed by native polyacrylamide gel electrophoresis (PAGE) (FIG. 21, Panel (b)). Following RNase T1 digestion, p-sh25 retained its polymeric form, appearing as a broad high molecular weight band by PAGE. Several shorter fragments were also visible, which could be caused by a portion of the p-shRNA not folding perfectly into the repeating hairpin configuration. In contrast, treatment of p-sh25 with RNase I, which preferentially cleaves ssRNA in a sequence-independent manner, yielded a main product of about 25 bp, consistent with complete cleavage of both loops. Complete digestion by RNase T1 was verified by comparing to a standard 63 nt RNA with the same sequence as the expected product under denaturing conditions (FIG. 21, Panel (c); all RNA sequences used in this study are listed in Table 5). The same RNase T1 digestion results was obtained with p-shRNA synthesized from a template with the same loops but different stem sequence (FIG. 26). Furthermore, as RCT efficiency by T7 RNA polymerase may vary with stem sequence, the p-shRNA yields from these two templates were quantified by Ribogreen assays and found comparable yields (276.2±65.2 and 231.9±22.2 ng/mL from GFP- and luciferase-targeting stems, respectively; FIG. 26).

TABLE 4

DNA template sequences used for rolling circle transcription. Bolded regions indicate double stranded stem region encoding siRNA sequence.

| Template or Encoded p-shRNA | Stem Target Sequence | Template Sequence |
|---|---|---|
| p-sh25 | GFP | 5'-CCTGAAGTTCATCTG TGATAGGAAGTT CAGATGAACTTCAGGGTCAGCTTGC CCCCCC GCAAGCTGAC-3' |
| p-sh25 | Firefly luciferase | 5'-GAGCACTTCTTCATC TGATAGGAAGTT GATGAAGAAG TGCTCGTCCT CGTCC CCCCCC GGACGAGGAC-3' |

TABLE 4-continued

DNA template sequences used for rolling circle transcription. Bolded regions indicate double stranded stem region encoding siRNA sequence.

| Template or Encoded p-shRNA | Stem Target Sequence | Template Sequence |
|---|---|---|
| 1 | GFP | 5'-CCTGAAGTTCATCTG TGATAGGAAGTT CAGATGAACTTCAGGGTCAGCTTGC CTGACC GCAAGCTGAC-3' |
| 2 | GFP | 5'-CCTGAAGTTCATCTG TGATAGGAAGTT CAGATGAACTTCAGGGTCAGCTTGC TTTCTT GCAAGCTGAC-3' |
| 3 | GFP | 5'-CCTGAAGTTCATCTG TGATAGGAAGTT CAGATGAACTTCAGGGTCAGCTTGC CCATAGGAAGCC GCAAGCTGAC-3' |
| 4 | GFP | 5'-CCTGAAGTTCATCTG TGATAGGAAGTT CAGATGAACTTCAGGGTCAGCTTGC CCCCCCCCCCCC GCAAGCTGAC-3' |
| 5 | GFP | 5'-CCTGAAGTTCATCTG CCCCCCCCCCCC CAGATGAACTTCAGGGTCAGCTTGC TGATAT GCAAGCTGAC-3' |
| 6 | GFP | 5'-CCTGAAGTTCATCTG CCATAGGAAGCC CAGATGAACTTCAGGGTCAGCTTGC TGATAT GCAAGCTGAC-3' |
| p-sh25 2nt (FIG. S3) | GFP | 5'-CCTGAAGTTCATCTG TGATAGGAAGTT CAGATGAACTTCAGGGTCAGCTTGC CCCCCT GCAAGCTGAC-3' |
| p-sh21 | GFP | 5'-CCTGAAGTTCA TGATAGGAAGTT TGAACTTCAGGGTCAGCTTGC CCCCCC GCAAGCTGAC-3' |
| p-sh27 | GFP | 5'-CCTGAAGTTCATCTGCA TGATAGGAAGTT TGCAGATGAACTTCAGGGTCAGCTTGC CCCCCC GCAAGCTGAC-3' |
| p-sh29 | GFP | 5'-CCTGAAGTTCATCTGCACC TGATAGGAAGTT GGTGCAGATGAACTTCAGGGTCAGCTTGC CCCCCC GCAAGCTGAC-3' |

TABLE 5

Sequences of siRNAs and standard RNA used in this study. The standard RNA was compared by 15% denaturing polyacrylamide gel electrophoresis to RNase T1-treated p-sh25. For in vitro knockdown studies, GFP-targeting and firefly luciferase-targeting siRNAs (siGFP and siLuc, respectively) were used.

| RNA | Sequence |
|---|---|
| Standard RNA | 5'-GCAAGCUGACCCUGAAGUUCAUCUGAACUUCCUAUCA CAGAUGAACUUCAGGGUCAGCUUGCG-3' |
| siGFP | 5'-GCAAGCUGACCCUGAAGUUCAUdTdT-3' |
| siLuc | 5'-GGACGAGGACGAGCACUUCdTdT-3' |

Figure 22:
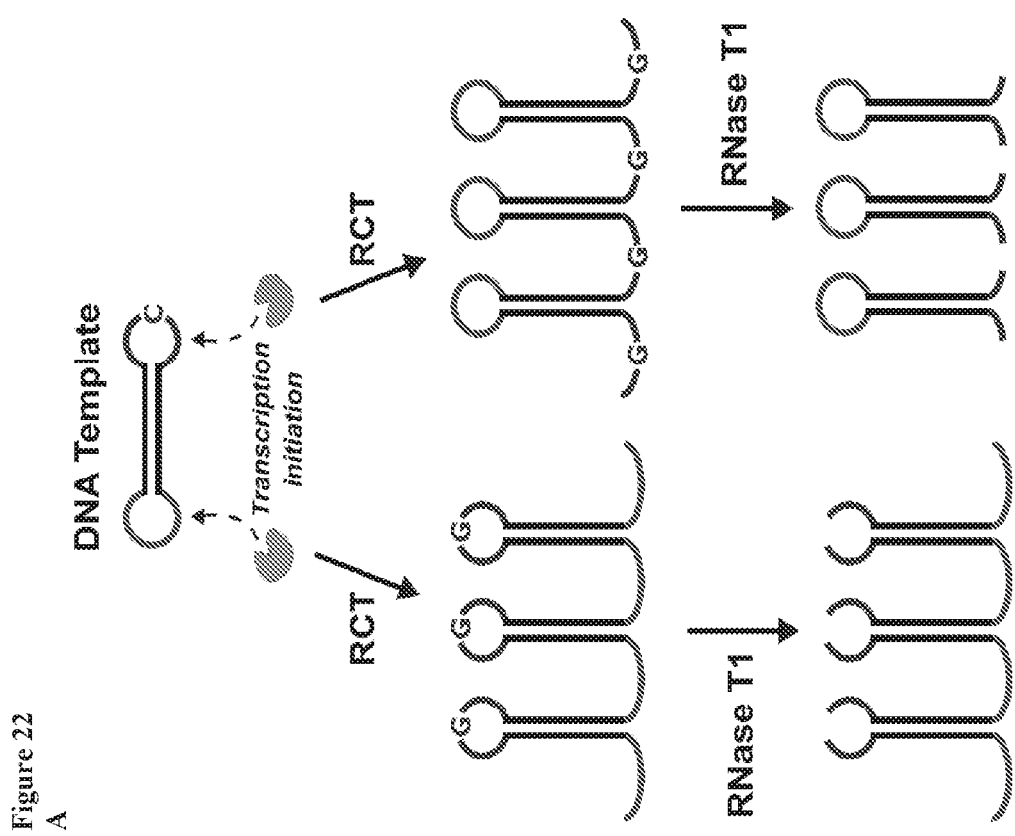
FIG. 22, Panel (a) is a schematic representation of the effect of transcription initiation site on the relative positions of the G-containing and non-G-containing loops in p-shRNA and the resulting main RNase T1 digestion products.
Figure 22B:
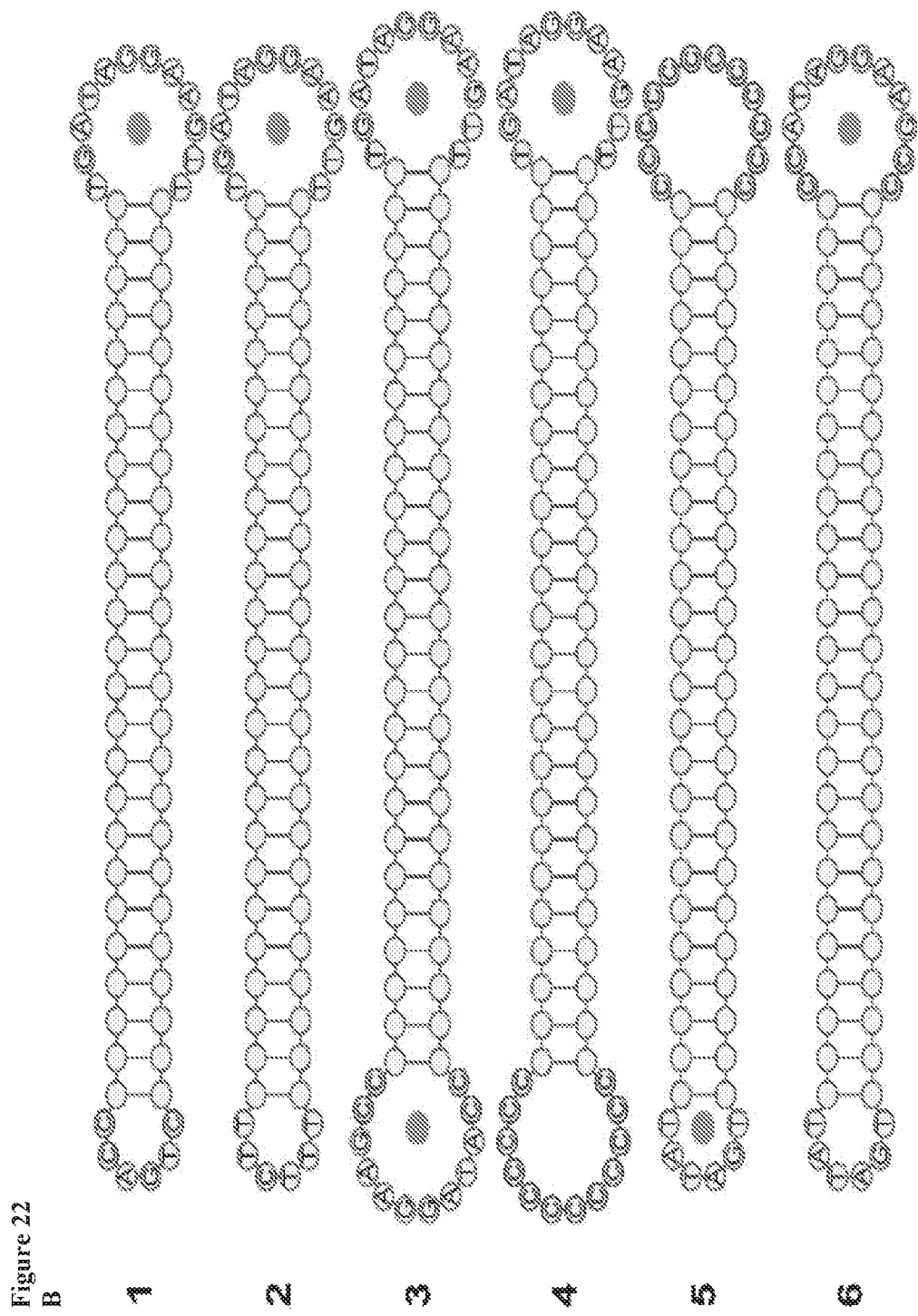
Figure 22:
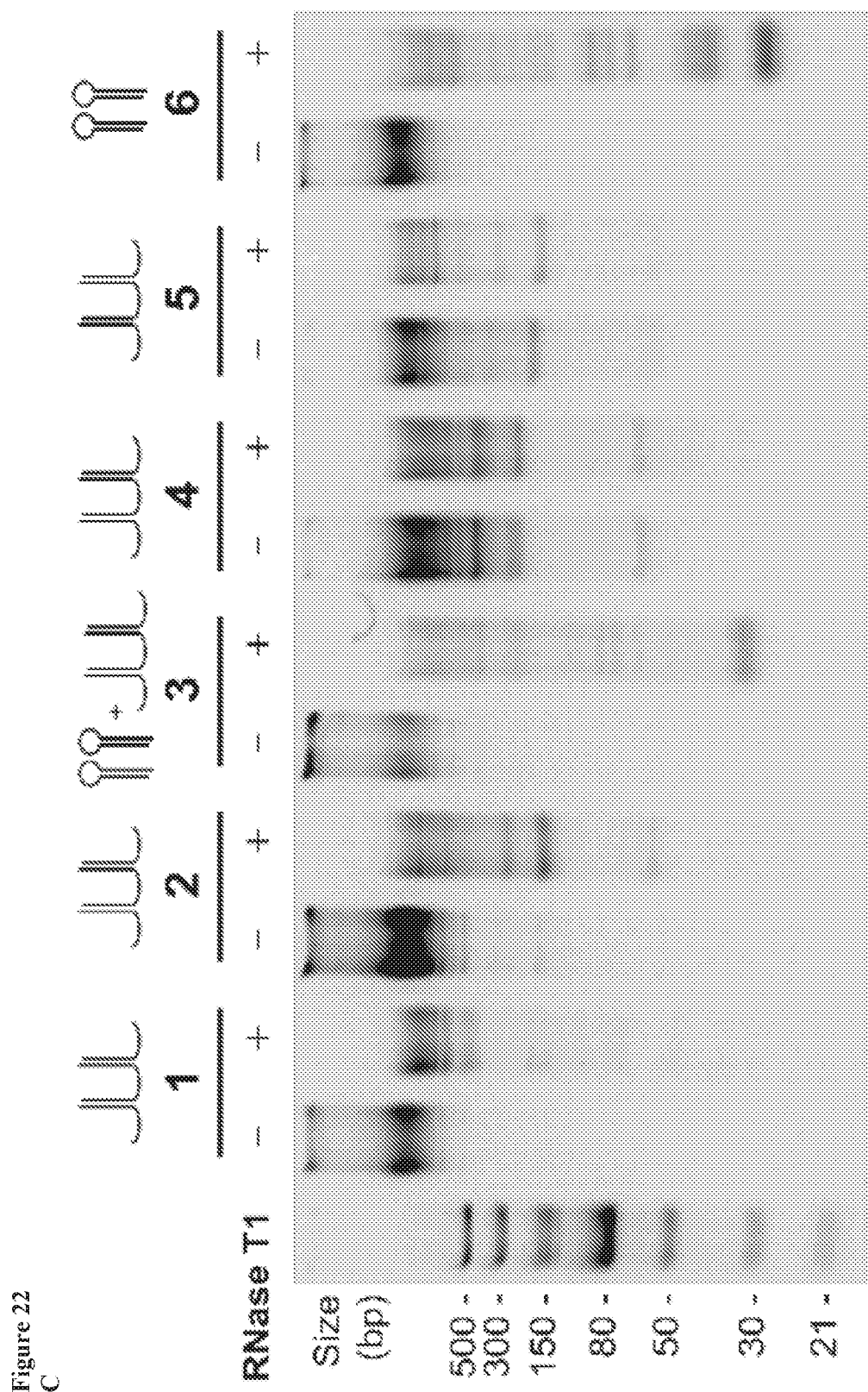

To investigate how transcription initiation site and thereby relative p-shRNA loop positions could be controlled to generate op-shRNA, additional templates were designed with various loop sizes and sequences, keeping the stem constant (FIG. 22, Panels (a) and (b)). When the smaller loop in the p-sh25 template consisted of a mixed sequence rather than entirely Cs (templates 1 and 2), RNase T1 treatment of the resulting p-shRNA structures also yielded the desired polymeric products (FIG. 22, Panel (b)). As a control to confirm that differential loop size influences the relative p-shRNA loop positions, a template was designed with both loops of equal size and similar sequences (template 3), which was predicted to result in the loops occurring at either position with a similar likelihood, due to transcription initiating randomly at each loop. RNase T1 cleavage of the resulting p-shRNA produced a mix of polymeric and short fragments, consistent with this prediction.

To determine whether template loop sequence also plays a role in p-shRNA folding, templates were tested in which the C-containing loop consisted of all Cs and the other loop was of equal size or smaller (templates 4 and 5, respectively). The resulting p-shRNAs retained their polymeric forms after RNase T1 digestion (FIG. 22, Panel (b)). Changing the sequence of the all-C loop in template 5 to a mixed sequence (template 6) yielded a prominent short fragment following RNase T1 treatment, indicating that the C-containing loop was in the linker position in most of the p-shRNA repeats.

Figure 23:
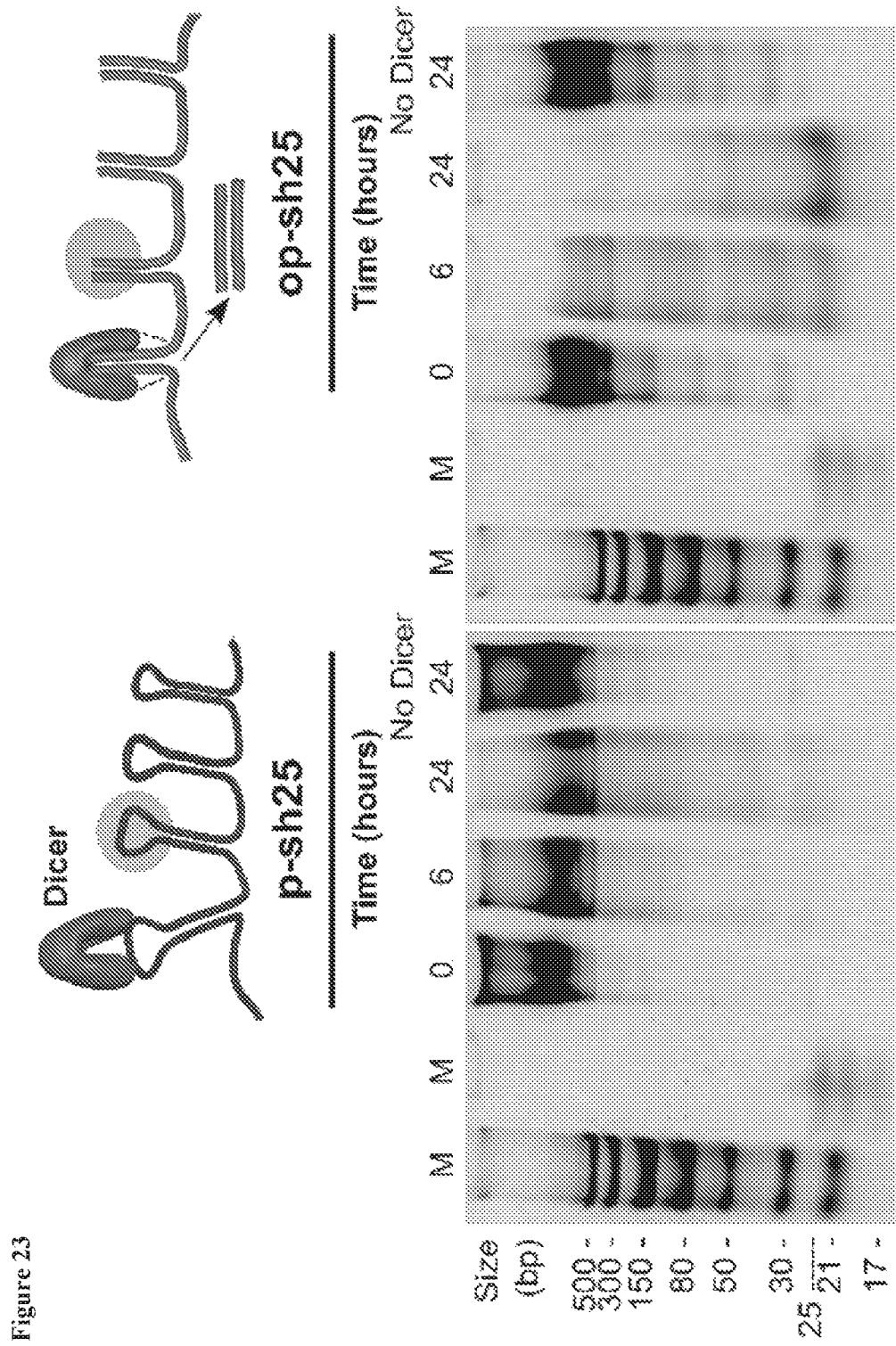
FIG. 23 is a photograph that depicts the results of an analysis by 15% native polyacrylamide gel electrophoresis of p-sh25 and op-sh25 following incubation with recombinant human Dicer at 37° C. up to 24 hours, each shown along with a control incubated for 24 hours without Dicer, and double stranded RNA markers (M).

Having confirmed RNase T1 cleavage of our p-shRNA structures into an open-ended polymeric form, it was next tested whether the engineered open ends facilitate Dicer processing. Incubation of p-sh25 with recombinant Dicer enzyme led to the gradual appearance of smaller polymeric fragments but very little 21-25 bp product, with the majority of p-sh25 remaining undigested or incompletely digested after 24 hours (FIG. 23). In contrast, Dicer treatment of T1-cleaved p-sh25 (op-sh25) yielded about 54% conversion into fragments slightly longer than 21 bp after 24 hours—a more than tenfold higher processing efficiency compared to p-sh25.

2. Silencing Efficacy of op-shRNA

Figure 24:
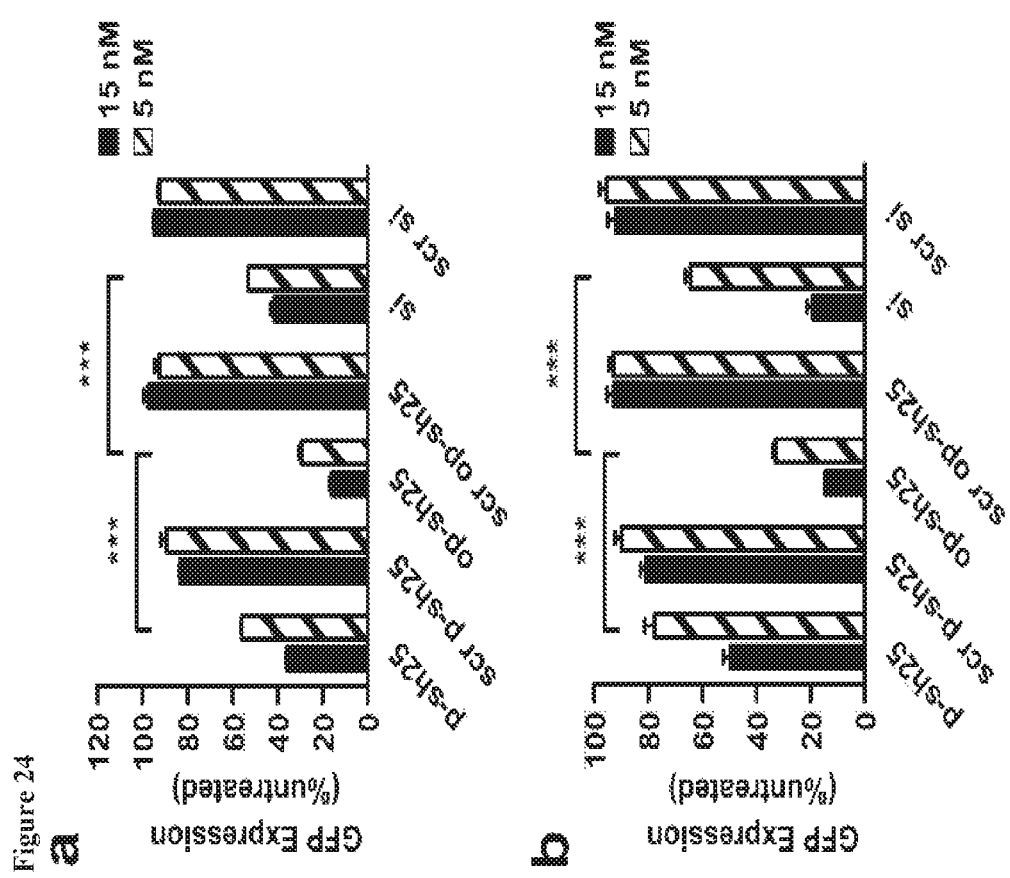
FIG. 24, Panels (a) and (b) are bar graphs showing the results of GFP knockdown in GFP-expressing HeLa cells by GFP-targeting and scrambled (scr) p-sh25, op-sh25, and siRNA transfected with Lipofectamine 2000® (Panel (a)) and TransIT-X2® (Panel (b)), with the indicated concentrations in p-sh25 and op-sh25 based on effective siRNA repeats.
Figure 24:
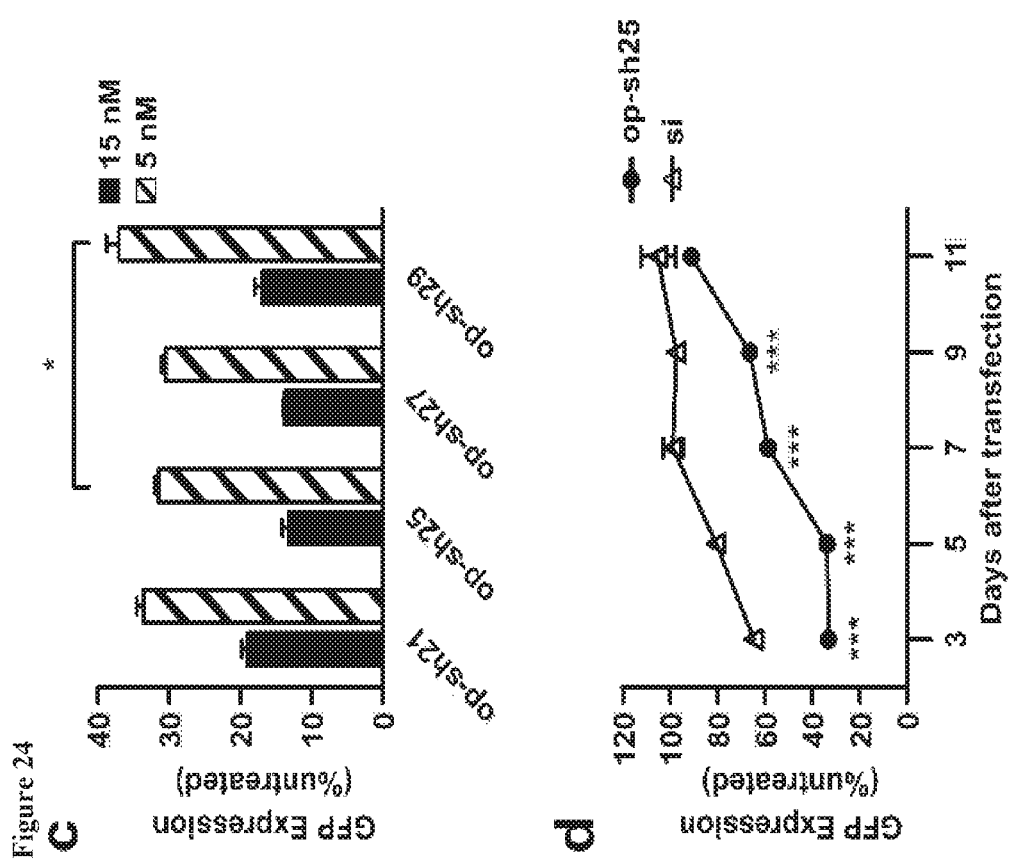
Figure 24:
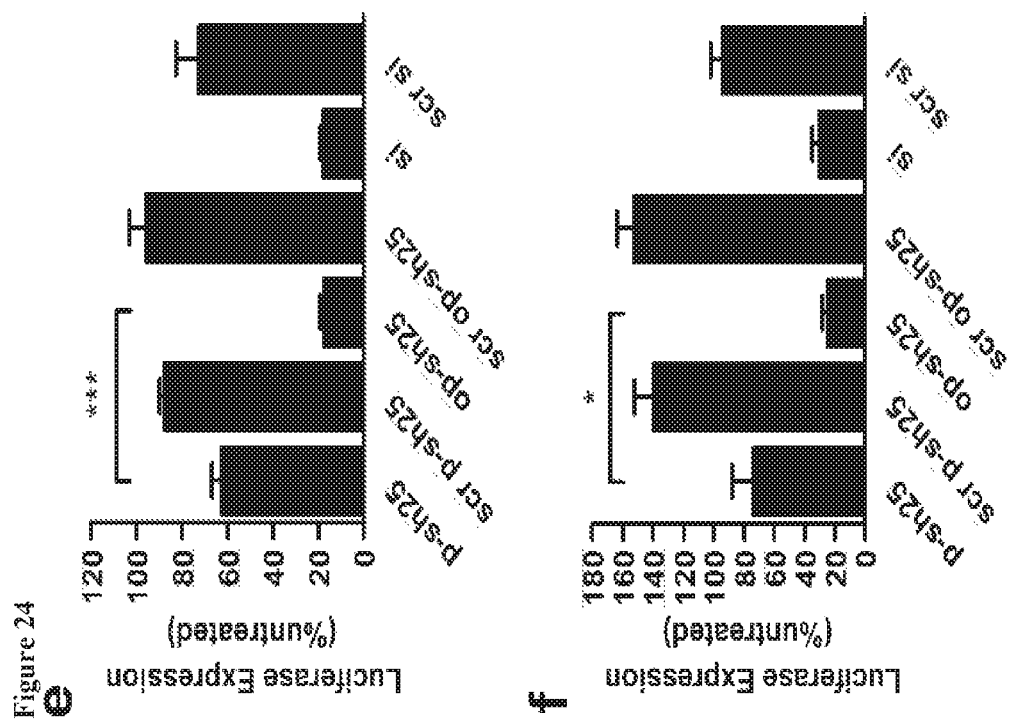
Figure 27:
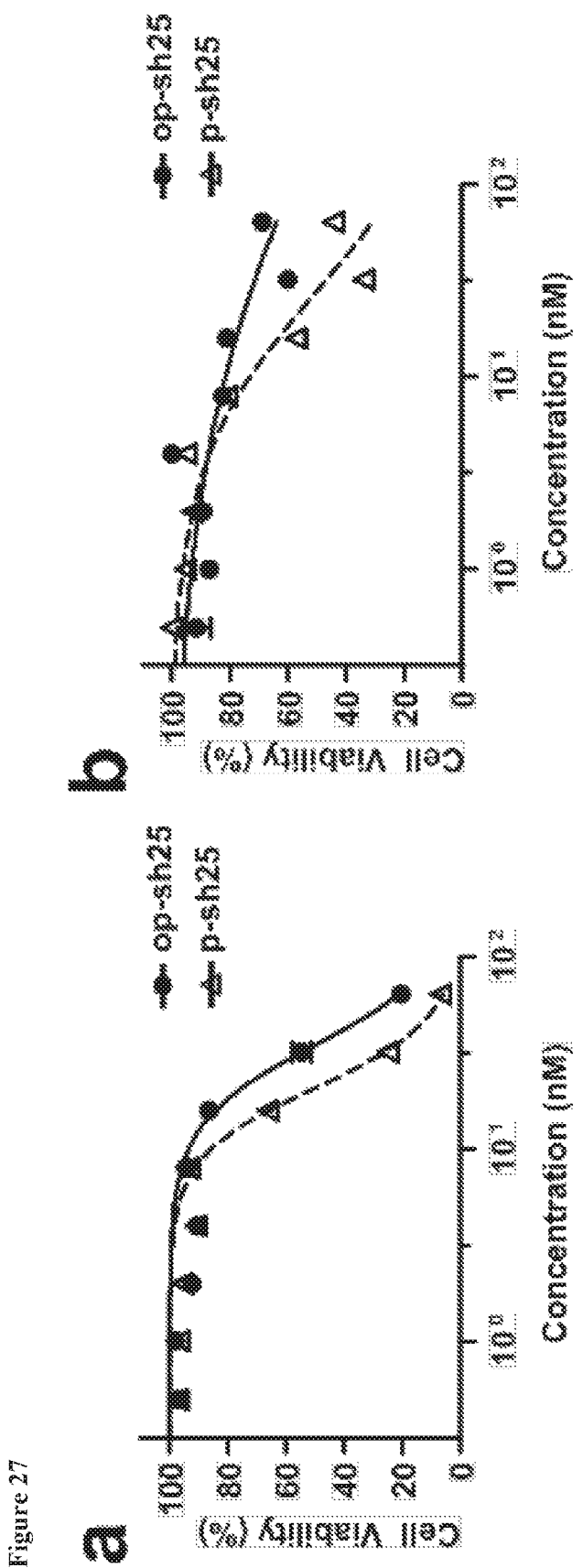
FIG. 27, Panels (a)-(d) are line graphs showing the results of viability assays of p-shRNA and op-shRNA with 25 bp stems (p-sh25 and op-sh25, respectively) with Lipofectamine 2000® (Panel (a)) and TransIT-X2® (Panel (b)) in GFP-expressing HeLa cells, and with TransIT-X2® in luciferase-expressing SKOV3 (Panel (c)) and UCI101 (Panel (d)) cells. Results are presented as mean±SEM, n=3.
Figure 27:
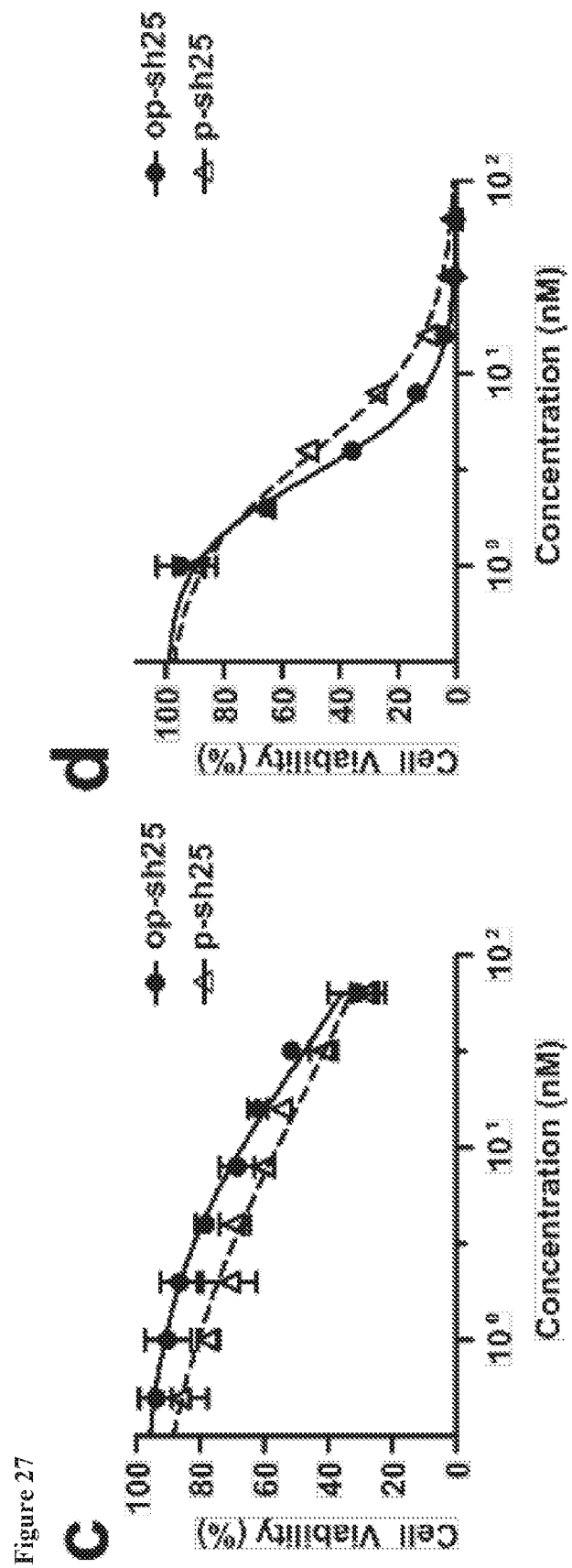

To test the silencing activity of op-shRNA, green fluorescent protein (GFP)-expressing HeLa cells were transfected with p-sh25, op-sh25, and a standard siRNA targeting GFP. With Lipofectamine 2000, op-sh25 caused greater knockdown than p-sh25 at each tested concentration (5 and 15 nM, based on effective siRNA repeat units; FIG. 24, Panel (a)). Notably, op-sh25 exhibited significantly greater potency than siRNA, with 70% knockdown and minimal nonspecific silencing at 5 nM. Scrambled op-shRNA induced slightly less nonspecific silencing than scrambled p-shRNA, and viability assays with Lipofectamine showed similar cytotoxicities of p-sh25 and op-sh25 in HeLa cells (FIG. 27). With TransIT-X2, a commercial polymeric transfection reagent, op-sh25 also demonstrated superior potency to p-sh25, inducing about 85% and 70% knockdown in HeLa cells at 15 and 5 nM, respectively (FIG. 24, Panel (b)). At 5 nM, op-sh25 induced nearly twofold more knockdown than siRNA. The toxicity of op-sh25 with TransIT-X2 was also slightly lower than that of p-sh25, though transfection with TransIT-X2 generally produced less toxicity than with Lipofectamine (FIG. 27).

Figure 28:
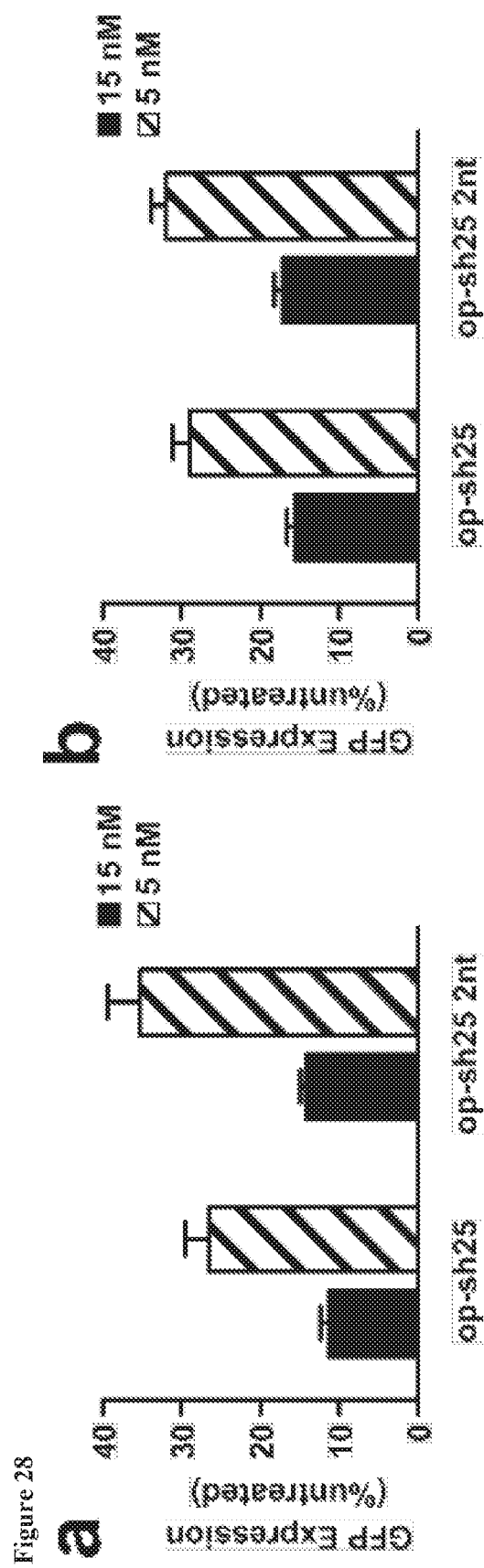
FIG. 28, Panels (a) and (b) are bar graphs depicting the results of GFP knockdown in GFP-expressing HeLa cells by op-shRNA (25 bp stem) structures with 1 and 2 nucleotide 3' overhangs (op-sh25 and op-sh25 2 nt, respectively), with Lipofectamine 2000® (Panel (a)) and TransIT-X2® (Panel (b)). Results are presented as mean±SEM, n=3.

It was next investigated whether the stem length of op-shRNA influences its potency. Stem lengths longer than 21 bp have been reported to increase silencing by siRNAs and shRNAs. (Kim, D H et al. (2005) *Nat Biotechnol* 23: 222-226; Siolas, D et al. (2005) *Nat Biotechnol* 23: 227-231). With TransIT-X2, op-shRNA structures generated from the same template as op-sh25 but with stem lengths varying from 21 to 29 bp, showed similar silencing efficiencies, with op-sh29 showing slightly less potency (FIG. 24, Panel (c)). To test whether further potency could be improved, a modified p-sh25 was designed such that T1 cleavage would theoretically leave the most efficient end structure for Dicer recognition (i.e., a 2 nt 3' overhang on each antisense strand). However, this modified op-shRNA exhibited a similar potency to that of the original op-sh25 with a 1 nt 3' overhang (FIG. 28).

Since op-shRNA activity requires intracellular processing by Dicer, it was postulated that the gradual breakdown of op-shRNA could yield prolonged knockdown compared to monomeric siRNA. At 5 nM, op-sh25 reduced GFP expression up to nine days in HeLa cells, versus five days using siRNA (FIG. 24, Panel (d)). To further confirm the efficacy of op-shRNA, several ovarian cancer cell lines were transfected with p-sh25, op-sh25, and siRNA using TransIT-X2. At 5 nM, op-sh25 again demonstrated high potency, producing over 80% and 75% knockdown of firefly luciferase in luciferase-expressing SKOV3 and UCI101 cells, respectively (FIG. 24, Panel (e),(f)). Compared to siRNA, op-sh25 showed greater specific knockdown when normalized to the luciferase expression of cells treated with scrambled sequences. Similar cytotoxicities of p-sh25 and op-sh25 in both ovarian cancer cell lines were also observed (FIG. 27).

3. Complexation with Low Molecular Weight Polycation

Figure 25:
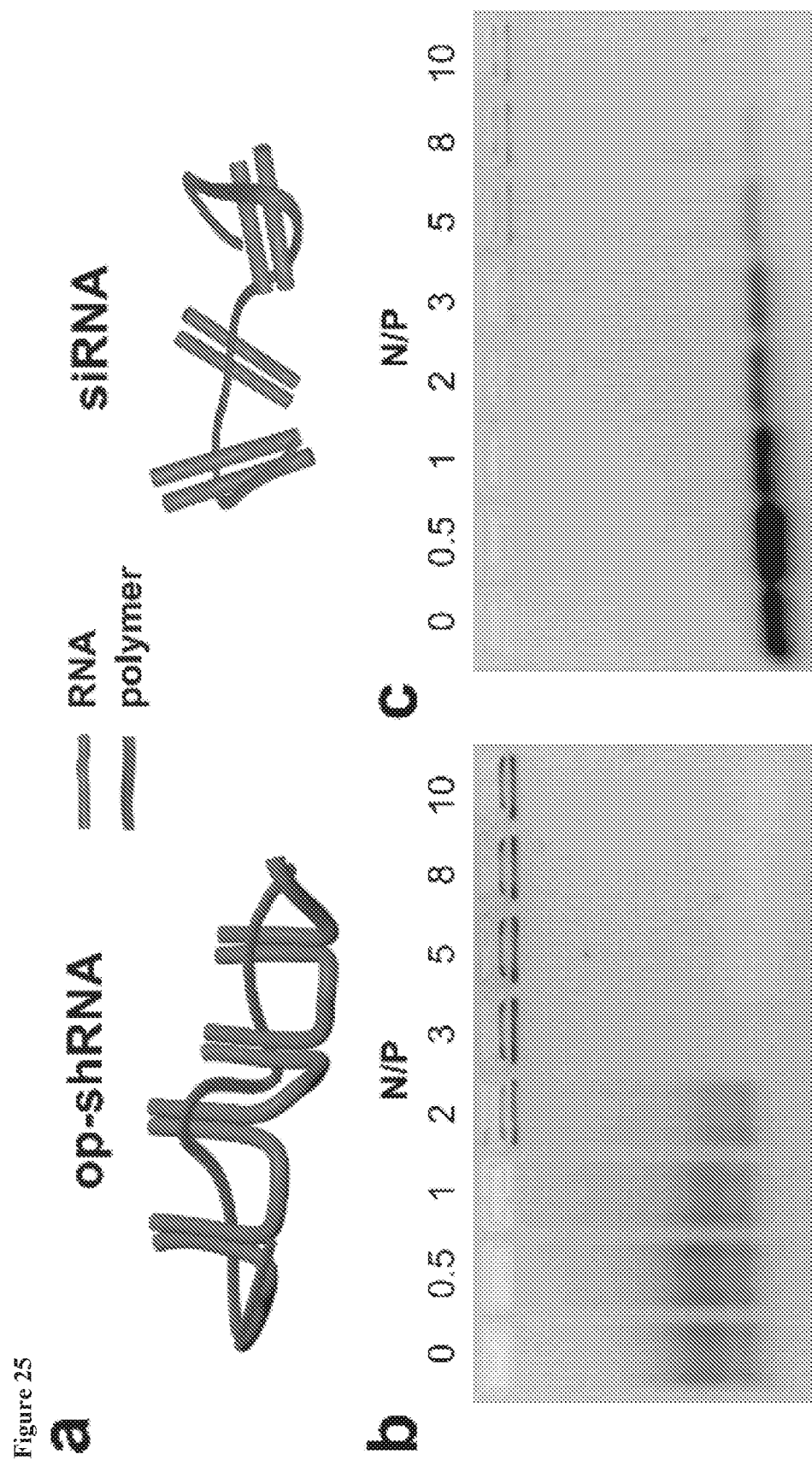
FIG. 25, Panel (a) is a graphical illustration of op-shRNA and siRNA complexation with cationic polymer.
Figure 25:
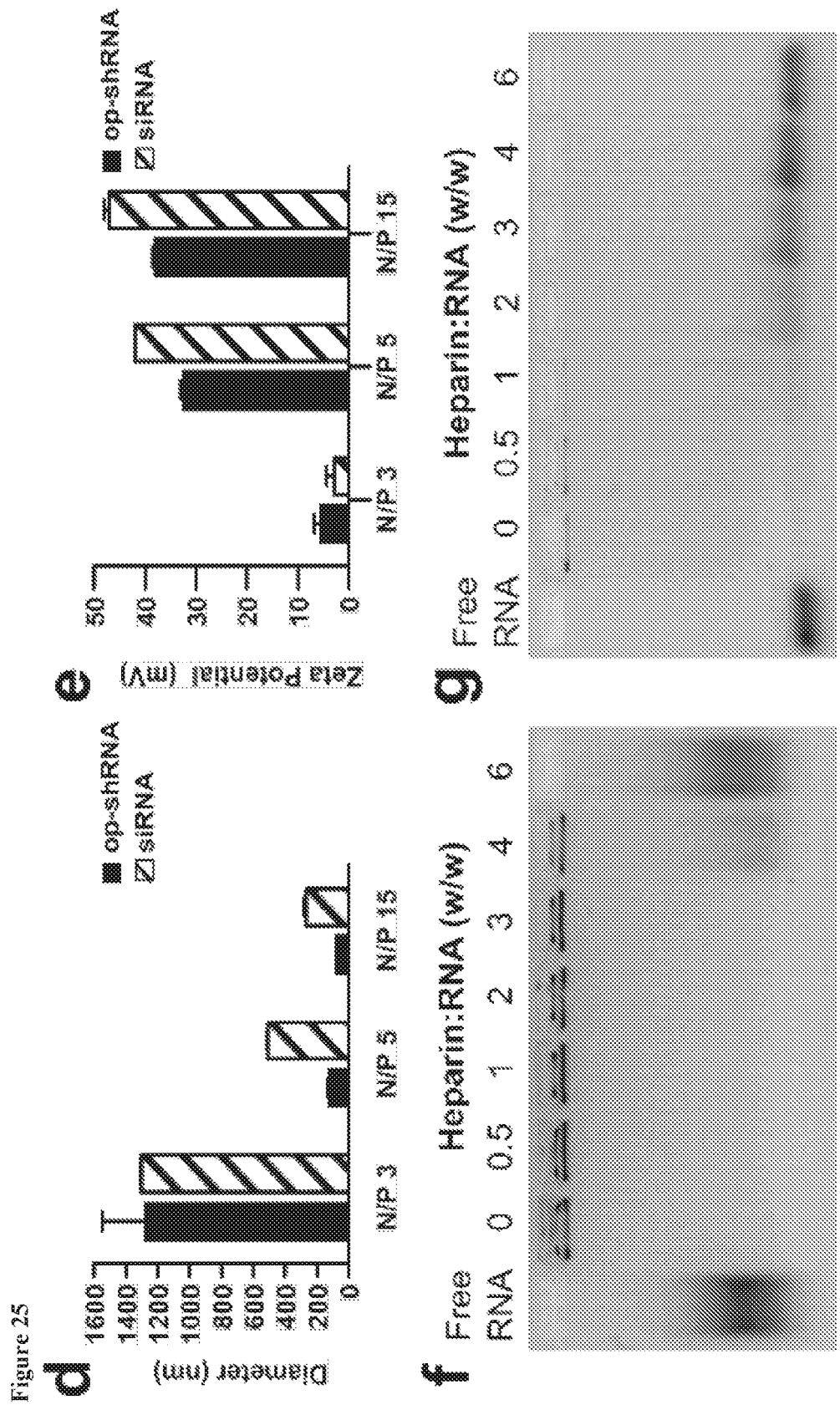

With its high potency and large molecular weight, op-shRNA can potentially enable more stable and efficacious RNAi delivery (FIG. 25, Panel (a)). As a proof-of-concept, op-shRNA and siRNA complexation was compared with low molecular weight (2 kDa) branched polyethyleneimine (PEI), which has been reported as an effective, less toxic alternative to 25 kDa branched PEI for gene delivery (Kunath, K et al. (2003) *J Control Release* 89: 113-125). Gel retardation assays showed that op-shRNA complexed much more readily than siRNA with PEI, attaining full complexation at a nitrogen to phosphorus (N/P) ratio of 3, while siRNA did not achieve full complexation up to N/P 10 (FIG. 25, Panels (b) and (c)). At N/P 5 and above, op-shRNA formed compact particles with PEI, with diameters of 122.7±5.4 and 77.1±1.7 nm at N/P ratios of 5 and 15, respectively, as measured by dynamic light scattering (FIG. 25, Panel (d)). On the other hand, particles formed by siRNA at the corresponding N/P ratios were significantly larger, remaining above 250 nm in diameter at N/P 15. Zeta potential measurements showed that both op-shRNA and siRNA complexes had highly positive surface charges at N/P 5 and above (FIG. 25, Panel (e)). Heparin displacement assays of polyplexes formed at N/P 15, where siRNA was fully complexed, were carried out to compare stabilities (FIG. 25, Panels (f) and (g)). SiRNA displacement was observed at a 0.5:1 heparin:RNA ratio (w/w), with complete siRNA release occurring at about a 2:1 ratio. In contrast, op-shRNA displacement only began at a much higher ratio of 4:1, indicating greater complex stability.

In conclusion, an open-ended csiRNA has been developed with vastly improved Dicer processing efficiency and silencing potency, which can be generated in high quantities with RCT. Having determined effects of loop size and sequence on transcription initiation and thereby csiRNA folding, open-ended csiRNAs with specific sequences and structures can be designed by manipulating template sequence and loop sizes. The ability of T1-csiRNA to form more stable complexes than siRNA using less cationic polymer, along with its potent silencing and immunostimulatory capabilities that could potentially work synergistically, makes it a promising platform for systemic delivery of RNAi therapeutics.

INCORPORATION BY REFERENCE

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Equivalents

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A concatemeric RNA molecule, comprising at least a first and a second repeat units, each of the first and the second repeat units including:
   a first segment having a first nucleotide sequence;
   a second segment having a second nucleotide sequence, complementary to the first nucleotide sequence; and
   a connecting segment covalently attached to the second segment,
   wherein the first segment and the second segment of at least one of the first or the second repeat units are not covalently attached.

2. A concatemeric RNA molecule, comprising at least a first and a second repeat units, each of the first and the second repeat units including:
   a first segment having a first nucleotide sequence;
   a second segment having a second nucleotide sequence, complementary to the first nucleotide sequence; and
   a connecting segment covalently attached to the second segment,
   wherein at least one of the first or the second repeat units further includes a loop segment having a loop nucleotide sequence, the loop segment being covalently attached to the first and the second segments,
   wherein the loop nucleotide sequence includes at least one enzyme-specific nucleotide sequence; said enzyme-specific nucleotide sequence is excluded from the connecting segment.

3. The concatemeric RNA molecule of claim 2, wherein the first segment, the second segment, and the loop segment of at least one of the first or the second repeat units form a hairpin loop structure by non-covalent complementary nucleotide pairing of the first nucleotide sequence and the second nucleotide sequence.

4. The concatemeric RNA molecule of claim 2, wherein the enzyme is selected from the group consisting of RNAse T1, RNAse T2, RNase U2, RNase A, RNase H, and ribozyme.

5. The concatemeric RNA molecule of claim 2, wherein the enzyme-specific nucleotide sequence is a self-cleaving ribozyme sequence.

6. The concatemeric RNA molecule of claim 1, wherein each connecting segment contains 4 nucleotides to 20 nucleotides.

7. The concatemeric RNA molecule of claim 6, wherein the connecting segment contains 6 nucleotides or 12 nucleotides.

8. The concatemeric RNA molecule of claim 2, wherein the loop segment contains 4 nucleotides to 20 nucleotides.

9. The concatemeric RNA molecule of claim 8, wherein the loop segment contains 6 nucleotides or 12 nucleotides.

10. The concatemeric RNA molecule of claim 2, wherein the first and second segment form a double stranded stem segment comprising anti-sense and sense strands containing 19 nucleotides to 50 nucleotides.

11. The concatemeric RNA molecule of claim 2, wherein the first and second segment comprise a silencing sequence.

12. The concatemeric RNA molecule of claim 11, wherein the silencing sequence comprises an RNAi target sequence.

13. The concatemeric RNA molecule of claim 12, wherein the RNAi target sequence silences a human or non-human gene.

14. A pharmaceutical composition comprising the concatemeric RNA molecule of claim 2.

15. A particle comprising the concatemeric RNA molecule of Claim 2.

16. A method for generating a concatemeric RNA molecule comprising:
   (a) providing a DNA template;
   (b) transcribing said DNA template by rolling circle transcription (RCT) or rolling circle amplification (RCA) under appropriate conditions to yield a plurality of concatemeric RNA molecules;
      wherein the RNA molecule comprises at least a first and a second repeat units,
      each of the first and the second repeat units including:
         a first segment having a first nucleotide sequence;
         a second segment having a second nucleotide sequence, complementary to the first nucleotide sequence;
         a connecting segment covalently attached to the second segment, wherein the connecting segment of the first repeat unit is covalently attached to the first segment of the second repeat unit; and
         a loop segment having a loop nucleotide sequence, the loop segment being covalently attached to the first and the second segments, wherein the loop nucleotide sequence includes at least one enzyme-specific nucleotide sequence; said enzyme-specific nucleotide sequence is excluded from the connecting segment and
   (c) isolating the plurality of concatemeric RNA molecules.

17. The method of claim 16, wherein the DNA template comprises a dumbbell DNA template.

18. The method of claim 16, wherein the DNA template comprises a DNA molecule comprising a stem region, a first loop region, and a second loop region.

19. The method of claim 18, wherein the stem region of said DNA template comprises a double stranded DNA molecule contains 19 nucleotides to 50 nucleotides.

20. The method of claim 19, wherein the stem region of said DNA template comprises contains 25 nucleotides.

21. The method of claim 16, wherein the DNA template comprises a silencing sequence.

22. The method of claim 18, wherein the first and second loop region contains 4 nucleotides to 20 nucleotides.

23. The method of claim 22, wherein the first loop region of said DNA template contains 6 nucleotides and the second loop region contains 12 nucleotides.

24. The method of claim 22, wherein the first loop region of said DNA template contains 12 nucleotides and the second loop region contains 12 nucleotides.

25. The method of claim 22, wherein the first loop region of said DNA template comprises a nucleotide sequence having at least one Cytosine nucleotide.

26. The method of claim 25, wherein the first loop region of said DNA template comprises a nucleotide sequence having all Cytosine nucleotides.

27. The method of claim 25, wherein the first loop region of said DNA template comprises a nucleotide sequence having no Cytosine nucleotides.

28. The method of claim 22, wherein the second loop region of said DNA template comprises a nucleotide sequence having at least one Cytosine nucleotide.

29. The method of claim 28, wherein the second loop region of said DNA template comprises a nucleotide sequence having all Cytosine nucleotides.

30. The method of claim 28, wherein the second loop region of said DNA template comprises a nucleotide sequence having no Cytosine nucleotides.

31. The method of claim 25, wherein the first loop region of said DNA template comprises a Cytosine nucleotide at positions 1, 5, and 6 from the 5' end of the first loop region.

32. The method of claim 25, wherein the first loop region of said DNA template comprises a Cytosine nucleotide at position 4 from the 5' end of the first loop region.

33. The method of claim 16, further comprising a step (d), wherein the step (d) comprises contacting the isolated concatemeric RNA molecules of step (c) to at least one enzyme.

34. The method of claim 33, wherein the at least one enzyme is selected from the group consisting of RNAse T1, RNAse T2, RNase U2, RNase A, RNase H, and ribozyme.

35. The method of claim 16, wherein step (b) further includes contacting the DNA template by an RNA polymerase.

36. The method of claim 35, wherein the RNA polymerase is selected from T7 bacteriophage, phage T3, or phage SP6.

37. A method of gene silencing comprising administering to a subject in need thereof a therapeutically effective amount of the RNA molecule of claim 1 or claim 2.

38. The concatemeric RNA molecule of claim 1, wherein the first and second segment form a double stranded stem segment comprising anti-sense and sense strands containing 19 nucleotides to 50 nucleotides.

39. The concatemeric RNA molecule of claim 1, wherein the first and second segment comprise a silencing sequence.

40. The concatemeric RNA molecule of claim 39, wherein the silencing sequence comprises an RNAi target sequence.

41. The concatemeric RNA molecule of claim 40, wherein the RNAi target sequence silences a human or non-human gene.

42. A pharmaceutical composition comprising the concatemeric RNA molecule of claim 1.

43. A particle comprising the concatemeric RNA molecule of claim 1.

44. The concatemeric RNA molecule of claim 40, wherein the RNAi target sequence silences a non-human gene.

* * * * *